US009632074B2

(12) United States Patent
Cheresh et al.

(10) Patent No.: US 9,632,074 B2
(45) Date of Patent: Apr. 25, 2017

(54) COMPOSITIONS AND METHODS FOR TREATING CANCER AND DISEASES AND CONDITIONS RESPONSIVE TO CELL GROWTH INHIBITION

(71) Applicant: THE REGENTS OF THE UNIVERSITY OF CALIFORNIA, Oakland, CA (US)

(72) Inventors: David Cheresh, Encinitas, CA (US); Laetitia Seguin, San Diego, CA (US); Sudarshan Anand, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/325,288

(22) Filed: Jul. 7, 2014

(65) Prior Publication Data
US 2016/0015709 A1    Jan. 21, 2016

Related U.S. Application Data

(63) Continuation-in-part of application No. PCT/US2013/035492, filed on Apr. 5, 2013.
(Continued)

(51) Int. Cl.
| | |
|---|---|
| *A61K 31/517* | (2006.01) |
| *A61K 38/05* | (2006.01) |
| *B65D 75/36* | (2006.01) |
| *G01N 33/574* | (2006.01) |
| *A61K 45/06* | (2006.01) |
| *A61K 31/454* | (2006.01) |
| *A61K 33/24* | (2006.01) |
| *G01N 33/50* | (2006.01) |
| *A61K 31/337* | (2006.01) |
| *A61K 31/437* | (2006.01) |
| *A61K 31/5377* | (2006.01) |
| *A61K 31/69* | (2006.01) |
| *A61K 31/496* | (2006.01) |
| *A61K 31/506* | (2006.01) |
| *A61K 31/519* | (2006.01) |
| *A61K 31/715* | (2006.01) |
| *A61K 31/4985* | (2006.01) |

(Continued)

(52) U.S. Cl.
CPC ........ *G01N 33/5011* (2013.01); *A61K 31/337* (2013.01); *A61K 31/437* (2013.01); *A61K 31/454* (2013.01); *A61K 31/496* (2013.01); *A61K 31/4985* (2013.01); *A61K 31/506* (2013.01); *A61K 31/517* (2013.01); *A61K 31/519* (2013.01); *A61K 31/5377* (2013.01); *A61K 31/69* (2013.01); *A61K 31/7068* (2013.01); *A61K 31/715* (2013.01); *A61K 33/24* (2013.01); *A61K 38/05* (2013.01); *A61K 38/12* (2013.01); *A61K 45/06* (2013.01); *B65D 75/002* (2013.01); *B65D 75/36* (2013.01); *G01N 33/5008* (2013.01); *G01N 33/57492* (2013.01); *G01N 33/57496* (2013.01); *G01N 2333/4724* (2013.01); *G01N 2333/485* (2013.01); *G01N 2333/70557* (2013.01); *G01N 2333/914* (2013.01); *G01N 2800/52* (2013.01)

(58) Field of Classification Search
CPC .... A61K 31/517; A61K 31/454; A61K 38/05; A61K 31/4985; A61K 31/7068; A61K 33/24; A61K 38/12; A61K 45/06; G01N 33/57496; G01N 33/57492; G01N 2333/914; G01N 2333/70557; B65D 75/002; B65D 75/36
USPC ........ 424/133.1, 143.1, 174.1; 435/29, 7.23; 514/249, 262.1, 266.4, 7.6
See application file for complete search history.

(56) References Cited

U.S. PATENT DOCUMENTS

2004/0023925 A1 * 2/2004 Chang .................... A61K 31/00
514/54
2006/0142297 A1   6/2006 Barge
(Continued)

OTHER PUBLICATIONS

Glossary of medical education terms, Institute of International Medical Education. http://www.iime.org/glossary.htm Accessed in Mar. 2013.*
Wheeler et al. Understanding resistance to EgFR inhibitors—impact on future treatment strategies. Nat. Rev. Clin. Oncol. 7, 493-507 (2010).*
(Continued)

*Primary Examiner* — Clinton Brooks
*Assistant Examiner* — Yih-Horng Shiao
(74) *Attorney, Agent, or Firm* — Greer, Burns & Crain, Ltd.; Gregory P. Einhorn

(57) ABSTRACT

In alternative embodiments, the invention provides compositions and methods for overcoming or diminishing or preventing Growth Factor Inhibitor resistance in a cell, or, a method for increasing the growth-inhibiting effectiveness of a Growth Factor inhibitor on a cell, or, a method for re-sensitizing a cell to a Growth Factor Inhibitor, comprising for example, administration of a combination of a TBK1 inhibitor and an RTK inhibitor. In alternative embodiments, the cell is a tumor cell, a cancer cell or a dysfunctional cell. In alternative embodiments, the invention provides compositions and methods for determining: whether an individual or a patient would benefit from or respond to administration of a Growth Factor Inhibitor, or, which individuals or patients would benefit from a combinatorial approach comprising administration of a combination of: at least one growth factor and at least one compound, composition or formulation used to practice a method of the invention, such as an NFKB inhibitor, such as a lenalidomide or a REV-LIMID™, or IKK inhibitor; or an inhibitor of Galectin-3.

14 Claims, 41 Drawing Sheets

Related U.S. Application Data

(60) Provisional application No. 61/672,236, filed on Jul. 16, 2012, provisional application No. 61/843,417, filed on Jul. 7, 2013.

(51) Int. Cl.
  *A61K 31/7068* (2006.01)
  *A61K 38/12* (2006.01)
  *B65D 75/00* (2006.01)

(56) References Cited

U.S. PATENT DOCUMENTS

| | | |
|---|---|---|
| 2007/0254893 A1 | 11/2007 | Green |
| 2009/0048205 A1 | 2/2009 | Meyer et al. |
| 2010/0004257 A1 | 1/2010 | Haura |
| 2010/0092475 A1 | 4/2010 | Johns et al. |

OTHER PUBLICATIONS

Suda et al. Epithelial to Mesenchymal Transition in an Epidermal Growth Factor Receptor-Mutant Lung Cancer Cell Line with Acquired Resistance to Erlotinib. J Thorac Oncol. 2011;6: 1152-1161.*

MacKinnon et al. Regulation of Transforming Growth Factor-b1-driven Lung Fibrosis by Galectin-3. Am J Respir Crit Care Med vol. 185, Iss. 5, pp. 537-546, Mar. 1, 2012. Originally Published in Press as DOI: 10.1164/rccm.201106-0965OC on Nov. 17, 2011.*

Rao et al. siRNA vs. shRNA: Similarities and differences. Advanced Drug Delivery Reviews 61 (2009) 746-759.*

Choi, Sung Hee, International Search Report and Written Opinion, PCT/US2013/035492, Korean Intellectual Property Office, Date of Mailing: Jul. 26, 2013.

Moon, Kihwan, International Preliminary Report on Patentability and Written Opinion, PCT/US2013/035492, The International Bureau of WIPO, Date of Mailing: Oct. 16, 2014.

\* cited by examiner

Seguin et al., Figure 2
FIG. 2A
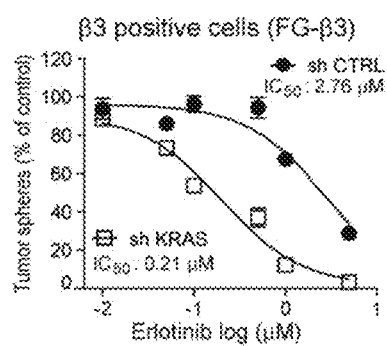
FIG. 2B
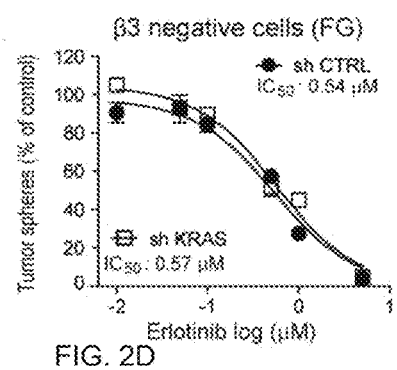
FIG. 2C
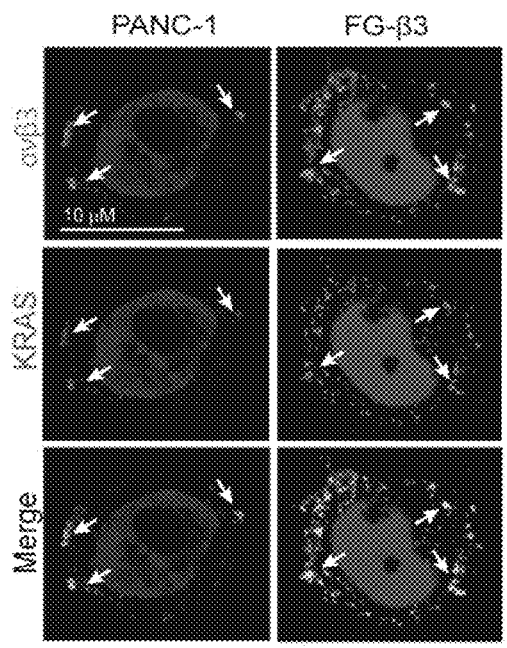
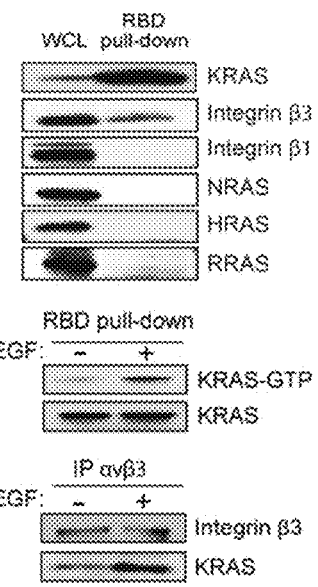
FIG. 2E

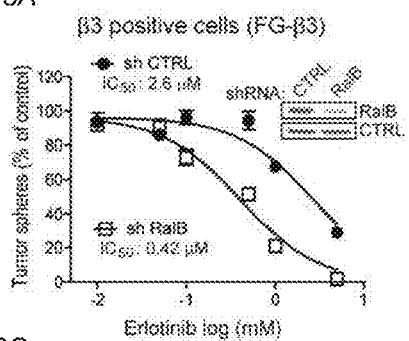
FIG. 3A
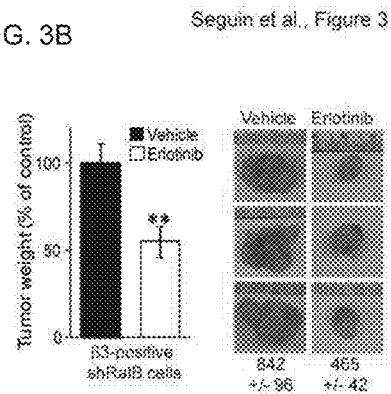
FIG. 3B
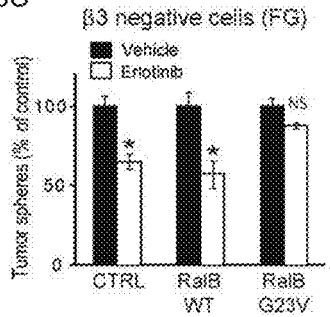
FIG. 3C
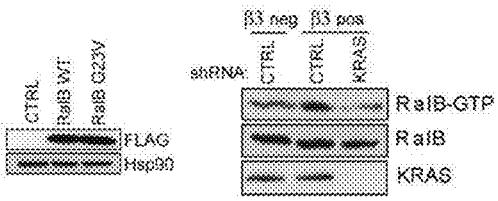
FIG. 3D
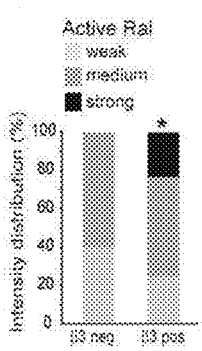
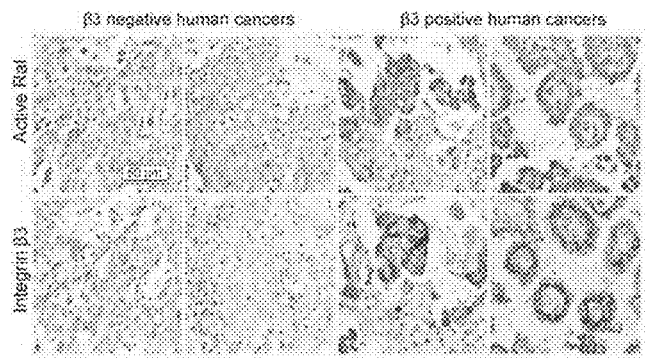
FIG. 3E Seguin et al., Figure 4

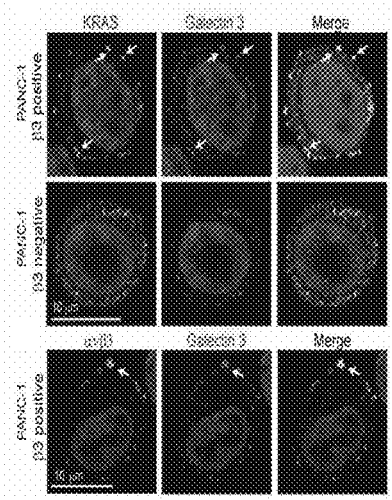
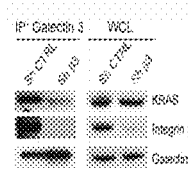
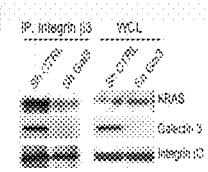
FIG. 8A  FIG. 8B  FIG. 8C  FIG. 8D

Seguin et al., Supplementary Figure 5

Seguin et al., Figure 1
FIG. 12A
FIG. 12B
FIG. 12C
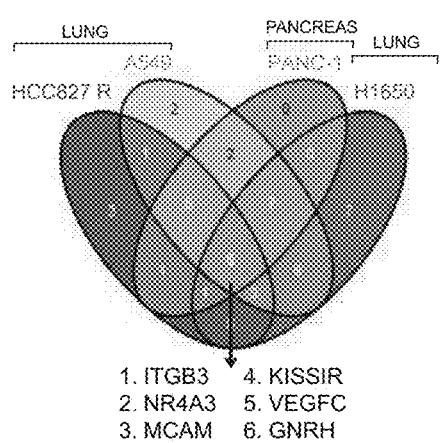
1. ITGB3  4. KISSIR
2. NR4A3  5. VEGFC
3. MCAM   6. GNRH
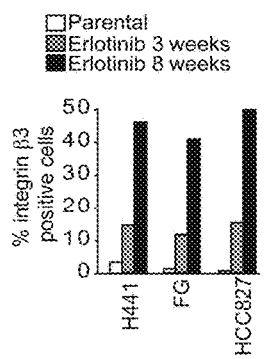
FIG. 12D
Battle Trial lung cancers
FIG. 12E
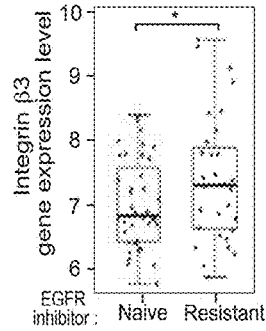
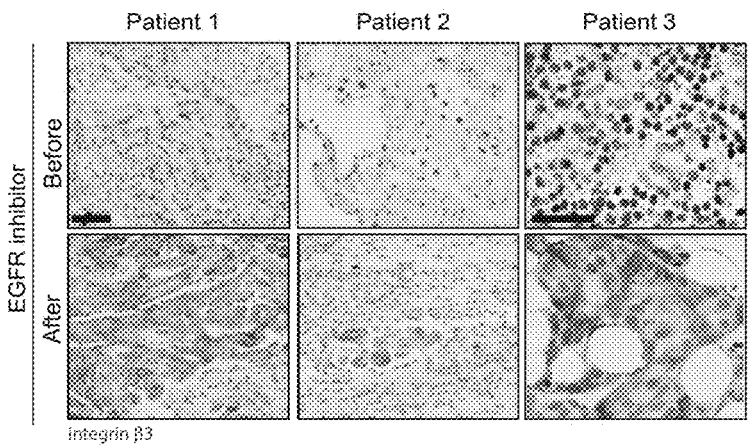
FIG. 12F
Erlotinib treatment in vitro
FIG. 12G
Erlotinib treatment in vivo
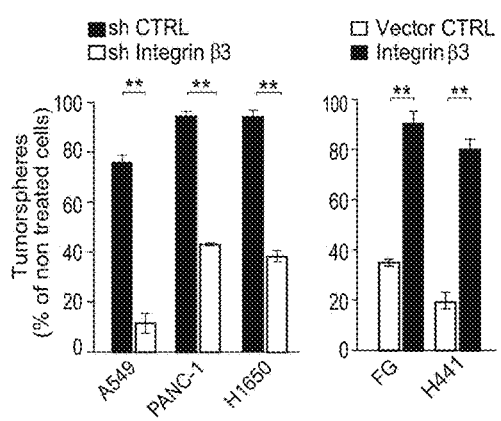
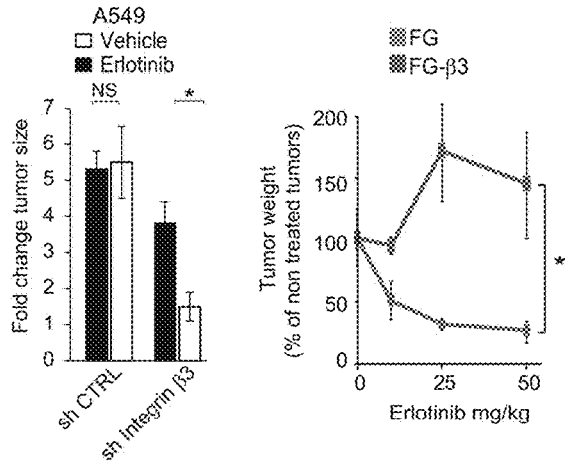

Seguin et al., Figure 2

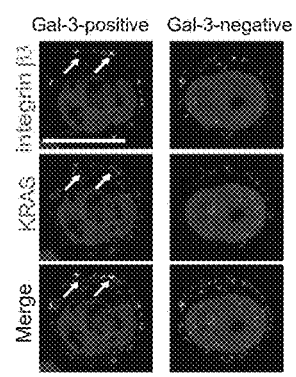
FIG. 13G
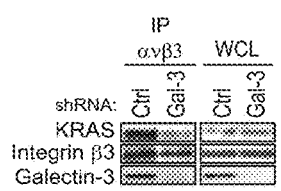
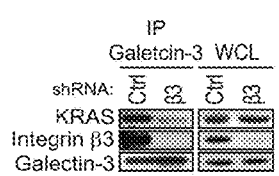
FIG. 13H
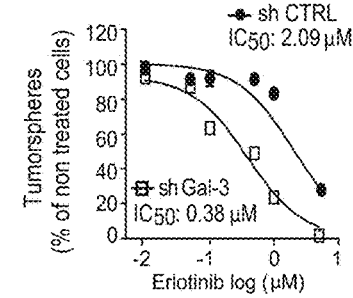
FIG. 13I

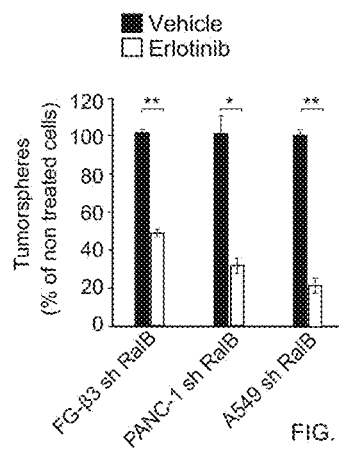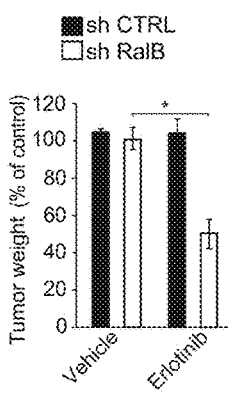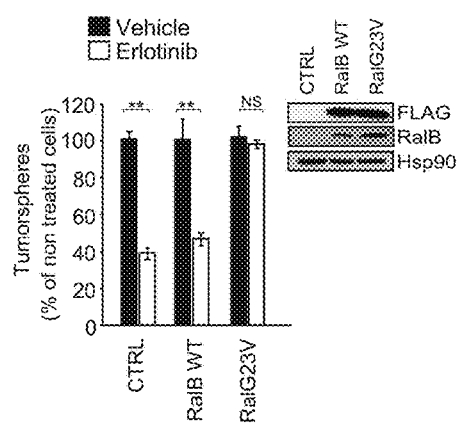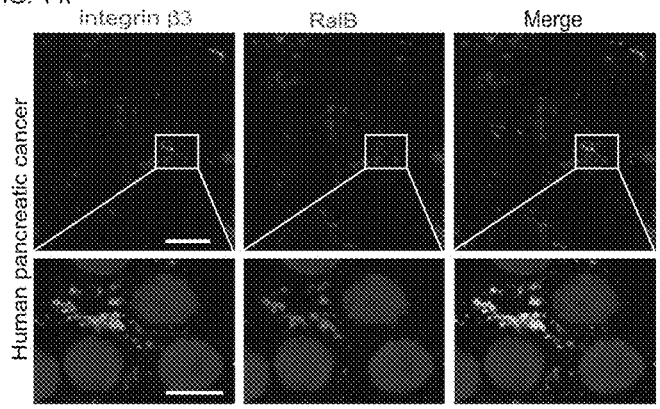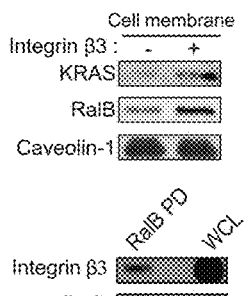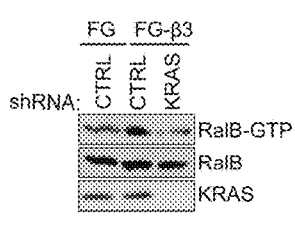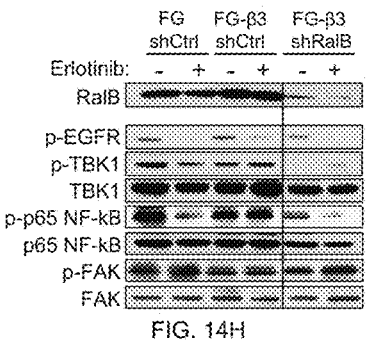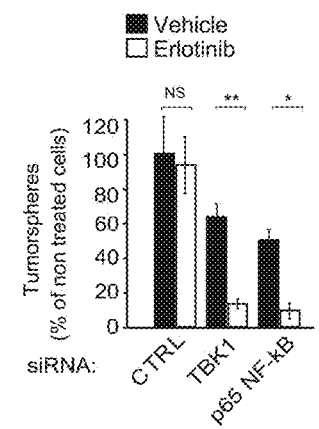

Integrin β3 drives a tumor switch from EGFR to KRAS dependency leading to EGFR inhibitor resistance.

Seguin et al., Supplementary Fig. S1
FIG. 16A
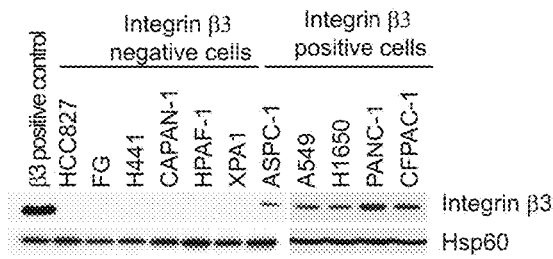
FIG. 16B
Lung cancer xenografts (HCC827)
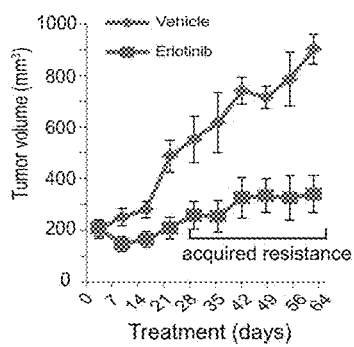
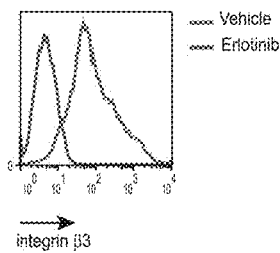
FIG. 16C
Orthotopic lung cancer xenografts (H441)
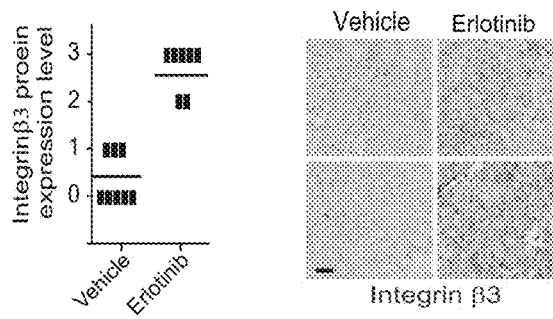
Orthotopic pancreas cancer xenografts (FG)
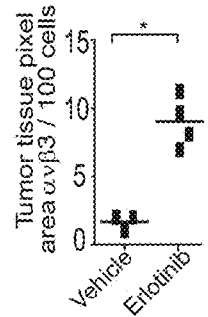

Seguin et al., Supplementary Fig. S2

Seguin et al., Supplementary Fig. S3

Seguin et al., Supplementary Fig. S4

Seguin at al., Supplementary Fig. S5

PANC-1

BxPC-3-β3

Seguin et al., Supplementary Fig. S6
FIG. 21A
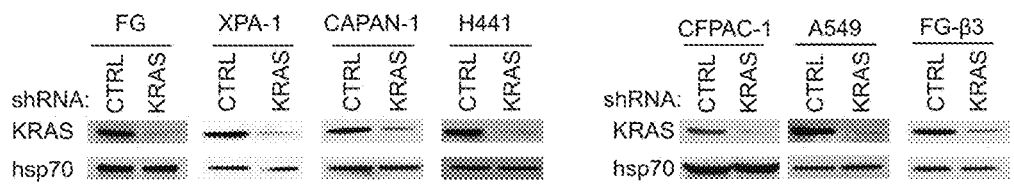
FIG. 21B
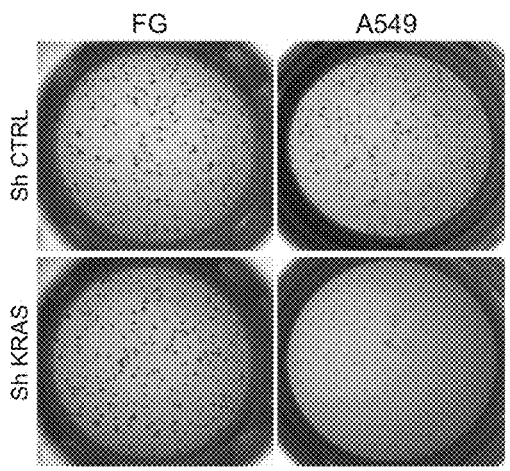
FIG. 21C
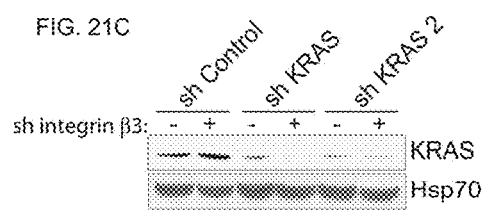
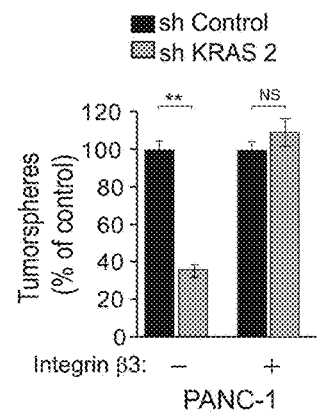
FIG. 21D Seguin et al., Supplementary Fig. S7

Seguin et al., Supplementary Fig. S9

Seguin et al., Supplementary Fig. S10

FIG. 26

Seguin et al., Supplementary Table S1

| Gene Symbol | Fold change | | | |
|---|---|---|---|---|
| | PANC-1 | A549 | H1650 | HCC827R |
| ITGB3-Hs00173978_m1 | 696.78 | 460.88 | 93.38 | 4.86 |
| SERPINE1-Hs00167155_m1 | 327.11 | 175.33 | 0.71 | 7.45 |
| KISS1R-Hs00261399_m1 | 117.88 | 10.94 | 2.75 | 2.57 |
| MCAM-Hs00174838_m1 | 115.76 | 4.23 | 101.85 | 4.26 |
| RET-Hs00240887_m1 | 111.22 | 14.07 | 63.12 | 2.12 |
| FGF2-Hs00266645_m1 | 95.03 | 538.31 | 1012.13 | 0.88 |
| WISP1-Hs00365573_m1 | 55.94 | 4.05 | 7.76 | 2.12 |
| CCL7-Hs00171147_m1 | 30.18 | 4.05 | 7.76 | 2.12 |
| NR4A3-Hs00235001_m1 | 28.49 | 571.82 | 222.59 | 7.24 |
| CD44-Hs00153304_m1 | 28.10 | 26.93 | 15.19 | 1.78 |
| CXCL12-Hs00171022_m1 | 23.66 | 10.99 | 23.79 | 2.12 |
| HGF-Hs00300159_m1 | 21.19 | 32.18 | 56.52 | 2.12 |
| MTSS1-Hs00207341_m1 | 20.78 | 11.02 | 341.52 | 0.37 |
| S100A4-Hs00243202_m1 | 19.67 | 25.08 | 0.19 | 131.99 |
| MMP2-Hs00234422_m1 | 17.39 | 12.97 | 290.44 | 2.12 |
| DCC-Hs00180437_m1 | 14.12 | 382.69 | 7.76 | 2.12 |
| TP53-Hs00153349_m1 | 12.73 | 14.05 | 0.87 | 0.85 |
| IL1B-Hs00174097_m1 | 12.12 | 22.12 | 23.09 | 1.23 |
| NF2-Hs00738978_m1 | 8.37 | 3.29 | 5.18 | 0.31 |
| LAMB1-Hs00158620_m1 | 8.02 | 55.11 | 31.26 | 1.41 |
| ERBB2-Hs00170433_m1 | 7.93 | 2.67 | 5.36 | 0.89 |
| HRAS-Hs00610483_m1 | 6.46 | 9.21 | 1.11 | 3.19 |
| NCAM1-Hs00169851_m1 | 4.80 | 33.12 | 2.76 | 2.12 |
| HTATIP2-Hs00185131_m1 | 3.88 | 10.91 | 0.77 | 3.19 |
| EPHB2-Hs00362096_m1 | 3.84 | 14.77 | 4.02 | 0.74 |
| PSCA-Hs00194665_m1 | 3.57 | 1.27 | 13.66 | 15.06 |
| NME1-Hs02621161_s1 | 3.52 | 2.79 | 1.15 | 1.67 |
| VEGFC-Hs00153458_m1 | 3.44 | 7.94 | 7.84 | 19.66 |
| GNRH1-Hs00171272_m1 | 2.73 | 8.12 | 9.45 | 3.58 |
| PTEN-Hs01920652_s1 | 2.36 | 1.96 | 0.03 | 1.30 |
| SMAD2-Hs00183425_m1 | 2.33 | 2.50 | 2.40 | 2.19 |
| MMP14-Hs01037009_g1 | 2.07 | 0.00 | 0.00 | 113.24 |
| RB1-Hs00153108_m1 | 2.07 | 2.49 | 1.31 | 2.08 |
| RHOC-Hs00733980_m1 | 1.92 | 1.88 | 2.03 | 0.18 |
| IGF1-Hs00153126_m1 | 1.84 | 30.89 | 7.76 | 0.25 |
| TSHR-Hs00174910_m1 | 1.84 | 4.05 | 7.76 | 2.12 |
| CTBP1-Hs00179922_m1 | 1.82 | 0.85 | 1.58 | 1.30 |
| TGFB1-Hs99999918_m1 | 1.82 | 5.03 | 2.21 | 1.36 |
| MTA2-Hs00191018_m1 | 1.50 | 1.58 | 0.74 | 0.82 |
| FAT-Hs00170627_m1 | 1.35 | 0.67 | 2.37 | 0.69 |
| MTA1-Hs00183042_m1 | 1.29 | 2.59 | 2.26 | 2.31 |
| RBL2-Hs00180562_m1 | 1.29 | 2.00 | 8.23 | 4.11 |

FIG. 27

| | | | | |
|---|---|---|---|---|
| SMAD4-Hs00232068_m1 | 1.28 | 2.54 | 1.49 | 0.61 |
| CTNNA1-Hs00426996_m1 | 1.18 | 0.93 | 1.76 | 0.35 |
| CTSK-Hs00166156_m1 | 1.16 | 1.04 | 2.29 | 2.46 |
| TIMP2-Hs00234278_m1 | 1.09 | 2.08 | 10.26 | 1.57 |
| KRAS-Hs00270666_m1 | 1.07 | 0.58 | 0.66 | 0.90 |
| TCF20-Hs00390028_m1 | 1.05 | 1.02 | 1.09 | 1.89 |
| CASP8-Hs01018151_m1 | 1.03 | 0.83 | 2.01 | 1.45 |
| CD82-Hs00174463_m1 | 1.00 | 0.22 | 9.89 | 2.03 |
| SSTR2-Hs00265624_s1 | 0.96 | 1.32 | 0.16 | 4.63 |
| APC-Hs00181051_m1 | 0.95 | 1.93 | 3.11 | 1.60 |
| BRMS1-Hs00363036_m1 | 0.94 | 1.36 | 0.49 | 1.92 |
| TGFBR2-Hs00559661_m1 | 0.94 | 3.18 | 3.22 | 1.02 |
| MGAT5-Hs00159136_m1 | 0.90 | 0.85 | 1.68 | 0.83 |
| MMP1-Hs00233958_m1 | 0.80 | 0.12 | 33.50 | 6.56 |
| MYC-Hs00153408_m1 | 0.72 | 1.59 | 0.40 | 1.83 |
| PNN-Hs00170192_m1 | 0.69 | 2.08 | 2.07 | 1.07 |
| FGFR4-Hs00242558_m1 | 0.66 | 5.57 | 0.34 | 1.75 |
| CEACAM1-Hs00236077_m1 | 0.60 | 0.08 | 42.13 | 0.45 |
| TPBG-Hs00272649_s1 | 0.52 | 0.99 | 1.22 | 0.90 |
| RBL1-Hs00765707_m1 | 0.49 | 1.90 | 2.26 | 0.32 |
| MMP3-Hs00968305_m1 | 0.48 | 1.06 | 17.55 | 2.12 |
| KISS1-Hs00158486_m1 | 0.42 | 7.77 | 1.77 | 3.18 |
| MET-Hs00179845_m1 | 0.40 | 1.67 | 1.71 | 1.52 |
| MMP7-Hs00159163_m1 | 0.37 | 217.80 | 0.19 | 1.00 |
| ETV4-Hs00385910_m1 | 0.36 | 1.72 | 0.00 | 1.02 |
| CXCR4-Hs00607978_s1 | 0.34 | 0.54 | 0.05 | 68.58 |
| VEGFA-Hs00900054_m1 | 0.31 | 0.47 | 0.87 | 0.97 |
| HPSE-Hs00180737_m1 | 0.30 | 0.64 | 2.67 | 0.78 |
| CDH1-Hs00170423_m1 | 0.28 | 2.74 | 13.50 | 1.02 |
| TIMP1-Hs00171558_m1 | 0.27 | 1.12 | 1.33 | 1.55 |
| FXYD5-Hs00204319_m1 | 0.25 | 1.50 | 22.13 | 2.20 |
| DAPK1-Hs00234480_m1 | 0.24 | 120.55 | 39.04 | 2.47 |
| SNCG-Hs00268306_m1 | 0.18 | 1.25 | 12.37 | 17.75 |
| TNFSF10-Hs00234356_m1 | 0.17 | 0.77 | 1.11 | 4.05 |
| SET-Hs00853870_g1 | 0.16 | 0.27 | 1.37 | 0.65 |
| MMP9-Hs00234579_m1 | 0.16 | 0.13 | 0.72 | 1.87 |
| FN1-Hs00365058_m1 | 0.15 | 36.58 | 13.82 | 0.90 |
| MMP10-Hs00233987_m1 | 0.11 | 0.25 | 7.73 | 2.87 |
| TWIST1-Hs00361186_m1 | 0.08 | 13.80 | 173.29 | 15.20 |
| PECAM1-Hs00169777_m1 | 0.07 | 0.16 | 19.20 | 2060.54 |
| TACSTD1-Hs00158980_m1 | 0.06 | 0.03 | 0.62 | 0.78 |
| PTGS2-Hs00153133_m1 | 0.05 | 48.57 | 0.22 | 11.74 |
| TIAM1-Hs00180075_m1 | 0.05 | 0.35 | 4.47 | 1.92 |
| TIMP4-Hs00162784_m1 | 0.05 | 3.76 | 1.86 | 0.68 |
| IL18-Hs00155517_m1 | 0.03 | 0.06 | 67.29 | 4.99 |
| SERPINB5-Hs00184728_m1 | 0.02 | 0.01 | 5.99 | 5.00 |
| LYPD3-Hs00205233_m1 | 0.02 | 0.03 | 0.06 | 193.85 |

FIG. 28

| | | | | |
|---|---|---|---|---|
| SYK-Hs00374292_m1 | 0.00 | 0.67 | 0.02 | 0.39 |
| TMPRSS4-Hs00854071_mH | 0.00 | 0.03 | 0.13 | 0.60 |
| CDKN2A-Hs00233365_m1 | 0.00 | 0.06 | 0.00 | 1.84 |

FIG. 29

Seguin et al., Supplementary table 2

| KRAS mutational status ||| 
|---|---|---|
| Origin | Cell line | KRAS mutation |
| Lung | HCC827 | - |
| Pancreas | FG | G12D |
| Lung | H441 | G12V |
| Pancreas | CAPAN-1 | G12V |
| Pancreas | HPAF-II | - |
| Pancreas | XPA-1 | - |
| Lung | H1650 | - |
| Pancreas | ASPC-1 | G12D |
| Lung | A549 | G12S |
| Pancreas | CFPAC-1 | G12V |
| Pancreas | PANC-1 | G12D |

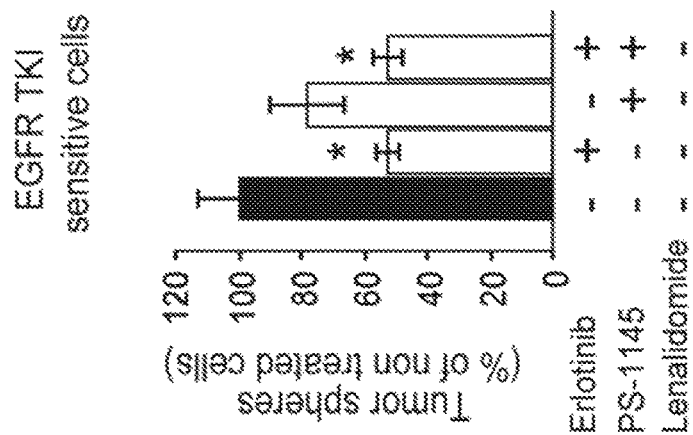
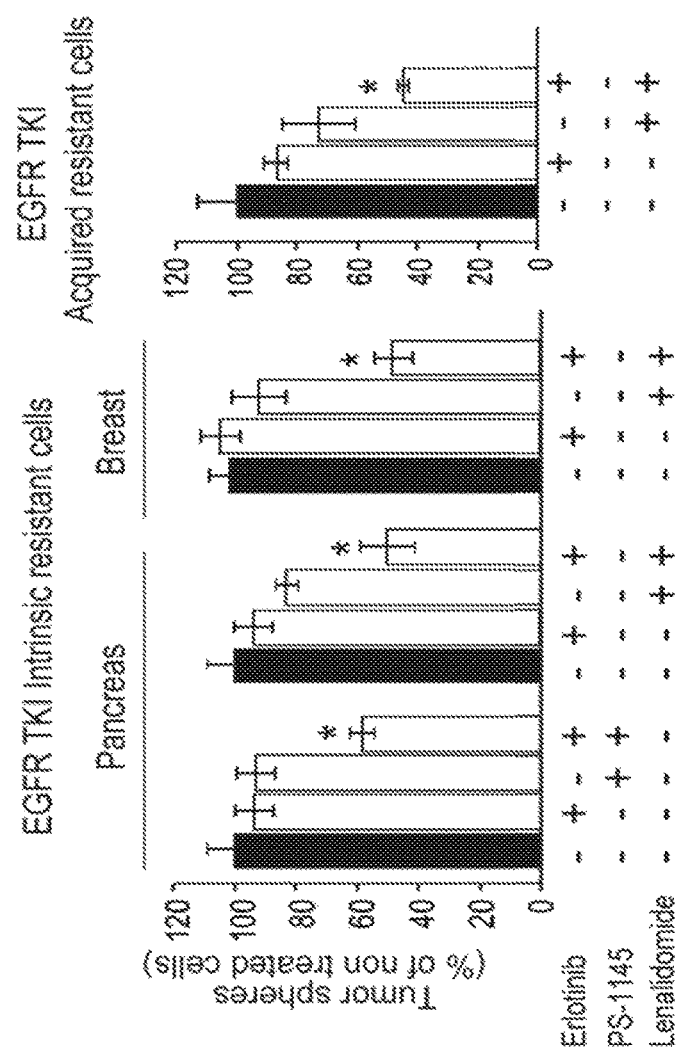

FIG. 32A
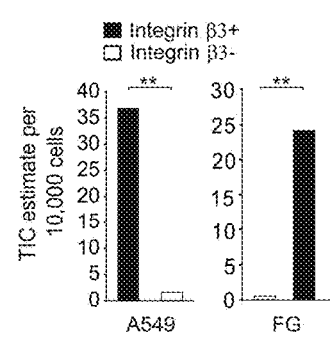
FIG. 32B A549
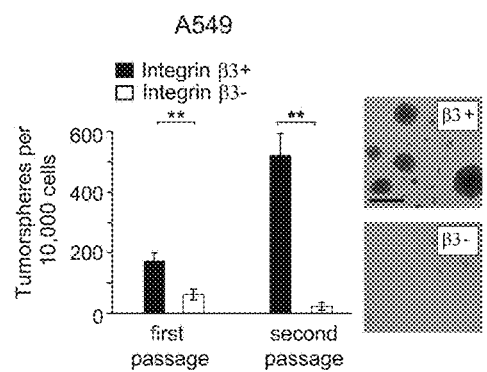
Seguin et al., Figure 1
Example 3
FIG. 32C PANC-1
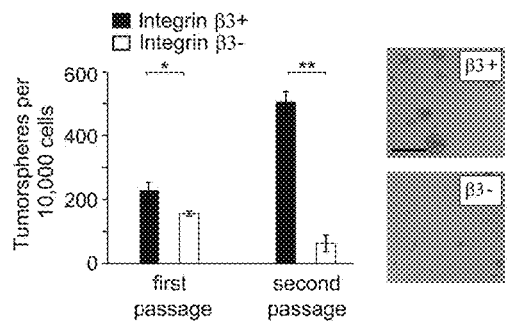
FIG. 32D FG
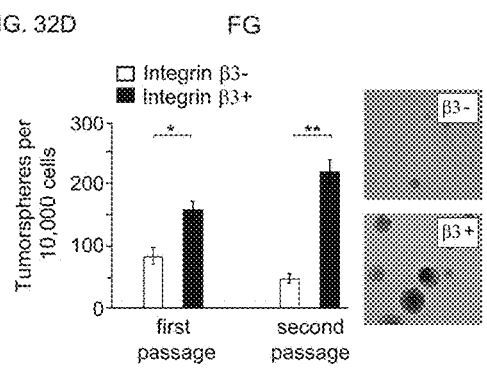

Seguin et al., Figure 2
Example 3

FIG. 33F HCC827 EGFR E746_A750del 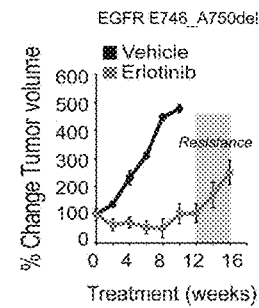

FIG. 33H Human adenocarcinoma EGFR mutant (L858R mutation) 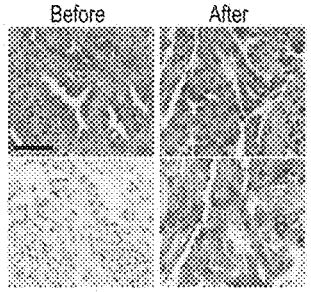

FIG. 34A
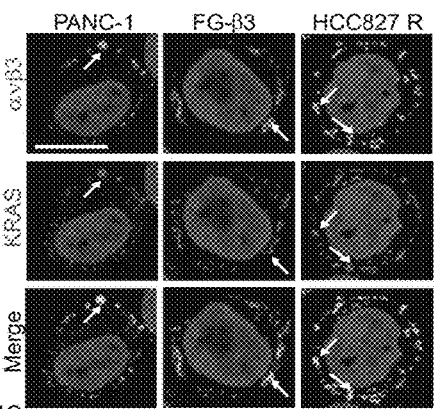
FIG. 34B    Seguin et al., Figure 3
Example 3
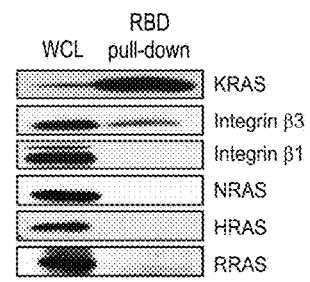
FIG. 34C
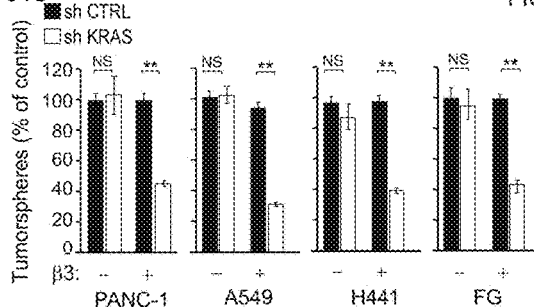
FIG. 34D
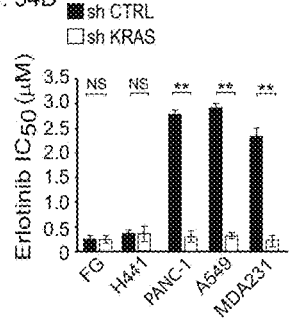
FIG. 34E
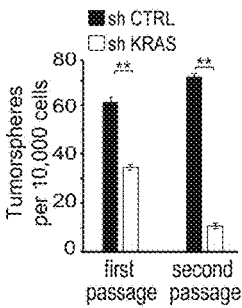
FIG. 34F
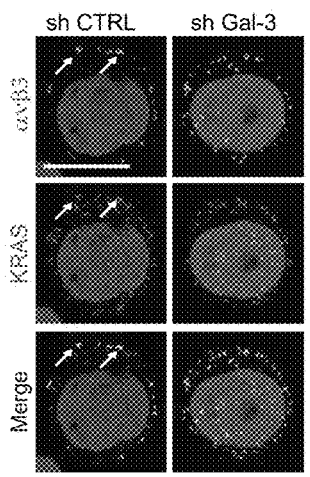
FIG. 34G
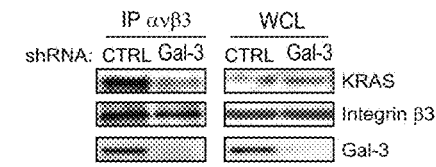
FIG. 34H
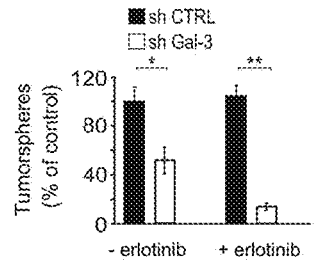
FIG. 34I
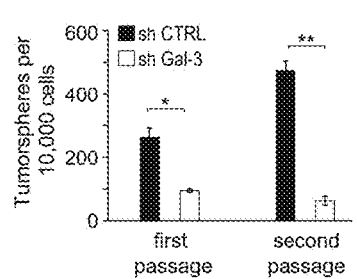

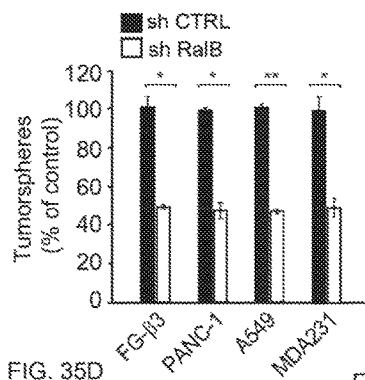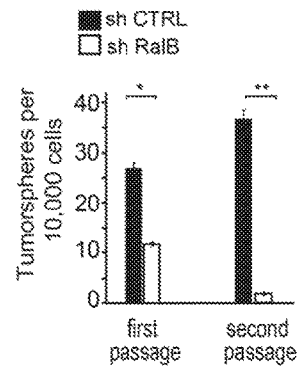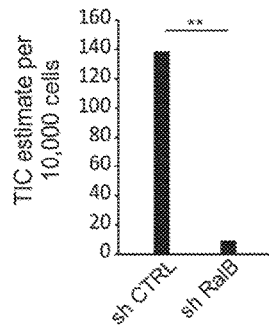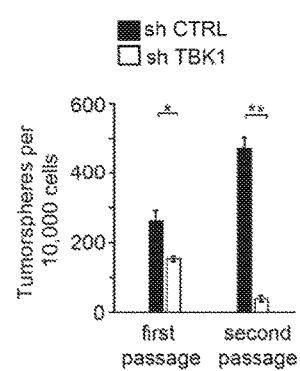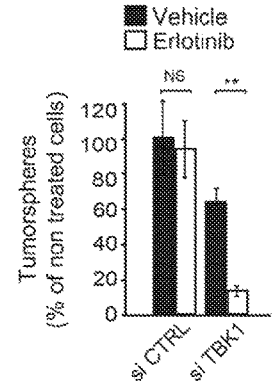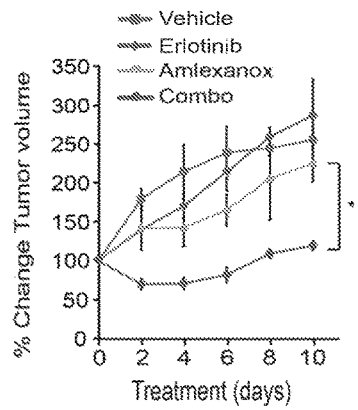
FIG. 35A FIG. 35B FIG. 35C FIG. 35D FIG. 35E FIG. 35F FIG. 35G FIG. 35H FIG. 35I

FIG. 36A

| Cells | No. cells per injection | No. tumors / No. injections | LTICs frequency (95% CI) | Enrichment factor (x) | P value |
|---|---|---|---|---|---|
| FG | 1000000 | 8/8 | 1/21249 (54628-8265) | 1 | 1.86E-07 |
| | 100000 | 7/8 | | | |
| | 10000 | 4/7 | | | |
| | 1000 | 3/8 | | | |
| | 100 | 1/8 | | | |
| FGβ3 | 1000000 | 4/4 | 1/418 (1259-139) | 50.83 | |
| | 100000 | 4/4 | | | |
| | 10000 | 3/3 | | | |
| | 1000 | 4/4 | | | |
| | 100 | 1/4 | | | |

FIG. 36B — Seguin et al., Supplementary Fig. S1 Example 3

| Cells | No. cells per injection | No. tumors / No. injections | LTICs frequency (95% CI) | Enrichment factor (x) | P value |
|---|---|---|---|---|---|
| A549 | 1000000 | 6/6 | 1/271 (639-115) | 1 | 1.98E-09 |
| | 100000 | 6/6 | | | |
| | 10000 | 8/8 | | | |
| | 1000 | 7/8 | | | |
| | 100 | 5/8 | | | |
| A549 shβ3 | 1000000 | 2/2 | 1/6195 (13365-2872) | 0.043 | |
| | 100000 | 6/6 | | | |
| | 10000 | 5/8 | | | |
| | 1000 | 3/8 | | | |
| | 100 | 1/8 | | | |

FIG. 36C

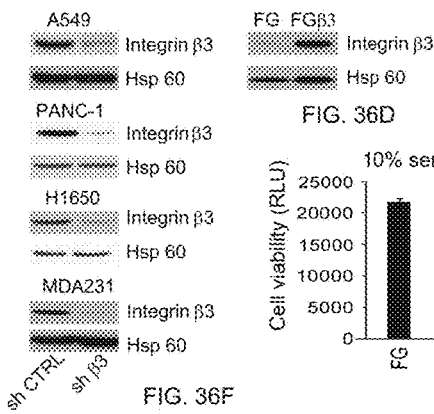

FIG. 36D

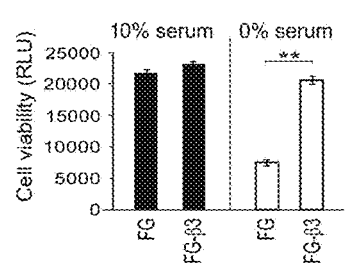

FIG. 36E

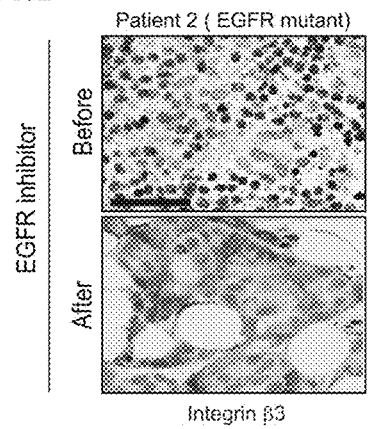

FIG. 36F

| Cells | No. cells per injection | No. tumors / No. injections | LTICs frequency (95% CI) | Enrichment factor (x) | P value |
|---|---|---|---|---|---|
| HCC827 Parental | 1000000 | 2/2 | 1/23699 (1/66640-1/8428) | 1 | |
| | 100000 | 5/5 | | | |
| | 10000 | 2/6 | | | |
| | 1000 | 0/5 | | | |
| | 100 | 0/5 | | | |
| | 10 | 0/6 | | | |
| HCC827 Resistant | 1000000 | 2/2 | 1/153.6 (1/443-1/53.5) | 153.989604 | 1.32E-10 |
| | 100000 | 5/5 | | | |
| | 10000 | 6/6 | | | |
| | 1000 | 3/5 | | | |
| | 100 | 4/5 | | | |
| | 10 | 3/6 | | | |
| HCC827 Resistant integrin β3- | 1000000 | 2/2 | 1/1062 (1/2852-1/395.9) | 22.3154426 | 5.79E-05 |
| | 100000 | 5/5 | | | |
| | 10000 | 4/4 | | | |
| | 1000 | 4/6 | | | |
| | 100 | 0/6 | | | |
| | 10 | 0/6 | | | |
| HCC827 Resistant integrin β3+ | 1000000 | 2/2 | 1/45.3 (1/110-1/18.8) | 523.156733 | 2.05E-19 |
| | 100000 | 5/5 | | | |
| | 10000 | 4/4 | | | |
| | 1000 | 6/6 | | | |
| | 100 | 5/6 | | | |
| | 10 | 2/6 | | | |

FIG. 36G

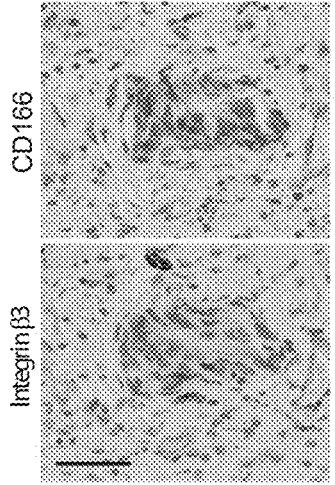

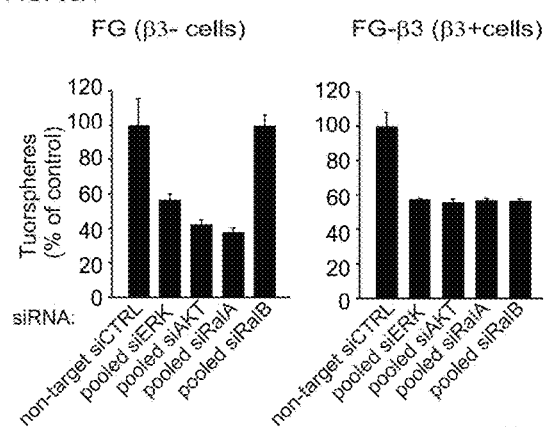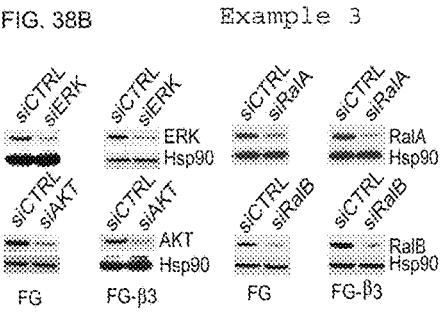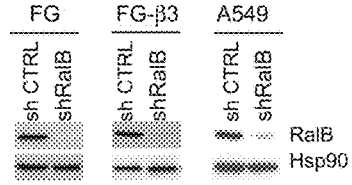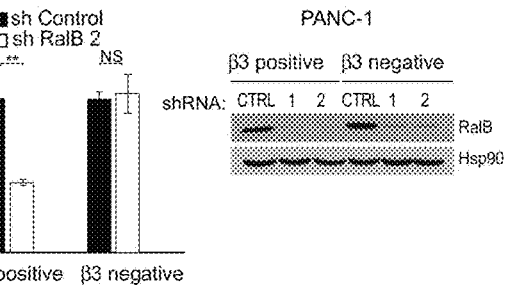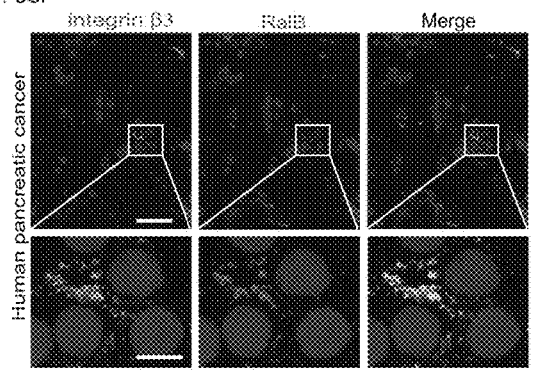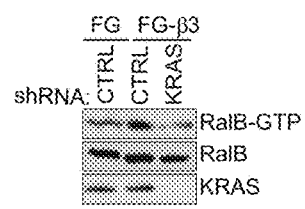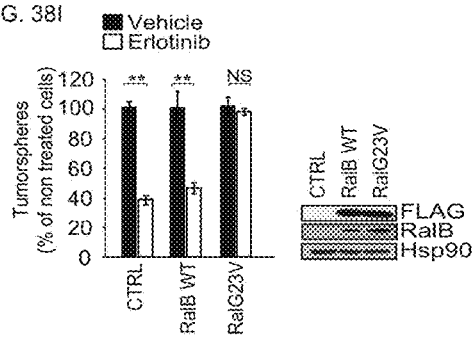

Seguin et al., Supplementary Fig. S4
Example 3

Depletion of TBK1 overcomes erlotinib resistance in KRAS mutant cells

COMPOSITIONS AND METHODS FOR TREATING CANCER AND DISEASES AND CONDITIONS RESPONSIVE TO CELL GROWTH INHIBITION

RELATED APPLICATIONS

This application is a continuation in part (CIP) of Patent Convention Treaty (PCT) International Application Serial No: PCT/US2013/035492, filed Apr. 5, 2013, now pending, which claims benefit of priority to International Application Serial No: PCT/US2012/040390, filed Jun. 2, 2012, and which also claims benefit of priority to U.S. Provisional Patent Application Ser. No. 61/672,236, filed Jul. 16, 2012, and U.S. Ser. No. 61/620,725, filed Apr. 5, 2012. This application also claims the benefit of priority under 35 U.S.C. §119(e) of U.S. Provisional Patent Application Ser. No. 61/843,417, filed Jul. 7, 2013. The aforementioned applications are expressly incorporated herein by reference in their entirety and for all purposes.

GOVERNMENT RIGHTS

This invention was made with government support under grant numbers CA045726, CA050286, CA095262, HL057900, and HL103956, awarded by the National Institutes of Health (NIH). The government has certain rights in the invention.

TECHNICAL FIELD

This invention generally relates to cell and molecular biology, diagnostics and oncology. In alternative embodiments, the invention provides compositions and methods for overcoming or diminishing or preventing Growth Factor Inhibitor resistance in a cell, or, a method for increasing the growth-inhibiting effectiveness of a Growth Factor inhibitor on a cell, or, a method for re-sensitizing a cell to a Growth Factor Inhibitor, or, sensitizing a tumor to a drug, wherein optionally the drug is an erlotinib or a lapatinib, or, sensitizing a tumor that is resistant to a cancer drug, comprising for example, administration of a combination of a TBK1 inhibitor and an RTK inhibitor. In alternative embodiments, the cell is a tumor cell, a cancer cell, a cancer stem cell or a dysfunctional cell. In alternative embodiments, the invention provides compositions and methods for determining: whether an individual or a patient would benefit from or respond to administration of a Growth Factor Inhibitor, or, which individuals or patients would benefit from a combinatorial approach comprising administration of a combination of: at least one growth factor and at least one compound, composition or formulation used to practice a method of the invention, such as an NFKB (nuclear factor kappa-light-chain-enhancer of activated B cells, or NF-κB) inhibitor, such as a lenalidomide or a REVLIMID™, or an IκB kinase (IKK) inhibitor; or an inhibitor of Galectin-3.

BACKGROUND

Growth factor inhibitors have been used to treat many cancers including pancreatic, breast, lung and colorectal cancers. However, resistance to growth factor inhibitors has emerged as a significant clinical problem.

Tumor resistance to targeted therapies occurs due to a combination of stochastic and instructional mechanisms. Mutation/amplification in tyrosine kinase receptors or their downstream effectors account for the resistance of a broad range of tumors. In particular, oncogenic KRAS, the most commonly mutated oncogene in human cancer, has been linked to EGFR inhibitor resistance. However, in lung and pancreatic carcinomas, recent studies suggest that oncogenic KRAS is not sufficient to account for EGFR inhibitor resistance indicating that other factor(s) might control this process.

SUMMARY

In alternative embodiments, the invention provides methods for:
overcoming or diminishing or preventing a Growth Factor Inhibitor (GFI) resistance in a cell, or
increasing the growth-inhibiting effectiveness of a Growth Factor inhibitor on a cell, or
sensitizing, increasing sensitivity to or re-sensitizing a cell to a Growth Factor Inhibitor (GFI), or
sensitizing, increasing sensitivity to or re-sensitizing a dysfunctional cell, a tumor or cancer to a drug,
  wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide,
sensitizing, increasing sensitivity to or re-sensitizing a tumor that is resistant to a cancer or anti-tumor drug, or
reversing a tumor cell, a cancer cell, a cancer stem cell or a dysfunctional cell initiation or self-renewal capacity,
  wherein optionally the cell is a tumor cell, a cancer cell, a cancer stem cell, or a dysfunctional cell,
the method comprising:
(a)(1) providing at least one compound, composition or formulation comprising or consisting of:
(i) an inhibitor or depleter of integrin $\alpha_v\beta_3$ (anb3), or
  an inhibitor of integrin $\alpha_v\beta_3$ (anb3) protein activity, or
  an inhibitor of the formation or activity of an integrin anb3/RalB signaling complex, or
  an inhibitor of the formation or signaling activity of an integrin $\alpha_v\beta_3$ (anb3)/RalB/NFkB signaling axis,
  wherein optionally the inhibitor of integrin $\alpha_v\beta_3$ protein activity is an allosteric inhibitor of integrin $\alpha_v\beta_3$ protein activity;
(ii) an inhibitor or depleter of a RalB protein or an inhibitor of a RalB protein activation, or
  an inhibitor or depleter of the recruitment of KRAS/RalB to the plasma membrane or the association of KRAS to RalB,
  wherein optionally the inhibitor is an allosteric inhibitor, or
  optionally the inhibitor of the RalB protein activity is an allosteric inhibitor of RalB protein activity;
(iii) an inhibitor or depleter of a Src or a Tank Binding Kinase-1 (TBK1) protein or an inhibitor of Src or TBK1 protein activation,
  wherein optionally the inhibitor of the Src or the TBK1 protein activity is:
  an amlexanox (or 2-amino-7-isopropyl-5-oxo-5H-chromeno[2,3-b]pyridine-3-carboxylic acid), or an APH-THASOL™; or
  a γ(1)34.5 protein of herpes simplex viruses (HSV) (see e.g., Ma et al., J Virol. 2012 February; 86(4):2188-96); or
  a BX795 as described in, e.g., Bain et al., Biochem J. (2007) December 15; 408(3):297-315; Clark et al., (2009) J. Biol. Chem. 284:14136-14146; or
  an azabenzimidazole or an analog or derivative thereof; or
  a 6-amino-pyrazolopyrimidine or an analog or derivative thereof; or,
  a compound having one of the following formulas, or an analog or derivative thereof (see Hutti, et al., (2012) Development of a High-Throughput Assay for Identifying Inhibitors of TBK1 and IKKε. PLoS ONE 7(7): e4149doi: 10.1371/journal.pone):

| Molecule | IKKε | TBK1 | IKKβ | IKKα |
|---|---|---|---|---|
| 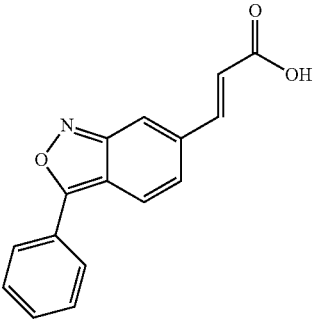 [SMILES: O=C(O)/C=C/c1ccc2c(-c3ccccc3)onc2c1] | 0.77 | 0.44 | >10 | >10 |
| 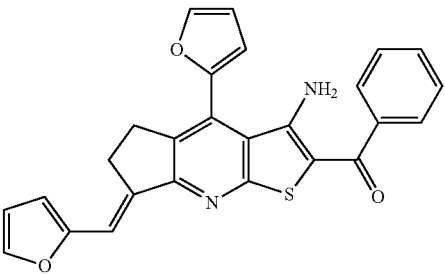 [SMILES: Nc1c(C(=O)c2ccccc2)sc2nc3c(c(-c4ccco4)c12)CC/C3=C\c1ccco1] | >10 | 0.50 | >10 | >10 |
| 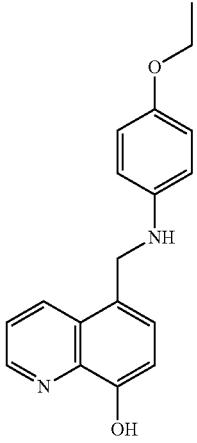 [SMILES: CCOc1ccc(NCc2ccc(O)c3ncccc23)cc1] | >10 | 0.64 | 8.76 | >10 |
| 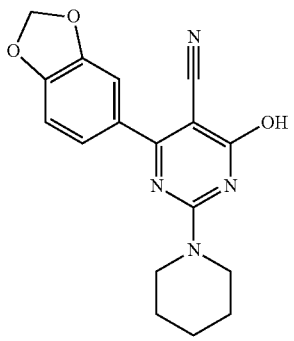 [SMILES: N#Cc1c(O)nc(N2CCCCC2)nc1-c1ccc2c(c1)OCO2] | >10 | 0.67 | >10 | >10 |

-continued

| Molecule | IKKε | TBK1 | IKKβ | IKKα |
| --- | --- | --- | --- | --- |
| [chemical structure] | >10 | 0.87 | >10 | >10 | and optionally the inhibitor of the Src or the TBK1 protein activity is an allosteric inhibitor of Src or TBK1 protein activity;

(iv) an inhibitor or depleter of a NFKB or a Interferon regulatory factor 3 (IRF3) protein or an inhibitor of RalB protein activation, wherein optionally the inhibitor of the NFKB or the IRF3 protein activity is an allosteric inhibitor of an NFKB or an Interferon regulatory factor 3 (IRF3) protein activity;

(v) an inhibitor or depleter of NFKB or IKK, or an inhibitor of NFKB or IKK protein activation, wherein optionally the NFKB inhibitor comprises a lenalidomide or a REVLIMID™ (Celgene Corp., Summit, N.J.) and optionally the IKK inhibitor comprises a PS1145 (Millennium Pharmaceuticals, Cambridge, Mass.);

(vi) a lenalidomide or a REVLIMID™ and PS1145;

(vii) a lenalidomide or a REVLIMID™; a PS1145; and, a Receptor Tyrosine Kinase (RTK) inhibitor, and optionally the RTK inhibitor comprises SU14813 (Pfizer, San Diego, Calif.);

(viii) an inhibitor of Galectin-3; or (ix) any combination of (i) to (viii), or (2) one or any combination of the compound, composition or formulation, or compounds, compositions or formulations, of (1), and at least one growth factor inhibitor, wherein optionally the at least one growth factor inhibitor comprises a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor;

wherein optionally the combination or the therapeutic combination comprises: (i) an inhibitor or depleter of a Src or a Tank Binding Kinase-1 (TBK1) protein or an inhibitor of Src or TBK1 protein activation, wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™, and (ii) an RTK inhibitor, wherein optionally the RTK inhibitor is a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor or a combination thereof;

wherein optionally the combination or the therapeutic combination comprises an erlotinib with either a Lenalidomide or a PS-1145, or both a Lenalidomide and a PS-1145; and (b) administering a sufficient amount of the at least one compound, composition or formulation to the cell, or the combination of compounds, to:

overcome or diminish or prevent a Growth Factor Inhibitor (GFI) resistance in a cell, or increase the growth-inhibiting effectiveness of a Growth Factor inhibitor on a cell, or sensitize, increase sensitivity or re-sensitize a cell to a Growth Factor Inhibitor (GFI), or sensitize, increase sensitivity or re-sensitize a dysfunctional cell, a tumor or cancer to a drug, wherein optionally the drug is a Receptor Tyrosine Kinase (RTK) inhibitor, or an erlotinib, a lapatinib or a lenalidomide, sensitize, increase sensitivity or re-sensitize a tumor that is resistant to a cancer or anti-tumor drug, or reverse a tumor cell, a cancer cell, a cancer stem cell or a dysfunctional cell initiation or self-renewal capacity.

In alternative embodiments of the methods:

(a) the at least one compound, composition or formulation, or combination of compounds, is formulated as a pharmaceutical composition;

(b) the method of (a), wherein the compound, composition or formulation or pharmaceutical composition is administered in vitro, ex vivo or in vivo, or is administered to an individual in need thereof;

(c) the method of (a) or (b), wherein the at least one compound, composition or formulation is a pharmaceutical composition is formulated for administration intravenously (IV), parenterally, nasally, topically, orally, or by liposome or targeted or vessel-targeted nanoparticle delivery;

(d) the method of any of (a) to (c), wherein the compound or composition comprises or is an inhibitor of transcription, translation or protein expression;

(e) the method of any of (a) to (d), wherein the compound or composition is a small molecule, a protein, an antibody, a monoclonal antibody, a nucleic acid, a lipid or a fat, a polysaccharide, an RNA or a DNA;

(f) the method of any of (a) to (e), wherein the compound or composition comprises or is: a VITAXIN™ (Applied Molecular Evolution, San Diego, Calif.) antibody, a humanized version of an LM609 monoclonal antibody, an LM609 monoclonal antibody, or any antibody that functionally blocks an $\alpha_v\beta_3$ integrin or any member of an $\alpha_v\beta_3$ integrin-comprising complex or an integrin $\alpha_v\beta_3$ (anb3)/RalB/NFkB signaling axis;

(g) the method of any of (a) to (e), wherein the compound or composition comprises or is a Src inhibitor, a dasatinib, a saracatinib; a bosutinib; a NVP-BHG712, or any combination thereof;

(h) the method of any of (a) to (g), wherein Growth Factor Inhibitor is or comprises an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof;

(i) the method of any of (a) to (h), wherein the Growth Factor Inhibitor decreases, slows or blocks new blood vessel growth, neovascularization or angiogenesis; or, wherein administering the Growth Factor Inhibitor treats or ameliorates conditions that are responsive to blocking or slowing cell growth, and/or the development of neovascularization or new blood vessels;

(j) the method of any of (a) to (h), wherein the NF-kB inhibitor comprises or consists of one or more of: an antioxidant; an α-lipoic acid; an α-tocopherol; a 2-amino-1-methyl-6-phenylimidazo[4,5-β]pyridine; an allopurinol; an anetholdithiolthione; a cepharanthine; a beta-carotene; a dehydroepiandrosterone (DHEA) or a DHEA-sulfate (DHEAS); a dimethyldithiocarbamates (DMDTC); a dimethylsulfoxide (DMSO); a flavone, a Glutathione; Vitamin C or Vitamin B6, or one or more compositions listed in Table 1 or Table 2, or any combination thereof;

(k) the method of any of (a) to (j), wherein the at least one compound, composition or formulation, or combination of compounds, comprises a protcasome inhibitor or a protease inhibitor that can inhibit an Rei and/or an NFkB, or one or more compositions listed in Table 2, or any combination thereof;

(l) the method of any of (a) to (j), wherein the at least one compound, composition or formulation, or combination of compounds, comprises an IkBα (nuclear factor of kappa light polypeptide gene enhancer in B-cells inhibitor, alpha) phosphorylation and/or degradation inhibitor, or one or more compositions listed in Table 3, or any combination thereof; or (m) the method of any of (a) to (l), wherein the method reduces, treats or ameliorates the level of disease in a retinal age-related macular degeneration, a diabetic retinopathy, a cancer or carcinoma, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, leprosy, multiple sclerosis, inflammatory bowel disease, or ulcerative colitis or Crohn's disease.

In alternative embodiments, the invention provides kits, blister packages, lidded blisters or blister cards or packets, clamshells, trays or shrink wraps, comprising:

(a)(i) at least one compound, composition or formulation used to practice a method of the invention, and (ii): at least one Growth Factor Inhibitor; or (b) the kit of (a), further comprising instructions for practicing a method of the invention.

In alternative embodiments, the kit, blister package, lidded blister, blister card, packet, clamshell, tray or shrink wrap comprises: a combination or a therapeutic combination of drugs comprising: an erlotinib with either a Lenalidomide or a PS-1145, or both a Lenalidomide and a PS-1145.

In alternative embodiments, the invention provides methods for determining:

whether an individual or a patient would benefit from or respond to administration of a Growth Factor Inhibitor, or which individuals or patients would benefit from a combinatorial approach comprising administration of a combination of: at least one growth factor and at least one compound, composition or formulation used to practice a method of the invention, such as an NfKb inhibitor, the method comprising:

detecting the levels or amount of integrin $\alpha_v\beta_3$ (anb3) and/or active RalB complex in or on a cell, a tissue or a tissue sample, wherein optionally the detection is by analysis or visualization of a biopsy or a tissue, urine, fluid, serum or blood sample, or a pathology slide taken from the patient or individual, or by a fluorescence-activated cell sorting (FACS) or flow cytometry analysis or the sample or biopsy, wherein optionally the cell or tissue or tissue sample is or is derived from a tumor or a cancer, wherein optionally the method further comprises taking a biopsy or a tissue, urine, fluid, serum or blood sample from an individual or a patient, wherein a finding of increased levels or amounts of integrin $\alpha_v\beta_3$ (anb3) and/or active RalB complexes in or on the cell, tissue or the tissue sample as compared to normal, normalized or wild type cells or tissues, indicates that:

the individual or patient would benefit from a combinatorial approach comprising administration of a combination of: at least one growth factor and at least one compound, composition or formulation used to practice a method of the invention.

In alternative embodiments of methods of the invention, the detecting of the levels or amount of integrin $\alpha_v\beta_3$ (anb3) and/or active RalB complex in or on the cell, tissue or the tissue sample is done before or during a drug or a pharmaceutical treatment of an individual using at least one compound, composition or formulation used to practice a method of the invention.

In alternative embodiments, the invention provide uses of a combination of compounds in the manufacture of a medicament, wherein the combination of compounds comprises:

(1) at least one compound comprising or consisting of:
(i) an inhibitor or depleter of integrin $\alpha_v\beta_3$ (anb3), or an inhibitor of integrin $\alpha_v\beta_3$ (anb3) protein activity, or an inhibitor of the formation or activity of an integrin anb3/RalB signaling complex, or an inhibitor of the formation or signaling activity of an integrin $\alpha_v\beta_3$ (anb3)/RalB/NFkB signaling axis, wherein optionally the inhibitor of integrin $\alpha_v\beta_3$ protein activity is an allosteric inhibitor of integrin $\alpha_v\beta_3$ protein activity;

(ii) an inhibitor or depleter of a RalB protein or an inhibitor of a RalB protein activation, or an inhibitor or depleter of the recruitment of KRAS/RalB to the plasma membrane or the association of KRAS to RalB, wherein optionally the inhibitor is an allosteric inhibitor, or the inhibitor of the RalB protein activity is an allosteric inhibitor of RalB protein activity;

(iii) an inhibitor or depleter of a Src or a Tank Binding Kinase (TBK1) protein or an inhibitor of Src or TBK1 protein activation, wherein optionally the inhibitor of the Src or the TBK1 protein activity is: an amlexanox (or 2-amino-7-isopropyl-5-oxo-5H-chromeno[2,3-b]pyridine-3-carboxylic acid), or an APHTHASOL™; or a γ(1)34.5 protein of herpes simplex viruses (HSV) (see e.g., Ma et al., J Virol. 2012 February; 86(4):2188-96); or, BX795 (as described in, e.g., Bain et al., Biochem J. (2007) December 15; 408(3):297-315; Clark et al., (2009) J. Biol. Chem. 284:14136-14146); or an azabenzimidazole or an analog or derivative thereof; or a 6-amino-pyrazolopyrimidine or an analog or derivative thereof; or, a compound having one of the following formulas, or an analog or derivative thereof (see Hutti, et al., (2012) Development of a High-Throughput Assay for Identifying inhibitors of TBK1 and IKKε. PLoS ONE 7(7): e411494.doi: 10.1371/joural.pone):

| Molecule | IKKε | TBK1 | IKKβ | IKKα |
|---|---|---|---|---|
| (structure: 3-phenyl-2,1-benzisoxazole-6-acrylic acid) | 0.77 | 0.44 | >10 | >10 |
| (structure: amino-furyl-furfurylidene cyclopenta-thienopyridine benzoyl) | >10 | 0.50 | >10 | >10 |
| (structure: 5-[(4-ethoxyphenylamino)methyl]-8-hydroxyquinoline) | >10 | 0.64 | 8.76 | >10 |
| (structure: 4-(benzo[d][1,3]dioxol-5-yl)-6-hydroxy-2-(piperidin-1-yl)pyrimidine-5-carbonitrile) | >10 | 0.67 | >10 | >10 |

| Molecule | IKKε | TBK1 | IKKβ | IKKα |
|---|---|---|---|---|
| (structure shown) | >10 | 0.87 | >10 | >10 | and optionally the inhibitor of the Src or the TBK1 protein activity is an allosteric inhibitor of Src or TBK1 protein activity;
(iv) an inhibitor or depleter of a NFKB or a Interferon regulatory factor 3 (IRF3) protein or an inhibitor of RalB protein activation,
wherein optionally the inhibitor of the NFKB or the IRF3 protein activity is an allosteric inhibitor of an NFKB or an Interferon regulatory factor 3 (IRF3) protein activity;
(v) an inhibitor or depleter of NFKB or IKK, or an inhibitor of NFKB or IKK protein activation,
wherein optionally the NFKB inhibitor comprises a lenalidomide or a REVLIMID™ (Celgene Corp., Summit, N.J.) and optionally the IKK inhibitor comprises a PS1145 (Millennium Pharmaceuticals, Cambridge, Mass.);
(vi) a lenalidomide or a REVLIMID™ and PS1145;
(vii) a lenalidomide or a REVLIMID™; a PS1145; and, a Receptor Tyrosine Kinase (RTK) inhibitor, and optionally the RTK inhibitor comprises SU14813 (Pfizer, San Diego, Calif.);
(viii) an inhibitor of Galectin-3; or
(ix) any combination of (i) to (viii), or
(2) one or any combination of the compound, composition or formulation, or compounds, compositions or formulations, of (1), and at least one growth factor inhibitor,
wherein optionally the at least one growth factor inhibitor comprises a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor;
wherein optionally the combination or the therapeutic combination comprises: (i) an inhibitor or depleter of a Src or a Tank Binding Kinase-1 (TBK1) protein or an inhibitor of Src or TBK1 protein activation, wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™, and (ii) an RTK inhibitor, wherein optionally the RTK inhibitor is a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor or a combination thereof;
wherein optionally the combination or the therapeutic combination comprises an erlotinib with either a Lenalidomide or a PS-1145, or both a Lenalidomide and a PS-1145;
(vii) a lenalidomide or a REVLIMID™; a PS1145; and, a Receptor Tyrosine Kinase (RTK) inhibitor, and optionally the RTK inhibitor comprises SU14813 (Pfizer, San Diego, Calif.);
(viii) an inhibitor of Galectin-3; or
(ix) any combination of (i) to (viii); and
(2) at least one Growth Factor Inhibitor,
wherein optionally the Growth Factor Inhibitor is or comprises an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof; or, the Growth Factor Inhibitor decreases, slows or blocks new blood vessel growth, neovascularization or angiogenesis; or, wherein administering the Growth Factor Inhibitor treats or ameliorates conditions that are responsive to blocking or slowing cell growth, and/or the development of neovascularization or new blood vessels,
wherein optionally the combination or the therapeutic combination comprises an erlotinib with either a Lenalidomide or a PS-1145, or both a Lenalidomide and a PS-1145.
In alternative embodiments, the invention provides therapeutic combinations of drugs comprising or consisting of a combination of at least two compounds: wherein the at least two compounds comprise or consist of:
(1) at least one compound comprising or consisting of:
(i) an inhibitor or depleter of integrin $\alpha_v\beta_3$ (anb3), or an inhibitor of integrin $\alpha_v\beta_3$ (anb3) protein activity, or an inhibitor of the formation or activity of an integrin anb3/RalB signaling complex, or an inhibitor of the formation or signaling activity of an integrin $\alpha_v\beta_3$ (anb3)/RalB/NFkB signaling axis,
wherein optionally the inhibitor of integrin $\alpha_v\beta_3$ protein activity is an allosteric inhibitor of integrin $\alpha_v\beta_3$ protein activity;
(ii) an inhibitor or depleter of a RalB protein or an inhibitor of a RalB protein activation, or an inhibitor or depleter of the recruitment of KRAS/RalB to the plasma membrane or the association of KRAS to RalB,
wherein optionally the inhibitor is an allosteric inhibitor, or the inhibitor of the RalB protein activity is an allosteric inhibitor of RalB protein activity;
(iii) an inhibitor or depleter of a Src or a Tank Binding Kinase (TBK1) protein or an inhibitor of Src or TBK1 protein activation,
wherein optionally the inhibitor of the Src or the TBK1 protein activity is: an amlexanox (or 2-amino-7-isopropyl-5-oxo-5H-chromeno[2,3-b]pyridine-3-carboxylic acid), or an APHTHASOL™; or a γ(1)34.5 protein of herpes simplex viruses (HSV) (see e.g., Ma et al., J Virol. 2012 February; 86(4):2188-96); or, BX795 (as described in, e.g., Bain et al., Biochem J. (2007) December 15; 408(3):297-315; Clark et al., (2009) J. Biol. Chem. 284:14136-14146); or an azabenzimidazole or an analog or derivative thereof; or a 6-aminopyrazolopyrimidine or an analog or derivative thereof;

or, a compound having one of the following formulas, or an analog or derivative thereof (see Hatti, et al., (2012) Development of a High-Throughput Assay for identifying Inhibitors of TBK1 and IKKε. PLoS ONE 7(7):e41494.doi: 10.1371/journal.pone):

| Molecule | IKKε | TBK1 | IKKβ | IKKα |
|---|---|---|---|---|
| | 0.77 | 0.44 | >10 | >10 |
| | >10 | 0.50 | >10 | >10 |
| | >10 | 0.64 | 8.76 | >10 |
| | >10 | 0.67 | >10 | >10 |

| Molecule | IKKε | TBK1 | IKKβ | IKKα |
|---|---|---|---|---|
| 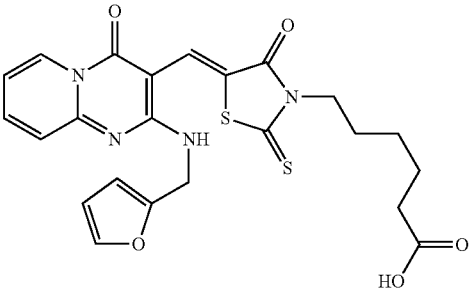 [SMILES: O=C(O)CCCCCN1C(=O)/C(=C/c2c(NCc3ccco3)nc3ccccn3c2=O)SC1=S] | >10 | 0.87 | >10 | >10 | and optionally the inhibitor of the Src or the TBK1 protein activity is an allosteric inhibitor of Src or TBK1 protein activity;

(iv) an inhibitor or depleter of a NFKB or a Interferon regulatory factor 3 (IRF3) protein or an inhibitor of RalB protein activation, wherein optionally the inhibitor of the NFKB or the IRF3 protein activity is an allosteric inhibitor of an NFKB or an Interferon regulatory factor 3 (IRF3) protein activity;

(v) an inhibitor or depleter of NFKB or IKK, or an inhibitor of NFKB or IKK protein activation, wherein optionally the NFKB inhibitor comprises a lenalidomide or a REVLIMID™ (Celgene Corp., Summit, N.J.) and optionally the IKK inhibitor comprises a PS1145 (Millennium Pharmaceuticals, Cambridge, Mass.);

(vi) a lenalidomide or a REVLIMID™ and PS1145;

(vii) a lenalidomide or a REVLIMID™; a PS1145; and, a Receptor Tyrosine Kinase (RTK) inhibitor, and optionally the RTK inhibitor comprises SU14813 (Pfizer, San Diego, Calif.);

(viii) an inhibitor of Galectin-3; or (ix) any combination of (i) to (viii), or (2) one or any combination of the compound, composition or formulation, or compounds, compositions or formulations, of (1), and at least one growth factor inhibitor, wherein optionally the at least one growth factor inhibitor comprises a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor;

wherein optionally the combination or the therapeutic combination comprises: (i) an inhibitor or depleter of a Src or a Tank Binding Kinase-1 (TBK1) protein or an inhibitor of Src or TBK1 protein activation, wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™, and (ii) an RTK inhibitor, wherein optionally the RTK inhibitor is a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor or a combination thereof;

wherein optionally the combination or the therapeutic combination comprises an erlotinib with either a Lenalidomide or a PS-1145, or both a Lenalidomide and a PS-1145;

(vii) a lenalidomide or a REVLIMID™; a PS1145; and, a Receptor Tyrosine Kinase (RTK) inhibitor, and optionally the RTK inhibitor comprises SU14813 (Pfizer, San Diego, Calif.);

(viii) an inhibitor of Galectin-3; or (ix) any combination of (i) to (viii); and (2) at least one Growth Factor Inhibitor, wherein optionally the Growth Factor Inhibitor is or comprises an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof; or, the Growth Factor Inhibitor decreases, slows or blocks new blood vessel growth, neovascularization or angiogenesis; or, wherein administering the Growth Factor Inhibitor treats or ameliorates conditions that are responsive to blocking or slowing cell growth, and/or the development of neovascularization or new blood vessels, wherein optionally the combination or the therapeutic combination comprises an erlotinib with either a Lenalidomide or a PS-1145, or both a Lenalidomide and a PS-1145.

In alternative embodiments, the invention provides combinations, or therapeutic combinations, for overcoming or diminishing or preventing Growth Factor Inhibitor (GFI) resistance in a cell, or, a method for increasing the growth-inhibiting effectiveness of a Growth Factor inhibitor on a cell, or, a method for re-sensitizing a cell to a Growth Factor Inhibitor (GFI), wherein the combination comprises or consists of:

(1) at least one compound comprising or consisting of:

(i) an inhibitor or depleter of integrin $\alpha_v\beta_3$ (anb3), or an inhibitor of integrin $\alpha_v\beta_3$ (anb3) protein activity, or an inhibitor of the formation or activity of an integrin anb3/RalB signaling complex, or an inhibitor of the formation or signaling activity of an integrin $\alpha_v\beta_3$ (anb3)/RalB/NFkB signaling axis, wherein optionally the inhibitor of integrin $\alpha_v\beta_3$ protein activity is an allosteric inhibitor of integrin $\alpha_v\beta_3$ protein activity;

(ii) an inhibitor or depleter of a RalB protein or an inhibitor of a RalB protein activation, or an inhibitor or depleter of the recruitment of KRAS/RalB to the plasma membrane or the association of KRAS to RalB, wherein optionally the inhibitor is an allosteric inhibitor, or the inhibitor of the RalB protein activity is an allosteric inhibitor of RalB protein activity;

(iii) an inhibitor or depleter of a Src or a Tank Binding Kinase (TBK1) protein or an inhibitor of Src or TBK1 protein activation, wherein optionally the inhibitor of the Src or the TBK1 protein activity is: an amlexanox (or 2-amino-7-isopropyl-5-oxo-5H-chromeno[2,3-b]pyridine-3-carboxylic acid), or an APHTHASOL™; or a γ(1)34.5 protein of herpes simplex viruses (HSV) (see e.g., Ma et al., J Virol. 2012 February; 86(4):2188-96); or, a BX795 (as described in, e.g., Bain et al., Biochem J. (2007) December 15; 408(3):297-315; Clark et al., (2009) J. Biol. Chem. 284:14136-14146); or an azabenzimidazole or an analog or derivative thereof; or a 6-amino-pyrazolopyrimidine or an analog or derivative thereof; or, a compound having one of the following formulas, or an analog or derivative thereof (see Hutti, et al., (2012) Development of a High-Throughput Assay for Identifying Inhibitors of TBK1 and IKKε PLoS ONE 7(7): e41494.doi: 10.1371/journal.pone):

| Molecule | IKKε | TBK1 | IKKβ | IKKα |
|----------|------|------|------|------|
|          | 0.77 | 0.44 | >10  | >10  |
|          | >10  | 0.50 | >10  | >10  |
|          | >10  | 0.64 | 8.76 | >10  |

| Molecule | IKKε | TBK1 | IKKβ | IKKα |
|---|---|---|---|---|
| 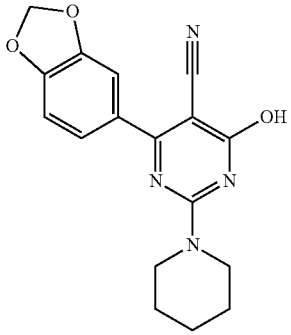 [SMILES: N#Cc1c(O)nc(N2CCCCC2)nc1-c1ccc2c(c1)OCO2] | >10 | 0.67 | >10 | >10 |
| 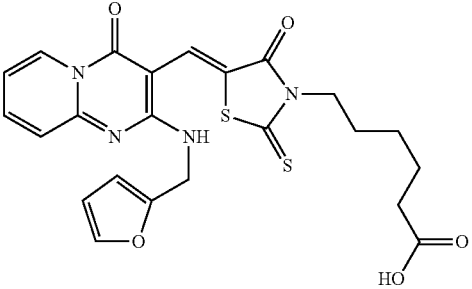 [SMILES: O=C(O)CCCCCN1C(=O)/C(=C/c2c(NCc3ccco3)nc3ccccn3c2=O)SC1=S] | >10 | 0.87 | >10 | >10 | and optionally the inhibitor of the Src or the TBK1 protein activity is an allosteric inhibitor of Src or TBK1 protein activity;
(iv) an inhibitor or depleter of a NFKB or a Interferon regulatory factor 3 (IRF3) protein or an inhibitor of RalB protein activation,
wherein optionally the inhibitor of the NFKB or the IRF3 protein activity is an allosteric inhibitor of an NFKB or an Interferon regulatory factor 3 (IRF3) protein activity;
(v) an inhibitor or depleter of NFKB or IKK, or an inhibitor of NFKB or IKK protein activation,
wherein optionally the NFKB inhibitor comprises a lenalidomide or a REVLIMID™ (Celgene Corp., Summit, N.J.) and optionally the IKK inhibitor comprises a PS1145 (Millennium Pharmaceuticals, Cambridge, Mass.);
(vi) a lenalidomide or a REVLIMID™ and PS1145;
(vii) a lenalidomide or a REVLIMID™; a PS1145; and, a Receptor Tyrosine Kinase (RTK) inhibitor, and optionally the RTK inhibitor comprises SU14813 (Pfizer, San Diego, Calif.);
(viii) an inhibitor of Galectin-3; or
(ix) any combination of (i) to (viii), or
(2) one or any combination of the compound, composition or formulation, or compounds, compositions or formulations, of (1), and at least one growth factor inhibitor,
wherein optionally the at least one growth factor inhibitor comprises a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor;
wherein optionally the combination or the therapeutic combination comprises: (i) an inhibitor or depleter of a Src or a Tank Binding Kinase-1 (TBK1) protein or an inhibitor of Src or TBK1 protein activation, wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™, and (ii) an RTK inhibitor, wherein optionally the RTK inhibitor is a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor or a combination thereof;
wherein optionally the combination or the therapeutic combination comprises an erlotinib with either a Lenalidomide or a PS-1145, or both a Lenalidomide and a PS-1145.

The details of one or more embodiments of the invention are set forth in the accompanying drawings and the description below. Other features, objects, and advantages of the invention will be apparent from the description and drawings, and from the claims. All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 1 (c) illustrates: Top, immunofluorescence staining of integrin αvβ3 in tissue specimens obtained from orthotopic pancreatic tumors treated with vehicle or erlotinib; Bottom, Integrin αvβ3 expression was quantified as ratio of integrin αvβ3 pixel area over nuclei pixel area using METAMORPH™.

FIG. 2 illustrates that integrin αvβ3 cooperates with K-RAS to promote resistance to EGFR blockade: FIG. 2(a-b) illustrates tumor sphere formation assay of FG tumor cells expressing (a) or lacking (b) integrin β3 depleted of KRAS (shKRAS) or not (shCTRL) and treated with a dose response of erlotinib; FIG. 2(c) illustrates confocal microscopy images of PANC-1 and FG-β3 cells grown in suspension; FIG. 2(d) illustrates an immunoblot analysis of RAS activity assay performed in PANC-1 cells using GST-Rafl-RBD immunoprecipitation as described below; FIG. 2(e) illustrates an immunoblot analysis of Integrin αvβ3 immunoprecipitates from BxPC-3 β3-positive cells grown in suspension and untreated or treated with EGF, and RAS activity was determined using a GST-Rafl-RBD immunoprecipitation assay; as discussed in detail in Example 1, below.

FIG. 3 illustrates that RalB is a key modulator of integrin αvβ3-mediated EGFR TKI resistance: FIG. 3(a) illustrates tumor spheres formation assay of FG-β3 treated with non-silencing (shCTRL) or RalB-specific shRNA and exposed to a dose response of erlotinib; FIG. 3(b) illustrates effects of depletion of RalB on erlotinib sensitivity in β3-positive tumor in a pancreatic orthotopic tumor model; FIG. 3(c) illustrates tumor spheres formation assay of FG cells ectopically expressing vector control, WT RalB FLAG tagged constructs or a constitutively active RalB G23V FLAG tagged treated with erlotinib (0.5 μM); FIG. 3(d) illustrates RalB activity was determined in FG, FG-β3 expressing non-silencing or KRAS-specific shRNA, by using a GST-RalBP1-RBD immunoprecipitation assay; FIG. 3(e) illustrates: Right, overall active Ral immunohistochemical staining intensity between β3 negative and β3 positive human tumors; as discussed in detail in Example 1, below.

FIG. 4 illustrates that integrin αvβ3/RalB complex leads to NF-μB activation and resistance to EGFR TKI.

FIG. 6 (or Supplementary FIG. 2, Example 1) illustrates integrin αvβ3, even in its unligated state, promotes resistance to Growth Factor inhibitors but not to chemotherapies.

FIG. 7 (or Supplementary FIG. 3, Example 1) illustrates that integrin αvβ3 does not colocalize with active HRAS, NRAS and RRAS.

FIG. 8 (or Supplementary FIG. 4, Example 1) illustrates that Galectin-3 is required to promote integrin αvβ3/KRAS complex formation: FIG. 8(a-b) illustrates confocal microscopy images of Panc-1 cells lacking or expressing integrin αvβ3 grown in suspension; FIG. 8(a) illustrates cells stained for KRAS (green), Galectin-3 (red), and DNA (TOPRO-3, blue); FIG. 8(b) illustrates cells stained for integrin αvβ3 (green), Galectin-3 (red) and DNA (TOPRO-3, blue), Scale bar, 10 μm, data are representative of three independent experiments; FIG. 8(c) illustrates an immunoblot analysis of Galectin-3 immuno-precipitates from PANC-1 cells expressing non-silencing (sh CTRL) or integrin β3-specific shRNA (sh β3), data are representative of three independent experiments; FIG. 8(d) illustrates an immunoblot analysis of integrin β3 immunoprecipitates from PANC-1 cells expressing non-silencing (sh CTRL) or Galectin-3-specific shRNA (sh Ga13), data are representative of three independent experiments; as discussed in detail in Example 1, below.

FIG. 10 (or Supplementary FIG. 6, Example 1) illustrates that RalB is sufficient to promote resistance to EGFR TKI.

FIG. 11 (or Supplementary FIG. 8, Example 1) illustrates that integrin αvβ3 colocalizes with RalB in human breast and pancreatic tumor biopsies and interacts with RalB in cancer cells.

FIG. 12 (or FIG. 1 in Example 2) illustrates data showing that integrin β3 is expressed in EGFR inhibitor resistant tumors and is necessary and sufficient to drive EGFR inhibitor resistance: FIG. 12(A) schematically illustrates that the identification of the most upregulated tumor progression genes common to erlotinib resistant carcinomas; FIG. 12(B) in table form shows Erlotinib $IC_{50}$ in a panel of human carcinoma cell lines treated with erlotinib in 3D culture; FIG. 12(C) graphically illustrates percentage of integrin β3 positive cells in parental lines vs. after 3 or 8 weeks treatment with erlotinib; FIG. 12(D) graphically illustrates quantification of integrin β3 (ITGβ3) gene expression in human lung cancer biopsies from patients from the BATTLE Study (18) who were previously treated with an EGFR inhibitor and progressed (n=27), versus patients who were EGFR inhibitor naïve (n=39); FIG. 12(E) illustrates images of paired human lung cancer biopsies obtained before and after erlotinib resistance were immunohistochemically stained for integrin β, scale bar, 50 μm; FIG. 12(F) graphically illustrates: Right graph shows effect of integrin β3 knockdown on erlotinib resistance of β-positive cells, and Left graph shows effect of integrin β3 ectopic expression on erlotinib resistance in FG and H441 cells; FIG. 12(G) graphically illustrates: Right graph shows the effect of integrin β3 knockdown on erlotinib resistance in vivo, A549 shCTRL and A549 sh integrin β3 (n=8 per treatment group) were treated with erlotinib (25 mg/kg/day) or vehicle during 16 days, results are expressed as average of tumor volume at day 16. *P<0.05; and Left graph shows orthotopic FG and FG-β3 tumors treated for 30 days with vehicle or erlotinib, results are expressed as % tumor weight compared to vehicle control; as further described in Example 2, below.

FIG. 13(B-C) illustrates confocal microscopy images showing immunostaining for integrin β3 (green), KRAs (red) and DNA (Topro-3, blue) for PANC-1 (KRAS mutant) and HCC827 (KRAS wild-type) after acquired resistance to erlotinib (HCC827R) grown in suspension in absence (Vehicle) or in presence of erlotinib (0.5 μM and 0.1 μM respectively), arrows indicate clusters where integrin β3 and KRAS colocalize (yellow)

FIG. 14 (or FIG. 3 in Example 2) illustrates data showing that RalB is a central player of integrin β3-mediated EGFR inhibitor resistance: FIG. 14(A) graphically illustrates the effect of RalB knockdown on erlotinib resistance of β3-positive epithelial cancer cell lines, cells were treated with 0.5 μM of erlotinib: FIG. 14(B) graphically illustrates the effect of RalB knockdown on erlotinib resistance of β3-positive human pancreatic (FG-β3) orthotopic tumor xenografts, established tumors expressing non-target shRNA, (shCTRL) or a shRNA targeting RalB (sh RalB) were randomized and treated for 10 days with vehicle or erlotinib, results are expressed as % of tumor weight changes after erlotinib treatment compared to vehicle; FIG. 14(C) graphically illustrates the effect of expression of a constitutively active Ral G23V mutant on erlotinib response of β3 negative cells, cells were treated with 0.5 μM of erlotinib; FIG. 14(D) illustrates the effect of expression of integrin β3 on KRAS and RalB membrane localization; FIG. 14(E) illustrates Ral activity that was determined in PANC-1 cells grown in suspension by using a GST-RalBP1-RBD immunoprecipitation assay, immunoblots indicate RalB activity and association of active RalB with integrin β3; FIG. 14(F) illustrates confocal microscopy images of integrin αvβ3 (green), RalB (red) and DNA (TOPRO-3, blue) in tumor biopsies from pancreatic cancer patients; FIG. 14(G) illustrates the effect of β3 expression and KRAS expression on RalB activity, measured using a GST-RalBP1-RBD immunoprecipitation assay; FIG. 14(H) illustrates immunoblot analysis of FG and FG-β3 stably expressing non-target shRNA control or RalB-specific shRNA, grown in suspension and treated with erlotinib (0.5 μM); FIG. 14(I) graphically illustrates the effect of a Tank Binding Kinase (TBK1) and p65 NFκB on erlotinib resistance of FG-β3 cells, cells were treated with 0.5 μM of erlotinib; as further described in Example 2, below.

FIG. 15 (or FIG. 4 in Example 2) illustrates data showing that reversal of β3-mediated EGFR inhibitor resistance in oncogenic KRAS model by pharmacological inhibition.

FIG. 16 (or supplementary FIG. S1, in Example 2) illustrates data showing that illustrates resistance to EGFR inhibitor is associated with integrin β3 expression in pancreatic and lung human carcinoma cell lines: FIG. 16(A) illustrates immunoblots showing integrin β3 expression in human cell lines used in FIG. 12; FIG. 16(B) graphically illustrates data showing the effect of erlotinib on HCC827 xenograft tumors in immuno—compromised mice relative to vehicle-treated control tumors; FIG. 16(C) left, graphically illustrates data of Integrin αvβ3 quantification in orthotopic lung (upper panel) and pancreas (lower panel) tumors treated with vehicle or erlotinib until resistance, FIG. 16(C) right, illustrates a representative immunofluorescent staining of integrin αvβ3 in lung (upper panel) and pancreatic (lower panel) human xenografts treated 4 weeks with vehicle or erlotinib; as further described in Example 2, below.

FIG. 18 (or supplementary FIG. S3, in Example 2) illustrates Integrin β3 confers Receptor Tyrosine Kinase inhibitor resistance.

FIG. 19 (or supplementary FIG. S4, in Example 2) illustrates integrin β3-mediated EGFR inhibitor resistance is independent of its ligand binding.

FIG. 20 (or supplementary FIG. S5, in Example 2) illustrates integrin β3 colocalizes and interacts with oncogenic and active wild-type KRAS.

FIG. 21 (or supplementary FIG. S6, in Example 2) illustrates integrin β3 expression promotes KRAS dependency: FIG. 21(A) illustrates Immunoblots showing KRAS knockdown efficiency in cells used in FIG. 13; FIG. 21(B) illustrates Representative photographs of crystal violet-stained tumorspheres of FG and A549 cells expressing non-target shRNA control or specific-KRAS shRNA; FIG. 21(C) illustrates the effect of an additional KRAS knockdown on tumorspheres formation in PANC-1 stably expressing non-target shRNA control (β3-positive) or specific-integrin β3 shRNA (β3 negative); FIG. 21(D) illustrates immunoblots showing KRAS knockdown efficiency; as further described in Example 2, below.

FIG. 23 (or supplementary FIG. S8, in Example 2) illustrates Integrin β3-mediated KRAS dependency and erlotinib resistance is independent of ERK, AKT and RalA.

FIG. 24 (or supplementary FIG. S9, in Example 2) illustrates constitutive active NFkB is sufficient to promote erlotinib resistance.

FIG. 25 (or supplementary FIG. S10, in Example 2) illustrates NFkB inhibitors in combination with erlotinib increase cell death in vivo: FIG. 25(A) and FIG. 25 (B) illustrate Immunoblots showing expression of indicated proteins of representative tumors from shown in FIG. 15B.

FIGS. 26, 27, and 28, illustrate supplementary Table 1 from Example 2, showing that differentially expressed genes in cells resistant to erlotinib (PANC-1, H1650, A459) compared with the average of two sensitive cells (FG, H441) and in HCC827 after acquired resistance in vivo (HCC827R) vs. the HCC827 vehicle-treated control; as further described in Example 2, below.

FIG. 29 illustrates supplementary Table 2, from Example 2, showing KRAS mutational status in pancreatic and lung cell lines used in the study of Example 2, below.

FIG. 31 illustrates data showing how targeting the NF-κB pathway using compositions and methods of this invention can sensitize resistant tumors to growth factor inhibitors by showing the effect of NFkB inhibitors on erlotinib response of β3-negative (b3-negative) cells (FG) and β3-positive cells (FG-β3, MDA-MB231 (intrinsic resistance, FIG. 31A) and FG-R (acquired resistance, FIG. 31B), and EGFR TKI (Tyrosine Kinase Inhibitor) sensitive cells, FIG. 31C. Cells embedded in agar (anchorage independent growth) were treated with vehicle, erlotinib (0.5 µM), Lenalidomide (2 µM), PS-1145 (1 µM) alone or in combination for 10 to 15 days. Then, the soft agar were stained with crystal violet and the colonies were counted manually. The results show that while β3-positive cells (intrinsic FIG. 31A or acquired resistant FIG. 31B cells) were resistant to erlotinib and each NFkB inhibitor alone, the combination of erlotinib with either Lenalidomide or PS-1145 decreased tumorsphere formation.

FIG. 32 (or FIG. 1 of Example 3) illustrates: Integrin β3 expression increase tumor-initiating and self-renewal capacities: FIG. 32(a) Limiting dilution in vivo determining the frequency of tumor-initiating cells for A549 cells expressing non-target shRNA control or integrin β3-specific shRNA and for FG cells expressing control vector or integrin β3 (FG-β3); FIG. 32(b-c-d) Self-renewal capacity of A549 (FIG. 32b) and PANC-1 (FIG. 32c) cells expressing non-target shRNA control (CTRL) or integrin specific shRNA and of FG expressing control vector or integrin β3 (FG-β3) (FIG. 32d); as described in detail in Example 3, below.

FIG. 33 (or FIG. 2, of Example 3) illustrates: Integrin β3 drives resistance to EGFR inhibitors: FIG. 33(f) graphically illustrates Relative mRNA expression of integrin β3 (ITGB3) in HCC827 vehicle-treated tumors (n=5) or erlotinib-treated tumors (n=7) from (e) after acquired resistance; FIG. 33(h) illustrates images of Limiting dilution in vivo determining the frequency of tumor-initiating cells for HCC827 vehicle-treated (vehicle) and erlotinib-treated tumors from (erlotinib resistant non-sorted) (e)

FIG. 34 (or FIG. 3, of Example 3) illustrates: Integrin β3/KRAS complex is critical for integrin β3-mediated stemness: FIG. 34(a) Confocal microscopy images show immunostaining for Integrin β3 (green), KRAS (red) and DNA (TOPRO-3, blue) for FG-β3, A549 and HCC827 after acquired resistance to erlotinib (HCC827 ER) grown in suspension, Arrows indicate clusters where integrin β3 and KRAS colocalize (yellow); FIG. 34(b) Ras activity was determined in PANC-1 cells grown in suspension by using a GST-Rafl-RBD immunoprecipitation assay, Immunoblots indicate KRAS activity and association of active KRAS with integrin β3; FIG. 34(c) Effect of KRAS knockdown on tumorspheres formation in lung (A549 and H441) and pancreatic (FG and PANC-1) cancer cells expressing or lacking integrin β3; FIG. 34(d) Effect of KRAS knockdown on erlotinib resistance of β3-negative and β3-positive epithelial cancer cell lines, Cells were treated with a dose response of erlotinib; FIG. 34(e) Self-renewal capacity of FG-β3 cells expressing non-target shRNA control (shCTRL) or KRAS-specific shRNA measured by quantifying the number of primary and secondary tumorspheres; FIG. 34(f) Confocal microscopy images show immunostaining for integrin β3 (green), KRAS (red) and DNA (TOPRO-3, blue) for PANC-1 cells expressing non-target shRNA control or Galectin 3-specific shRNA grown in suspension; FIG. 34(g) immunoblot analysis of integrin β3 immunoprecipitates from PANC-1 cells expressing non-target shRNA control (CTRL) or Galectin-3-specific shRNA (Gal-3); FIG. 34(h) Effect of Galectin-3 knockdown on integrin β3-mediated anchorage independent growth and erlotinib resistance; FIG. 34(i) Self-renewal capacity of PANC-1 cells expressing non-target shRNA control (shCTRL) or Galectin-3-specific shRNA (sh Gal-3) measured by quantifying the number of primary and secondary tumorspheres; as described in detail in Example 3, below.

FIG. 35 (or FIG. 4, of Example 3) illustrates: RalB/TBK1 signaling is a key modulator of integrin ⊖3-mediated stemness: FIG. 35(a) Effect of RalB knockdown on anchorage independence; FIG. 35(b) Self-renewal capacity of FG-β3 cells expressing non-target shRNA control (sh CTRL) or RalB-specific shRNA (sh RalB) measured by quantifying the number of primary and secondary tumorspheres; FIG. 35(c) Limiting dilution in vivo determining the frequency of tumor-initiating cells for FG-β3 cells expressing non-target shRNA control or integrin RalB-specific shRNA; FIG. 35(d) Effect of RalB knockdown on erlotinib resistance of β3-positive epithelial cancer cell lines; FIG. 35(e) Effect of RalB knockdown on erlotinib resistance of β3-positive human pancreatic (FG-β3) orthotopic tumor xenografts. Established tumors expressing non-target shRNA, (sh CTRL) or a shRNA targeting RalB (sh RalB); FIG. 35(f) Immunoblot analysis of FG and FG-β3 stably expressing non-target shRNA control or RalB-specific shRNA, grown in 3D and treated with erlotinib (0.5 µM); FIG. 35(g) Effect of TBK1 knockdown on PANC-1 self-renewal capacity; FIG. 35(h) Effect of TBK1 knockdown on erlotinib resistance of PANC-1 cells. Cells were treated with 0.5 µM of erlotinib; FIG. 35(i) Mice bearing subcutaneous β3-positive tumors (PANC-1) were treated with vehicle, erlotinib (25 mg/kg/day), amlexanox (25 mg/kg/day) or the combination of erlotinib and amlexanox; as described in detail in Example 3, below.

FIG. 36 (or FIG. S1, of Example 3) illustrates: FIG. 36(a-b) Limiting dilution tables; FIG. 36(c) Immunoblots showing integrin β3 knockdown or ectopic expression efficiency in cells used in FIG. 1 (of Example 3); FIG. 36(d) Viability assay (CellTiter-Glo assay) of FG and FG-β3 cells grown in 3D in media with or without serum; FIG. 36(e) Immunohistochemical analysis of integrin β3 expression in paired human lung cancer biopsies obtained before (upper panel) and after (lower panel) erlotinib resistance; FIG. 36(f) Limiting dilution table; FIG. 36(g) image of Immunohistochemistry staining of CD166 (upper panel) and integrin β3 (lower panel) in human lung tumor biopsies after EGFR™ acquired resistance; as described in detail in Example 3, below.

FIG. 37 (or FIG. S2, of Example 3) illustrates.

FIG. 38 (or FIG. S3, of Example 3) illustrates: FIG. 38(a) graphically illustrates the Effect of ERK, AKT and RalA knockdown on erlotinib response of β3-negative FG and 3-positive FG-3 cells; FIG. 38(b) Immunoblots showing ERK, AKT and RalA knockdown efficiency in cells used in (a); FIG. 38(c) Immunoblots showing RalB knockdown efficiency in cells used in FIG. 3 (of Example 3); FIG. 38(d) graphically illustrates the effect of a second RalB knockdown (shRalB 2) on tumorspheres formation in PANC-1 stably expressing non-target shRNA control (β3-positive) or specific-integrin β3 shRNA (3 negative); FIG. 38(e) Limiting dilution table; FIG. 38(f) Confocal microscopy images of integrin αvβ3 (green), RalB (red) and DNA (TOPRO-3, blue) in tumor biopsies from pancreatic cancer patients; FIG. 38(g) Ral activity was determined in PANC-1 cells grown in suspension by using a GST-RalBP1-RBD immunoprecipitation assay. Immunoblots indicate RalA and RalB activities; FIG. 38(h) Effect of β3 expression and KRAS expression on RalB activity, measured using a GST-RalBP1-RBD immunoprecipitation assay; FIG. 38(i) illustrates the effect of expression of a constitutively active Ral G23V mutant on erlotinib resistance of β3 positive and negative cells, left panel graphically presenting data and right panel illustrating an immunoblot showing FLAG, RalB and Hsp90 expression; as described in detail in Example 3, below.

FIG. 39 (or FIG. S4, of Example 3) illustrates.

FIG. 40 graphically illustrates data demonstrating that depletion of RalB overcomes erlotinib resistance in KRAS mutant cells.

FIG. 41 graphically illustrates data demonstrating that depletion of TBK1 overcomes erlotinib resistance in KRAS mutant cells: FIG. 41A shows the number of tumorspheres as a percent of non-treated cells with and without siRNA depletion of TBK1, and FIG. 41C shows tumor size as a percent of control with erlotinib, amlexanox and erlotinib+amlexanox; as discussed in detail in Example 2, below.

Like reference symbols in the various drawings indicate like elements.

Figure 1A:
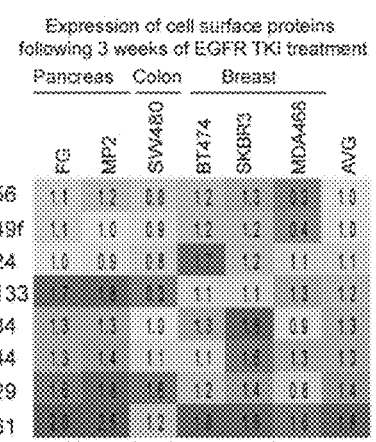
FIG. 1(a) illustrates flow cytometric quantification of cell surface markers after 3 weeks treatment with erlotinib (pancreatic and colon cancer cells) or lapatinib (breast cancer cells)

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides compositions and methods for overcoming or diminishing or preventing Growth Factor Inhibitor (GFI) resistance in a cell, or, a method for increasing the growth-inhibiting effectiveness of a Growth Factor inhibitor on a cell, or, a method for re-sensitizing a cell to a Growth Factor Inhibitor (GFI). In alternative embodiments, the cell is a tumor cell, a cancer cell or a dysfunctional cell. In alternative embodiments, the invention provides compositions and methods for determining: whether an individual or a patient would benefit from or respond to administration of a Growth Factor Inhibitor, or, which individuals or patients would benefit from a combinatorial approach comprising administration of a combination of: at least one growth factor and at least one compound, composition or formulation used to practice a method of the invention, such as an NfKb inhibitor.

We found that integrin anb3 is upregulated in cells that become resistant to Growth Factor inhibitors. Our findings demonstrate that integrin anb3 promotes de novo and acquired resistance to Growth factor inhibitors by interacting and activating RalB. RalB activation leads to the activation of Src and TBK1 and the downstream effectors NFKB and IRF3. We also found that depletion of RalB or its downstream signaling (Src/NFKB) in b3-positive cells overcomes resistance to growth factor inhibitors. This invention demonstrates that the integrin anb3/RalB signaling complex promotes resistance to growth factor inhibitors; and in alternative embodiments, integrin $\alpha_v\beta_3$ (anb3) and active RalB are used as biomarkers in patient samples to predict which patients will respond to growth factor inhibitors and which patients might rather benefit from alternative/combinatorial approaches such as a combination of growth factor inhibitors and NfKb inhibitors.

This invention for the first time identifies integrin $\alpha v\beta 3$ and active RalB as potential biomarker for tumors that are or have become (e.g., de novo and acquired) resistant to growth factors blockade. Accordingly, in alternative embodiments, the invention provides compositions and methods for the depletion of RalB, Src, NFkB and its downstream signaling effectors to sensitize $\alpha v\beta 3$-expressing tumors to growth factor blockade. These findings reveal a new role for integrin $\alpha v\beta 3$ in mediating tumor cell resistance to growth factor inhibition and demonstrate that targeting the $\alpha v\beta 3$/RalB/10 NfkB/Src signaling pathway will circumvent growth factor resistance of a wide range of cancers.

In alternative embodiments, any NF-kB inhibitor can be used to practice this invention, e.g., lenalidomide or (RS)-3-(4-amino- 1-oxo-3H-isoindol-2-yl)piperidine-2,6-dione, which can be REVLIMID™ (Celgene Corp., Summit, N.J.), or thalidomide, or any other derivative of thalidomide, or any composition having an equivalent activity.

In alternative embodiments, compositions and methods of the invention are used to sensitize tumors to drugs, e.g., such as erlotinib and lapatinib (which are commonly used to treat a wide range of solid tumors). We have shown that when tumors become resistant to these drugs they become very sensitive to NFkB inhibitors. Thus, in alternative embodiments, compositions and methods of the invention are used to sensitize tumors using NFkB inhibitors, such as e.g., lenalidomide or (RS)-3-(4-amino-1-oxo-3H-isoindol-2-yl) piperidine-2,6-dione or REVLIMID™, or a composition as listed in Table 1.

In alternative embodiments, compositions and methods of the invention are used to sensitize tumors using an IKK inhibitor, e.g., such as PS1145 (Millennium Pharmaceuticals, Cambridge, Mass.) (see e.g., Khanbolooki, et al., Mol Cancer Ther 2006; vol. 5:2251-2260; Published online Sep. 19, 2006; Yemelyanov, et al., Oncogene (2006) vol. 25:387-398; published online 19 Sep. 2005), or any I$\kappa$B$\alpha$ (nuclear factor of kappa light polypeptide gene enhancer in B-cells inhibitor, alpha) phosphorylation and/or degradation inhibitor, e.g., one or more compositions listed in Table 3.

In alternative embodiments, compositions and methods of the invention comprise use of an NFkB inhibitor and an IKK inhibitor to treat a drug resistant tumor, e.g., a solid tumor. In alternative embodiments, compositions and methods of the invention comprise use of an NFkB inhibitor and an IKK inhibitor to treat a drug resistant tumor in combination with an anticancer drug, e.g., an NFkB inhibitor and an IKK inhibitor are used to sensitize a tumor to drugs such as erlotinib and lapatinib. In alternative embodiments, the drug combination used to practice the invention comprises lenalidomide (such as a REVLIMID™) and the IKK inhibitor PS1145 (Millennium Pharmaceuticals, Cambridge, Mass.). For example, lenalidomide (such as a REVLIMID™) and PS1145 are used to sensitize a tumor that is resistant to a cancer drug, e.g., an EGFR inhibitor, such that the tumor is now responsive to the cancer drug.

In alternative embodiments, in practicing the invention, an NFkB inhibitor and an IKK inhibitor are used in combination with a tyrosine kinase receptor (also called Receptor Tyrosine Kinases, or RTKs) inhibitor, e.g., an SU14813 (Pfizer, San Diego, Calif.) or as listed in Table 2 or 3, below, to treat a drug resistant tumor. In alternative embodiments, compositions and methods of the invention (e.g., including lenalidomide or PS1145; lenalidomide and PS1145; or lenalidomide, PS1145 and an RTK inhibitor are administered to patients that have become resistant to a cancer drug, e.g., drugs like erotinib or lapatinib, to produce a strong antitumor effect.

In alternative embodiments, any NF-kB inhibitor can be used to practice this invention, e.g., an antioxidant can be used to inhibit activation of NF-kB, e.g., including the compositions listed in Table 1:

TABLE 1

Antioxidants that have been shown to inhibit activation of NF-kB

| Molecule | Reference |
|---|---|
| a-Lipoic acid | Sen et al, 1998; Suzukiet al, 1992 |
| a-tocopherol | Islam et al, 1998 |
| Aged garlic extract (allicin) | Ide & Lau, 2001; Langet al, 2004; Hasan et al, 2007 |

TABLE 1-continued

Antioxidants that have been shown to inhibit activation of NF-kB

| Molecule | Reference |
| --- | --- |
| 2-Amino-1-methyl-6-phenylimidazo[4,5-b]pyridine (PhIP) | Yun et al, 2005 |
| N-acetyldopamine dimers (from *P. cicadae*) | Xu et al, 2006 |
| Allopurinol | Gomez-Cabrera et al, 2006 |
| Anetholdithiolthione | Sen et al, 1996 |
| Apocynin | Barbieri et al, 2004 |
| Apple juice/extracts | Shi & Jiang, 2002; Daviset al, 2006; Jung et al, 2009 |
| Aretemsia p7F (5,6,3',5'-tetramethoxy 7,4'-hydroxyflavone) | Lee et al, 2004 |
| Astaxanthin | Lee et al, 2003 |
| Autumn olive extracts; olive leaf extracts | Wang et al, 2007; Wanget al, 2008 |
| Avenanthramides (from oats) | Guo et al, 2007; Sur et al, 2008 |
| Bamboo culm extract | Lee et al, 2008 |
| Benidipine | Matsubara & Hazegawa, 2004 |
| bis-eugenol | Murakami et al, 2003 |
| *Bruguiera gymnorrhiza* compounds | Homhual et al, 2006 |
| Butylated hydroxyanisole (BHA) | Israël et al, 1992; Schulze-Osthoffet al, 1993 |
| Cepharanthine | Okamoto et al, 1994; Tamatani et al, 2007 |
| Caffeic Acid Phenethyl Ester (3,4-dihydroxycinnamic acid, CAPE) | Natarajan et al, 1996; Nagasaka et al, 2007 |
| Carnosol | Lo et al, 2002; Huang et al, 2005 |
| beta-Carotene | Bai et al, 2005; Guruvayoorappan& Kuttan, 2007 |
| Carvedilol | Yang et al, 2003 |
| Catechol Derivatives | Suzuki & Packer, 1994; Zheng et al, 2008 |
| *Centaurea L* (Asteraceae) extracts | Karamenderes et al, 2007 |
| Chalcone | Liu et al, 2007 |
| Chlorogenic acid | Feng et al, 2005 |
| 5-chloroacetyl-2-amnio-1,3-selenazoles | Nam et al, 2008 |
| Cholestin | Lin et al, 2007 |
| Chroman-2-carboxylic acid N-substituted phenylamides | Kwak et al, 2008 |
| Cocoa polyphenols | Lee et al, 2006 |
| Coffee extract (3-methyl-1,2-cyclopentanedione) | Chung et al, 2007 |
| *Crataegus pinnatifida* polyphenols | Kao et al, 2007 |
| Curcumin (Diferulolylmethane); dimethoxycurcumin; EF24 analog | Singh & Aggarwal, 1995; Pae et al, 2008; Kasinskiet al, 2008 |
| Dehydroepiandrosterone (DHEA) and DHEA-sulfate (DHEAS) | Iwasaki et al, 2004; Liuet al, 2005 |
| Dibenzylbutyrolactone lignans | Cho et al, 2002 |
| Diethyldithiocarbamate (DDC) | Schreck et al, 1992 |
| Diferoxamine | Sappey et al, 1995; Schreck et al, 1992 |
| Dihydroisoeugenol; isoeugenol; epoxypseudoisoeugenol-2-methyl butyrate | Murakami et al, 1995; Park et al, 2007; Ma et al, 2008 |
| Dihydrolipoic Acid | Suzuki et al, 1992, 1995 |
| Dilazep + fenofibric acid | Sonoki et al, 2003; Yanget al, 2005 |
| Dimethyldithiocarbamates (DMDTC) | Pyatt et al, 1998 |
| Dimethylsulfoxide (DMSO) | Kelly et al, 1994 |
| Disulfiram | Schreck et al, 1992 |
| Ebselen | Schreck et al, 1992 |
| Edaravone | Kokura et al, 2005; Ariiet al, 2007; Yoshida et al, 2007 |
| EPC-K1 (phosphodiester compound of vitamin E and vitamin C) | Hirano et al, 1998 |
| Epigallocatechin-3-gallate (EGCG; green tea polyphenols) | Lin & Lin, 1997; Yanget al,1998; Hou et al, 2007 |
| Ergothioneine | Rahman et al, 2003 |
| Ethyl Pyruvate (Glutathione depletion) | Song et al, 2004; Tsunget al, 2005; Jimenez-Lopezet al, 2008 |
| Ethylene Glycol Tetraacetic Acid (EGTA) | Janssen et al, 1999 |
| Eupatilin | Lee et al, 2008 |
| Exercise | Goto et al, 2007 |
| Fisetin | Park et al, 2006; Sunget al, 2007 |
| Flavonoids (*Crataegus*; *Boerhaavia diffusa* root; xanthohumol; *Eupatorium* arnottianum; genistein; kaempferol; quercetin, daidzein; flavone; isorhamnetin; naringenin; pelargonidin; finestin; *Sophora flavescens*; Seabuckthorn fruit berry) | Zhang et al, 2004; Chenet al, 2004; Pandey et al, 2005; Albini et al, 2005; Colgate et al, 2006; Clavin et al, 2007; Hamalainen et al, 2008; Zheng et al, 2008; Junget al, 2008; Mishra et al, 2008 |
| Folic acid | Au-Yeung et al, 2006 |

TABLE 1-continued

Antioxidants that have been shown to inhibit activation of NF-kB

| Molecule | Reference |
|---|---|
| Gamma-glutamylcysteine synthetase (gamma-GCS) | Manna et al, 1999 |
| *Ganoderma lucidum* polysaccharides | Zhang et al, 2003; Ho et al, 2007 |
| Garcinol (from extract of *Garcinia indica* fruit rind) | Liao et al, 2004 |
| *Ginkgo biloba* extract | Chen et al, 2003 |
| Glutathione | Cho et al, 1998; Schrecket al, 1992; Wang et al, 2007 |
| Guaiacol (2-methoxyphenol) | Murakami et al, 2007 |
| Hematein | Choi et al, 2003 |
| Hinokitiol | Byeon et al, 2008 |
| HMCO5 herbal extract | Kim et al, 2007 |
| Hydroquinone | Pyatt et al, 1998; Yanget al, 2006 |
| 23-hydroxyursolic acid | Shin et al, 2004 |
| IRFI 042 (Vitamin E-like compound) | Altavilla et al, 2001 |
| Iron tetrakis | Kang et al, 2001 |
| Isosteviol | Xu et al, 2008 |
| Isovitexin | Lin et al, 2005 |
| Isoliquiritigenin | Kumar et al, 2007; Kimet al, 2008; Kim et al, 2008 |
| *Justicia gendarussa* root extract | Kumar et al, 2011 |
| Kallistatin | Shen et al, 2008 |
| Kangen-karyu extract | Satoh et al, 2005; Yokozawa et al, 2007 |
| L-cysteine | Mihm et al, 1991 |
| Lacidipine | Cominacini et al, 1997 |
| Lazaroids | Marubayashi et al, 2002 |
| Ligonberries | Wang et al, 2005 |
| Lupeol | Saleem et al, 2004; Leeet al, 2007 |
| Lutein | Kim et al, 2008 |
| Magnolol | Chen et al, 2002; Ou et al, 2006; Kim et al, 2007 |
| Maltol | Yang et al, 2006 |
| Manganese superoxide dismutase (Mn-SOD) | Manna et al, 1998 |
| Extract of the stem bark of *Mangifera indica* L. | Leiro et al, 2004; Garridoet al, 2005 |
| Melatonin | Gilad et al, 1998; Mohanet al, 1995; Li et al, 2005 |
| 21 (alpha, beta)-methylmelianodiol | Zhou et al, 2007 |
| Mulberry anthocyanins | Chen et al, 2006 |
| N-acetyl-L-cysteine (NAC) | Schreck et al, 1991 |
| Nacyselyn (NAL) | Antonicelli et al, 2002 |
| Nordihydroguaiaritic acid (NDGA) | Brennan & O'Neill, 1998; Israël et al,1992; Schulze-Osthoff et al, 1993; Staalet al, 1993 |
| Ochnaflavone | Suh et al, 2006 |
| Onion extract (2,3-dihydro-3,5-dihydroxy-6-methyl-4H-pyranone) | Ban et al, 2007; Tang et al, 2008 |
| Orthophenanthroline | Schreck et al, 1992 |
| N-(3-oxo-dodecanoyl) homoserine lactone | Kravchenko et al, 2008 |
| Paricalcitol | Tan et al, 2008 |
| Phenolic antioxidants (Hydroquinone and tert-butyl hydroquinone) | Ma et al, 2003 |
| alkenylphenols from *Piper obliquum* | Valdivia et al, 2008 |
| alpha-phenyl-n-tert-butyl-nitrone (PEN) | Kotake et al, 1998; Linet al, 2006 |
| Phenylarsine oxide (PAO, tyrosine phosphatase inhibitor) | Arbault et al, 1998 |
| *Phyllanthus urinaria* | Chularojmontri et al, 2005; Shen et al, 2007 |
| Phytosteryl ferulates (rice bran) | Islam et al, 2008; Junget al, 2008 |
| *Piper longum* Linn, extract | Singh et al, 2007 |
| Pitavastatin | Tounai et al, 2007; Wang& Kitajima, 2007 |
| Prodelphinidin B2 3, 3' di-O-gallate | Hou et al, 2007 |
| Pterostilbene | Cichocki et al, 2008; Panet al, 2009 |
| Pyrrolinedithiocarbamate (PDTC) | Schreck et al, 1992 |
| Quercetin | Musonda & Chipman, 1998; Shih et al, 2004; Garcia-Mediavillaet al, 2006; Ruiz et al, 2007; Min et al, 2007; Kim et al, 2007 |
| Red orange extract | Cimini et al, 2008 |
| Red wine | Blanco-Colio et al, 2000; Cui & He, 2004 |
| Ref-1 (redox factor 1) | Ozaki et al, 2002 |
| Rg(3), a ginseng derivative | Keum et al, 2003 |
| Rotenone | Schulze-Osthoff et al, 1993 |
| Roxithromycin | Ueno et al, 2005; Ou et al, 2008 |

TABLE 1-continued

Antioxidants that have been shown to inhibit activation of NF-kB

| Molecule | Reference |
| --- | --- |
| Rutin | Kyung et al, 2008 |
| S-allyl-cysteine (SAC, garlic compound) | Geng et al, 1997 |
| Salogaviolide (*Centaurea ainetensis*) | Ghantous et al, 2008 |
| Sauchinone | Lee et al, 2003; Hwang et al, 2003 |
| Schisandrin B | Giridharan et all, 2011 |
| Silybin | Gazak et al, 2007 |
| Spironolactone | Han et al, 2006 |
| Strawberry extracts | Wang et al, 2005 |
| Taxifolin | Wang et al, 2005 |
| Tempol | Cuzzocrea et al, 2004 |
| Tepoxaline (5-(4-chlorophenyl)-N-hydroxy-(4-methoxyphenyl) -N-methyl-1H-pyrazole-3-propanamide) | Kazmi et al, 1995; Ritchieet al, 1995 |
| Thio avarol derivatives | Amigo et al, 2007; Amigoet al, 2008 |
| Thymoquinone | El Gazzar et al, 2007; lSethi et al, 2008 |
| Tocotrienol (palm oil) | Wu et al, 2008 |
| Tomato peel polysaccharide | De Stefano et al, 2007 |
| UDN glycoprotein (*Ulmus davidiana* Nakai) | Lee & Lim, 2007 |
| *Vaccinium stamineum* (deerberry) extract | Wang et al, 2007 |
| Vanillin (2-hydroxy-3-methoxybenzaldehyde) | Murakami et al, 2007 |
| Vitamin C | Staal et al, 1993; Son et al, 2004 |
| Vitamin B6 | Yanaka et al, 2005 |
| Vitamin E and derivatives | Suzuki & Packer, 1993; Ekstrand-Hammarstrom et al, 2007; Glauert, 2007 |
| a-torphryl succinate | Staal et al, 1993; Suzuki & Packer, 1993 |
| a-torphryl acetate | Suzuki & Packer, 1993 |
| PMC (2,2,5,7,8-pentamethyl-6-hydroxychromane) | Suzuki & Packer, 1993 |
| Yakuchinone A and B | Chun et al, 2002 |

In alternative embodiments, any proteasome inhibitor and/or protease inhibitor can be used to practice the invention, e.g., any proteasome inhibitor and/or protease inhibitor that can inhibit Rel and/or NF-kB can be used to practice this invention, e.g., including the compositions listed in Table 2:

TABLE 2

Proteasome and proteases inhibitors that inhibit Rel/NF-kB

| Molecule | References |
| --- | --- |
| Proteasome inhibitors | |
| Peptide Aldehydes: | Palombella et al, 1994; Grisham et al, 1999; Jobin et al, 1998 |
| ALLnL (N-acetyl-leucinyl-leucynil-norleucynal, MG101) | |
| LLM (N-acetyl-leucinyl-leucynil-methional) | |
| Z-LLnV (carbobenzoxyl-leucinyl-leucynil-norvalinal, MG115) | |
| Z-LLL (carbobenzoxyl-leucinyl-leucynil-leucynal, MG132) | |
| Lactacystine, beta-lactone | Fenteany & Schreiber, 1998; Grisham et al, 1999 |
| Boronic Acid Peptide | Grisham et al, 1999; Iqbal et al, 1995 |
| Dithiocarbamate complexes with metals | Cvek & Dvorak, 2007 |
| CEP-18770 | Piva et al, 2007 |
| Ubiquitin Ligase Inhibitors | Yaron et al, 1997 |
| PS-341 (Bortezomib) | Adams, 2004 |
| Salinosporamide A (1, NPI-0052) | Macherla et al, 2005; Ahn et al, 2007 |
| Cyclosporin A | Frantz et al, 1994; Kunz et al, 1995; Marienfeld et al, 1997; McCaffrey et al, 1994; Meyer et al, 1997; Wechsler et al, 1994 |

TABLE 2-continued

Proteasome and proteases inhibitors that inhibit Rel/NF-kB

| Molecule | References |
|---|---|
| FK506 (Tacrolimus) | Okamoto et al, 1994; Venkataramen et al, 1995 |
| Deoxyspergualin | Tepper et al, 1995 |
| Disulfiram | Lovborg et al, 2005 |
| PT-110 | Momose et al, 2007 |

Protease inhibitors

| Molecule | References |
|---|---|
| APNE (N-acetyl-DL-phenylalanine-b-naphthylester) | Higuchi et al, 1995 |
| BTEE (N-benzoyl L-tyrosine-ethylester) | Rossi et al, 1998 |
| DCIC (3,4-dichloroisocoumarin) | D'Acquisto et al, 1998 |
| DFP (diisopropyl fluorophosphate) | |
| TPCK (N-a-tosyl-L-phenylalanine chloromethyl ketone) | |
| TLCK (N-a-tosyl-L-lysine chloromethyl ketone) | |

In alternative embodiments, any IκBα (nuclear factor of kappa light polypeptide gene enhancer in B-cells inhibitor, alpha) phosphorylation and/or degradation inhibitor can be used to practice this invention, e.g., including the compositions listed in Table 3:

TABLE 3

IκBα phosphorylation and/or degradation inhibitors

| Molecule | Point of Inhibition | References |
|---|---|---|
| Desloratadine; diphenhydramine | Histamine H1 receptor | Wu et al, 2004; Scadding, 2005; Roumestan et al, 2008 |
| Bikunin | LPS receptor agonists | Kobayashi, 2006; Kanayama et al, 2007 |
| Ron Tyrosine kinase receptor | Suppresses TNF production | Lentsch et al, 2007 |
| TAK-242 | TLR4 intracellular domain | Kawamoto et al, 2008 |
| Salmeterol, fluticasone propionate | beta2 agonists | Baouz et al, 2005 |
| CPU0213 | Endothelin receptor antagonist | He et al, 2006 |
| Doxazosin | alpha1-adrenergic receptor antagonist | Hui et al, 2007 |
| Erbin overexpression | NOD2 inhibitor | McDonald et al, 2005 |
| Protein-bound polysaccharide from basidiomycetes | LPS-CD14 interaction | Asai et al, 2005 |
| Anti-CD 146 antibody AA98 | upstream of IKK | Bu et al, 2006 |
| Calagualine (fern derivative) | upstream of IKK (TRAF2-NIK) | Manna et al, 2003 |
| NS3/4A (HCV protease) | upstream of IKK | Karayiannis, 2005 |
| golli BG21 (product of myelin basic protein) | upstream of IKK (PKC) | Feng et al, 2004 |
| NPM-ALK oncoprotein | Traf2 inhibition | Horie et al, 2004 |
| NS5A (Hepatitis C virus) | Traf2 inhibition | Park et al, 2002 |
| LY29 and LY30 | PI3 Kinase inhibitors | Choi et al, 2004 |
| Shiga toxin (Enterohemorrhagic E coli) | PI3 Kinase inhibitor | Gobert et al, 2007 |
| Evodiamine (Evodiae Fructus component) | AKT-IKK interaction | Takada et al, 2005 |
| Rituximab (anti-CD20 antibody) | up-regulates Raf-1 kinase inhibitor | Jazirehi et al, 2005 |
| Kinase suppressor of ras (KSR2) | MEKK3 inhibitor | Channavajhala et al, 2005 |
| Cholecystokinin ocatpeptide (CCK-8) | p38 kinase | Li et al, 2007 |
| M2L (Vaccinia virus) | ERK2 inhibitor | Gedey et al, 2006; Hinthong et al, 2008 |
| Pefabloc (serine protease inhibitor) | upstream of IKK | Tando et al, 2002 |
| Rocaglamides (Aglaia derivatives) | upstream of IKK | Baumann et al, 2002 |
| Ymer | Binds to Ub-RIP | Bohgaki et al, 2007 |
| Epoxyquinol B | TAK1 crosslinker | Kamiyama et al, 2008 |
| Betaine | NIK/IKK | Go et al, 2004, 2007 |
| TNAP | NIK | Hu et al, 2005 |

TABLE 3-continued

IκBα phosphorylation and/or degradation inhibitors

| Molecule | Point of Inhibition | References |
|---|---|---|
| Selected peptides | NEMO binding to Ub | Wyler et al, 2007 |
| Desflurane | IKK complex formation with TNF-R1 | Li et al, 2008 |
| Geldanamycin | IKK complex formation | Chen et al, 2002 |
| Grape seed proanthocyanidins | IKKa activity | Mantena & Katiyar, 2006; Sharma et al, 2007; Cheng et al, 2007; Xu et al, 2008 |
| Laretia acaulis azorellane diterpenoids | IKKa activity | Borquez et al, 2007 |
| MC160 (Molluscum contagiosum virus) | IKKa activity | Nichols & Shisler, 2006 |
| NS5B (Hepatitis C protein) | IKKa activity | Choi et al, 2006 |
| Pomegranate fruit extract | IKKa activity | Afaq et al, 2004; Khan et al, 2006 |
| Tetrandine (plant alkaloid) | IKKa activity | Ho et al, 2004; Xueet al, 2008; Lin et al, 2008 |
| BMS-345541 (4(2'-Aminoethyl)amino-1,8-dimethylimidazo(1,2-a)quinoxaline) and 4-amino derivatives | IKKa and IKKb kinase activity | Burke et al, 2002; Yang et al, 2006; Beaulieu et al, 2006 |
| 1-O-acetylbritannilactone | IKKb activity | Liu et al, 2007 |
| 2-amino-3-cyano-4-aryl-6-(2-hydroxy-phenyl)pyridine derivatives | IKKb activity | Murata et al, 2003, 2004, 2004 |
| Acrolein | IKKb activity/p50 DNA binding | Vallacchi et al, 2005; Lambert et al, 2007 |
| Anandamide | IKKb activity | Sancho et al, 2003 |
| AS602868 | IKKb activity | Frelin et al, 2003: Griessinger et al, 2007 |
| Cobrotoxin | IKKb activity/p50 DNA binding | Park et al, 2005 |
| Core protein (Hepatitis C) | IKKb activity | Joo et al, 2005; Shrivastava et al, 1998 |
| 1-[2-cyano-3,12-dioxooleana-1,9(11)-dien-28-oyl] imidazole | IKKb activity | Yore et al, 2006 |
| Dihydroxyphenylethanol | IKKb activity | Guichard et al, 2006 |
| Herbimycin A | IKKb activity | Iwasaki et al, 1992; Mahon & O'Neill, 1995; Ogino et al, 2004 |
| Inhibitor 22 | IKKb activity | Baxter et al, 2004 |
| Isorhapontigenin | IKKb activity | Li et al, 2005 |
| Manumycin A | IKKb activity | Bernier et al, 2005; Frassanito et al, 2005 |
| 6-methyl-2-propolyimino-6,7-dihydro-5H-benzo[1,3]oxathiol-4-one | IKKb | Kim et al, 2008 |
| MLB120 (small molecule) | IKKb activity | Nagashima et al, 2006 |
| Naphthopyrones (6-methoxycomaparvin and 6-methooxycomaparvin 5-methyl ether) | IKKb activity | Fulmer et al, 2008 |
| Novel Inhibitor | IKKb activity | Kamon et al, 2004 |
| vIRF3 (KSHV) | IKKb activity | Seo et al, 2004 |
| Nitric oxide | IKKb activity/IkB phosphorylation | Katsuyama et al, 1998; Matthews et al, 1996; Spieker & Liao, 1999; Reynaert et al, 2004 |
| SC-514 (small molecule) | IKKb activity | Kishore et al, 2003 |
| Thienopyridine | IKKb activity | Morwick et al, 2006 |
| Acetyl-boswellic acids | IKK activity | Syrovets et al, 2004, 2005 |
| Amino-pyrimidine derivative | IKK activity | Karin et al, 2004 |
| Benzoimidazole derivative | IKK activity | Karin et al, 2004 |
| BMS-345541 | IKK activity | Burke et al, 2003 |
| Butein | IKKb activity | Pandey et al, 2007 |
| Beta-carboline | IKK activity | Yoon et al, 2005 |
| CYL-19s and CYL-26z, two synthetic alpha-methylene-gamma-butyrolactone derivatives | IKK activity | Huang et al, 2004 |

TABLE 3-continued

IκBα phosphorylation and/or degradation inhibitors

| Molecule | Point of Inhibition | References |
|---|---|---|
| ACHP (2-amino-6-[2-(cyclopropylmethoxy)-6-hydroxyphenyl]-4-piperidin-4-yl nicotinonitrile | IKKb activity (ATP analog) | Sanda et al, 2006 |
| Berberine | IKKb activity | Hu et al, 2007; Yi et al, 2008; Pandey et al, 2008 |
| Compound A | IKKb activity (ATP analog) | Ziegelbauer et al, 2005 |
| Flavopiridol | IKK activity and RelA phosphor. | Takada & Aggarwal, 2003 |
| Cyclopentones | IKKb activity | Bickley et al, 2004 |
| Dehydroascorbic acid (Vitamin C) | IKKb activity | Carcamo et al, 2004 |
| Gossypyin or *Gossypium* extracts | IKKb activity | Kunnumakkara et al, 2007; Ji et al, 2008 |
| M protein (SARS-Cornonavirus protein) | IKKb activity | Fang et al, 2007 |
| IMD-0354 | IKKb activity | Tanaka et al, 2004, 2006; Inayama et al, 2006 |
| Jesterone dimer | IKKb activity; DNA binding | Liang et al, 2003, 2006 |
| KINK-1 | IKKb activity | Schon et al, 2008 |
| LCY-2-CHO | IKKb activity | Ho et al, 2007 |
| Prolyl hydroxylase-1 | IKKb activity | Cummins et al, 2006 |
| Naphthopyrones (Echinoderm *Comanthus parvicirrus*) | IKKb activity | Folmer et al, 2007 |
| Neuropeptides CGRP, PACAP and VIP | IKKb activity | Ding et al, 2007 |
| PS-1145 (MLN1145) | IKKb activity | Hideshima et al, 2002 |
| 2-[(aminocarbonyl)amino]-5-(4-fluorophenyl)-3-thiophenecarboxamides (TPCA-1) | IKKb activity | Bonafoux et al, 2005; Podolin et al, 2005 |
| 1'-Acetoxychavicol acetate (*Languas galanga*) | IKK activity | Ichikawa et al, 2005; Ito et al, 2005 |
| 17-Acetoxyjolkinolide B | IKK activity | Yan et al, 2008 |
| Acute alcohol exposure | IKK activity | Mandrekar et al, 2007 |
| Anacardic acid (6-nonadecyl-salicylic acid) | IKK activity | Sung et al, 2008 |
| Apigenin (plant flavinoid) | IKK activity | Shukla & Gupta, 2004; Yoon et al, 2006 |
| Asiatic acid | IKK activity | Yun et al, 2008 |
| Cardamomin | IKK activity | Lee et al, 2005 |
| CDDO-Me (synthetic triterpenoid) | IKK activity | Shishodia et al, 2006 |
| CHS 828 (anticancer drug) | IKK activity | Olsen et al, 2004 |
| CML-1 | IKK activity | Mo et al, 2006 |
| Compound 5 (Uredio-thiophenecarboxamide derivative) | IKK activity | Roshak et al, 2002 |
| CT20126 | IKK activity/NIK | Lee et al, 2008 |
| Diaylpyridine derivative | IKK activity | Murata et al, 2003 |
| 3,4-dihydroxybenzalacetone (from Chaga) | IKK activity | Sung et al, 2008 |
| Diosgenin | IKK activity | Shishodia & Aggarwal, 2005; Liagre et al, 2005 |
| E3-14.7K (Adenovirus) | IKK activity | Li et al, 1999 |
| E3-10.4K/14.5K (Adenovirus) | IKK activity | Friedman & Horwitz, 2002 |
| E7 (*human papillomavirus*) | IKK activity | Spitkovsky et al, 2002 |
| Furonaphthoquinone | IKK activity | Shin et al, 2006 |
| 3-Formylchromone | IKKb activity/p65 DNA binding | Yadav et al, 2011 |
| Guggulsterone | IKK activity | Ichikawa & Aggarwal, 2006; Deng, 2007; Lv et al, 2008; Lee et al, 2008 |
| HB-EGF (Heparin-binding epidermal growth factor-like growth factor) | IKK activity | Mehta & Besner, 2003 |
| Falcarindol | IKK activity | Shiao et al, 2005 |
| Hammerhead ribozyme to IKKa/b | IKK activity | Yang et al, 2007 |
| Hepatocyte growth factor | IKK activity | Min et al, 2005; Gong et al, 2006 |
| Honokiol | IKK activity | Tse et al, 2005; Munroe et al, 2007 |

TABLE 3-continued

IκBα phosphorylation and/or degradation inhibitors

| Molecule | Point of Inhibition | References |
|---|---|---|
| Humulone | IKK activity | Lee et al, 2007 |
| Hypoestoxide | IKK activity | Ojo-Amaize et al, 2001 |
| Indolecarboxamide derivative | IKK activity | Karin et al, 2004 |
| Labdane diterpenoids | IKK activity | Giron et al, 2008 |
| LF15-0195 (analog of 15-deoxyspergualine) | IKK activity | Yang et al, 2003 |
| gamma-mangostin (from *Garcinia mangostana*) | IKK activity | Nakatani et al, 2004 |
| Garcinone B | IKK activity | Yamakuni et al, 2005 |
| (Amino)imidazolylcarboxaldehyde derivative | IKK activity | Karin et al, 2004 |
| Imidazolylquinoline-carboxaldehyde derivative | IKK activity | Karin et al, 2004 |
| Kahweol | IKK activity | Kim et al, 2004 |
| Kava (*Piper methysticum*) derivatives | IKK activity | Folmer et al, 2006 |
| Lead | IKK activity | Xu et al, 2006 |
| *Marasmius oreades* liquid extract | IKK activity | Petrova et al, 2008 |
| Menatetrenone (vitamin K2 analogue) | IKK activity | Ozaki et al, 2007 |
| Metformin | IKK activity | Huang et al, 2008 |
| Mild hypothermia | IKK activity | Han et al, 2003 |
| ML120B | IKK activity | Catley et al, 2006 |
| Morin (3,5,7,2',4'-Pentahydroxyflavone) | IKK activity | Manna et al, 2007 |
| Morusin | IKK activity | Lee et al, 2008 |
| MX781 (retinoid antagonist) | IKK activity | Bayon et al, 2003 |
| N-acetylcysteine | IKK activity | Oka et al, 2000 |
| Nitrosylcobalamin (vitamin B12 analog) | IKK activity | Chawla-Sarkar et al, 2003 |
| NSAIDs | IKK activity | Takada et al, 2004 |
| Hepatits C virus NS5B | IKK activity | Choi et al, 2006 |
| PAN1 (aka NALP2 or PYPAF2) | IKK activity | Bruey et al, 2004 |
| Pectin (citrus) | IKK activity | Chen et al, 2006 |
| Pinitol | IKK activity | Sethi et al, 2008 |
| PMX464 | IKK activity | Callister et al, 2008 |
| Pyrazolo[4,3-c]quinoline derivative | IKK activity | Karin et al, 2004 |
| Pyridooxazinone derivative | IKK activity | Karin et al, 2004 |
| N-(4-hydroxyphenyl) retinamide | IKK activity | Shishodia et al, 2005; Kuefer et al, 2007 |
| Scytonemin | IKK activity | Stevenson et al, 2002 |
| *Semecarpus anacardiu* extract | IKK activity | Singh et al, 2006 |
| SPC-839 | IKK activity | Palanki et al, 2002 |
| Sulforaphane and phenylisothiocyanate | IKK activity | Xu et al, 2005; Murakami et al, 2007; Liu et al, 2008: Hayes et al, 2008 |
| Survanta (Surfactant product) | IKK activity | Raychaudhuri et al, 2003 |
| Torque Teno virus ORF2 | IKK activity | Zheng et al, 2007 |
| Piceatannol | IKK activity | Islam et al, 2004 |
| Plumbagin (5-hydroxy-2-methyl-1,4-naphthoquinone) | IKK activity | Sandur et al, 2006 |
| IKKb peptide to NEMO binding domain | IKK-NEMO interaction | May et al, 2000 |
| NEMO CC2-LZ peptide | NEMO oligomerization | Agou et al, 2004 |
| AGRO100 (G-quadraplex oligodeoxynucleotide) | NEMO binding | Girvan et al, 2006 |
| PTEN (tumor suppressor) | Activation of IKK | Gustin et al, 2001 |
| Theaflavin (black tea component) | Activation of IKK | Aneja et al, 2004; Ukil et al, 2006; Kalra et al, 2007 |
| Tilianin | Activation of IKK | Nam et al, 2005 |
| Withanolides | Activation of IKK | Ichikawa et al, 2006 |
| Zerumbone | Activation of IKK | Takada et al, 2005 |
| Silibinin | IKKa activity; nuclear translocation | Dhanalakshmi et al, 2002; Singh et al, 2004; Min et al, 2007 |
| Sulfasalazine | IKKa and IKKb kinase activity | Wahl et al, 1998: Weber et al, 2000 |
| Sulfasalazine analogs | IKK kinase activity | Habens et al, 2005 |
| Quercetin | IKK activity | Peet & Li, 1999 |
| Rosmarinic acid | IKK activity | Lee et al, 2006 |
| Staurosporine | IKK activity | Peet & Li, 1999 |
| gamma-Tocotrienol | IKK activity | Shah & Sylvester, 2005; Ahn et al, 2006 |

TABLE 3-continued

IκBα phosphorylation and/or degradation inhibitors

| Molecule | Point of Inhibition | References |
| --- | --- | --- |
| Wedelolactone | IKK activity | Kobori et al, 2003 |
| Betulinic acid | IKKa activity and p65 phosphorylation | Takada & Aggarwal, 2003; Rabi et al, 2008 |
| Ursolic acid | IKKa activity and p65 phosphorylation | Shishodia et al, 2003; Manu & Kuttan, 2008 |
| Thalidomide (and thalidomide analogs) | IKK activity | Keifer et al, 2001; Ge et al, 2006; Carcache de-Blanco et al, 2007 |
| Salubrinal | IKK activity/degradation | Huang et al, 2011 |
| Fas-associated factor-1 | IKK assembly | Park et al, 2007 |
| Interleukin-10 | Reduced IKKa and IKKb expression | Tabary et al, 2003 |
| MC160 (molluscum contagiosum virus) | Reduced IKKa expression | Nichols & Shisler, 2006 |
| Monochloramine and glycine chloramine (NH2Cl) | Oxidizes IkB | Kim et al, 2005; Midwinter et al, 2006 |
| GS143 | Blocks IkB ubiquitylation | Nakajima et al, 2008; Hirose et al, 2008 |
| *Salmonella* Secreted Factor L | Blocks IkB ubiquitylation | Le Negrate et al, 2008 |
| Anethole | Phosphorylation | Chainy et al, 2000 |
| Anti-thrombin III | Phosphorylation | Oelschlager et al, 2002 |
| *Artemisia vestita* | Phosphorylation | Sun et al, 2006 |
| Aspirin, sodium salicylate | Phosphorylation, IKKbeta | Frantz & O'Neill, 1995; Kopp & Ghosh, 1994; Yin et al, 1998 |
| Azidothymidine (AZT) | Phosphorylation | Ghosh et al, 2003; Kurokawa et al, 2005 |
| Baoganning | Phosphorylation | Tan et al, 2005 |
| BAY-11-7082 (E3((4-methylphenyl)-sulfonyl)-2-propenenitrile) | Phosphorylation | Pierce et al, 1997 |
| BAY-117083 (E3((4-t-butylphenyl)-sulfonyl)-2-propenenitrile) | Phosphorylation | Pierce et al, 1997 |
| Benzyl isothiocyanate | Phosphorylation | Srivastava & Singh, 2004 |
| Black raspberry extracts (cyanidin 3-O-glucoside, cyanidin 3-O-(2(G)-xylosylrutinoside), cyanidin 3-O-rutinoside) | Phosphorylation | Huang et al, 2002; Hecht et al, 2006 |
| Buddlejasaponin IV | Phosphorylation | Won et al, 2006 |
| Cacospongionolide B | Phosphorylation | Posadas et al, 2003 |
| Calagualine | Phosphorylation | Manna et al, 2003 |
| Carbon monoxide | Phosphorylation | Sarady et al, 2002 |
| Carboplatin | Phosphorylation | Singh & Bhat, 2004 |
| Cardamonin | Phosphorylation | Israf et al, 2006 |
| Chorionic gonadotropin | Phosphorylation | Manna et al, 2000 |
| Cordycepin | Phosphorylation | Kim et al, 2006; Huang et al., 2007 |
| Crassocephalum rabens galactolipid | Phosphorylation | Hou et al., 2007 |
| Cycloepoxydon; 1-hydroxy-2-hydroxymethyl-3-pent-1-enylbenzene | Phosphorylation | Gehrt et al, 1998 |
| Cytomegalovirus | Phosphorylation | Jarvis et al, 2006 |
| Decursin | Phosphorylation | Kim et al, 2006 |
| Delphinidin | Phosphorylation | Syed et al, 2008 |
| Dexanabinol | Phosphorylation | Juttler et al, 2004 |
| Digitoxin | Phosphorylation | Srivastava et al, 2004; Jagielska et al, 2009 |
| Dihydrotestosterone | Phosphorylation | Xu et al, 2011 |
| Diterpenes (synthetic) | Phosphorylation | Chao et al, 2005 |
| Docosahexaenoic acid | Phosphorylation | Chen et al, 2005; Zand et al, 2008 |
| *Entamoeba histolytica* | Phosphorylation | Kammanadiminti & Chadee, 2006 |
| Extensively oxidized low density lipoprotein (ox-LDL), 4-Hydroxynonenal (HNE) | Phosphorylation | Brand et al, 1997; Page et al, 1999 |

TABLE 3-continued

| IκBα phosphorylation and/or degradation inhibitors | | |
|---|---|---|
| Molecule | Point of Inhibition | References |
| FBD | Phosphorylation | Lin et al, 2008 |
| FHIT (Fragile histidine triad protein) | Phosphorylation | Nakagawa & Akao, 2006 |
| *Fructus Ligustrum lucidi* | Phosphorylation | An et al, 2007 |
| Gabexate mesilate | Phosphorylation | Uchiba et al, 2003 |
| [6]-gingerol; casparol | Phosphorylation | Kim et al, 2005; Aktan et al, 2006; Ishiguro et al, 2007 |
| *Gleditsia sinensis* thorns extract | Phosphorylation | Ha et al, 2008 |
| Gleevec (Imatanib) | Phosphorylation | Wolf et al, 2005 |
| *Glossogyne tenuifolia* | Phosphorylation | Wu et al, 2004; Haet al, 2006 |
| Guggulsterone | Phosphorylation | Shishodia & Aggarwal, 2004 |
| 4-hydroxy-3,6,7,8,3',4'-hexamethoxyflavone | Phosphorylation | Lai et al, 2007 |
| Hydroquinone | Phosphorylation | Kerzic et al, 2003 |
| Ibuprofen | Phosphorylation | Palayoor et al, 1998 |
| Indirubin-3'-oxime | Phosphorylation | Mak et al, 2004 |
| *Inonotus obliquus* ethanol extract | Phosphorylation | Kim et al, 2007 |
| Interferon-alpha | Phosphorylation | Manna et al, 2000 |
| Inhaled isobutyl nitrite | Phosphorylation | Ponnappan et al, 2004 |
| Kaempferol | Phosphorylation | Garcia-Mediavilla et al, 2006; Kim et al, 2007 |
| Kushen flavonoids and kurarinone | Phosphorylation | Han et al, 2006 |
| Licorce extracts | Phosphorylation | Kim et al, 2006: Kwon et al, 2007 |
| Melatonin | Phosphorylation | Alonso et al, 2006; Tamura et al, 2009 |
| Marine natural products (several) | IKKb/proteasome | Folmer et al, 2009 |
| Methotrexate | Phosphorylation | Majumdar & Aggarwal, 2001; Yozai et al, 2005 |
| Monochloramine | Phosphorylation | Omori et al, 2002 |
| Nafamostat mesilate | Phosphorylation | Noguchi et al, 2003 |
| Obovatol | Phosphorylation | Lee et al, 2008 |
| Oleandrin | Phosphorylation | Manna et al, 2000; Sreeivasan et al, 2003 |
| Oleanolic acid (*Aralia elata*) | Phosphorylation | Suh et al, 2007 |
| Omega 3 fatty acids | Phosphorylation | Novak et al, 2003 |
| Panduratin A (from *Kaempferia pandurata*, Zingiberaceae) | Phosphorylation | Yun et al, 2003 |
| Petrosaspongiolide M | Phosphorylation | Posadas et al, 2003 |
| Pinosylvin | Phosphorylation | Lee et al, 2006 |
| *Plagius flosculosus* extract polyacetylene spiroketal | Phosphorylation | Calzado et al, 2005 |
| Phytic acid (inositol hexakisphosphate) | Phosphorylation | Ferry et al, 2002 |
| Pomegranate fruit extract | Phosphorylation | Ahmed et al, 2005 |
| Prostaglandin A1 | Phosphorylation/IKK | Rossi et al, 1997, 2000 |
| Protocatechuic Aldehyde | Phosphorylation | Xu et al, 2011 |
| 20(S)-Protopanaxatriol (ginsenoside metabolite) | Phosphorylation | Oh et al, 2004; Leeet al, 2005 |
| Rengyolone | Phosphorylation | Kim et al, 2006 |
| Rottlerin | Phosphorylation | Kim et al, 2005; Torricelli et al, 2008 |
| Saikosaponin-d | Phosphorylation; Increased IkB | Leung et al, 2005; Dang et al, 2007 |
| Saline (low Na+ istonic) | Phosphorylation | Tabary et al, 2003 |
| *Salvia miltiorrhizae* water-soluble extract | Phosphorylation | Kim et al, 2005 |
| Sanguinarine (pseudochelerythrine, 13-methyl-[1,3]-benzodioxolo-[5,6-c]-1,3-dioxolo-4,5 phenanthridinium) | Phosphorylation | Chaturvedi et al, 1997 |
| Scoparone | Phosphorylation | Jang et al, 2005 |
| Sesaminol glucosides | Phosphorylation | Lee et al, 2006 |
| Shikonins | Phosphorylation | Nam et al, 2008 |
| Silymarin | Phosphorylation | Manna et al, 1999; Saliou et al, 1998 |
| Snake venom toxin (*Vipera lebetina turanica*) | Phosphorylation | Son et al, 2007 |
| SOCS1 | Phosphorylation | Kinjyo et al, 2002; Nakagawa et al, 2002 |

TABLE 3-continued

IκBα phosphorylation and/or degradation inhibitors

| Molecule | Point of Inhibition | References |
| --- | --- | --- |
| Spilanthol | Phosphorylation | Wu et al, 2008 |
| Statins (several) | Phosphorylation | Hilgendorff et al, 2003; Han et al, 2004; Planavila et al, 2005 |
| Sulindac | IKK/Phosphorylation | Yamamoto et al, 1999 |
| THI 52 (1-naphthylethyl-6,7-dihydroxy-1,2,3,4-tetrahydroisoquinoline) | Phosphorylation | Kang et al, 2003 |
| 1,2,4-thiadiazolidine derivatives | Phosphorylation | Manna et al, 2004 |
| Tomatidine | Phosphorylation | Chiu & Lin, 2008 |
| Vesnarinone | Phosphorylation | Manna & Aggarwal, 2000; Harada et al, 2005 |
| Xanthoangelol D | Phosphorylation | Sugii et al, 2005 |
| YC-1 | Phosphorylation | Huang et al, 2005 |
| YopJ (encoded by *Yersinia pseudotuberculosis*) | Deubiquintinase for IkBa; Acetylation of IKKbeta | Schesser et al, 1998; Zhou et al, 2005; Mittal et al, 2006; Mukherjee & Orth, 2008 |
| Osmotic stress | IkB ubiquitination | Huangfu et al, 2007 |
| Acetaminophen | Degradation | Mancini et al, 2003 |
| Activated Protein C (APC) | Degradation | Yuksel et al, 2002 |
| Alachlor | Degradation | Shimomura-Shimizu et al, 2005 |
| Allylpyrocatechol | Degradation | Sarkar et al, 2008 |
| a-melanocyte-stimulating hormone (a-MSH) | Degradation | Manna & Aggarwal, 1998 |
| Amentoflavone | Degradation | Banerjee et al, 2002; Guruvayoorappan & Kuttan, 2007 |
| *Angelica dahurica* radix extract | Degradation | Kang et al, 2006 |
| Apple extracts | Degradation/proteasome | Yoon & Liu, 2007 |
| *Artemisia capillaris* Thunb extract (capillarisin) | Degradation | Hong et al, 2004; Kim et al, 2007; Leeet al, 2007 |
| *Artemisia iwayomogi* extract | Degradation | Kim et al, 2005 |
| L-ascorbic acid | Degradation | Han et al, 2004 |
| *Antrodia camphorata* | Degradation | Hseu et al, 2005 |
| Aucubin | Degradation | Jeong et al, 2002 |
| Baicalein | Degradation | Ma et al, 2004 |
| N-(quinolin-8-yl)benzenesulfonamindes | Degradation | Xie et al, 2007 |
| beta-lapachone | Degradation | Manna et al, 1999 |
| Blackberry extract | Degradation | Pergola et al, 2006 |
| 1-Bromopropane | Degradation | Yoshida et al, 2006 |
| Buchang-tang | Degradation | Shin et al, 2005 |
| Capsaicin (8-methyl-N-vanillyl-6-nonenamide) | Degradation | Singh et al, 1996; Mori et al, 2006; Kang et al, 2007 |
| Catalposide | Degradation | Kim et al, 2004 |
| *Clerodendron trichotomum* Tunberg Leaves | Degradation | Park & Kim, 2007 |
| Clomipramine/imipramine | Degradation | Hwang et al, 2008 |
| Coptidis rhizoma extract | Degradation | Kim et al, 2007 |
| Cyclolinteinone (sponge sesterterpene) | Degradation | D'Acquisto et al, 2000 |
| DA-9601 (Artemisia asiatica extract) | Degradation | Choi et al, 2006 |
| Diamide (tyrosine phosphatase inhibitor) | Degradation | Toledano & Leonard, 1991; Singh & Aggarwal, 1995 |
| Dihydroarteanniun | Degradation | Li et al, 2006 |
| Dobutamine | Degradation | Loop et al, 2004 |
| Docosahexaenoic acid | Degradation | Weldon et al, 2006 |
| E-73 (cycloheximide analog) | Degradation | Sugimoto et al, 2000 |
| Ecabet sodium | Degradation | Kim et al, 2003 |
| Electrical stimulation of vagus nerve | Degradation | Guarini et al, 2003 |
| Emodin (3-methyl-1,6,8-trihydroxyanthraquinone) | Degradation | Kumar et al, 1998; Huang et al, 2004 |
| Ephedrae herba (Mao) | Degradation | Aoki et al, 2005 |
| Equol | Degradation | Kang et al, 2005 |
| Erbstatin (tyrosine kinase inhibitor) | Degradation | Natarajan et al, 1998 |

TABLE 3-continued

IκBα phosphorylation and/or degradation inhibitors

| Molecule | Point of Inhibition | References |
|---|---|---|
| Estrogen (E2) | Degradation/and various other steps | Sun et al, 1998; Kalaitzidis & Gilmore, 2005; Steffan et al, 2006 |
| Ethacrynic acid | Degradation (and DNA binding) | Han et al, 2004 |
| Fludarabine | Degradation | Nishioka et al, 2007 |
| Fosfomycin | Degradation | Yoneshima et al, 2003 |
| Fungal gliotoxin | Degradation | Pahl et al, 1999 |
| Gabexate mesilate | Degradation | Yuksel et al, 2003 |
| Gamisanghyulyunbueum | Degradation | Shin et al, 2005 |
| Genistein (tyrosine kinase inhibitor) | Degradation; caspase cleavage of IkBa | Natarajan et al, 1998; Baxa & Yoshimura, 2003 |
| Genipin | Degradation | Koo et al, 2004 |
| Glabridin | Degradation | Kang et al, 2004 |
| Ginsenoside Re | Degradation | Zhang et al, 2007 |
| Glimepiride | Degradation | Schiekofer et al, 2003 |
| Glucosamine (sulfate or carboxybutyrylated) | Degradation | Largo et al, 2003; Rafi et al, 2007; Rajapakse et al, 2008 |
| gamma-glutamylcysteine synthetase | Degradation | Manna et al, 1999 |
| Glutamine | Degradation | Singleton et al, 2005; Fillmann et al, 2007; Chen et al, 2008 |
| Glycochenodeoxycholate | Degradation | Bucher et al, 2006 |
| Guave leaf extract | Degradation | Choi et al, 2008 |
| Gumiganghwaltang | Degradation | Kim et al, 2005 |
| Gum mastic | Degradation | He et al, 2007 |
| Heat shock protein-70 | Degradation | Chan et al, 2004; Shi et al, 2006 |
| Herbal mixture (Cinnamomi ramulus, Anemarrheriae rhizoma, Officinari rhizoma) | Degradation | Jeong et al, 2008 |
| Hypochlorite | Degradation | Mohri et al, 2002 |
| Ibudilast | Degradation | Kiebala & Maggirwar, 1998 |
| IL-13 | Degradation | Manna & Aggarwal, 1998 |
| Incensole acetate | Degradation | Moussaieff et al, 2007 |
| Intravenous immunoglobulin | Degradation | Ichiyama et al, 2004 |
| Isomallotochromanol and isomallotochromene | Degradation | Ishii et al, 2003 |
| K1L (Vaccinia virus protein) | Degradation | Shisler & Jin, 2004 |
| *Kochia scoparia* fruit (methanol extract) | Degradation | Shin et al, 2004 |
| *Kummerowia striata* (Thunb.) Schindl (ethanol extract) | Degradation | Tao et al, 2008 |
| Leflunomide metabolite (A77 1726) | Degradation | Manna & Aggarwal, 1999 |
| Lidocaine | Degradation | Feng et al, 2007; Lahat et al, 2008 |
| Lipoxin A4 | Degradation | Zhang et al, 2007 |
| Losartan | Degradation/NF-kB expression | Chen et al, 2002; Zhu et al, 2007 |
| Low level laser therapy | Degradation | Rizzi et al, 2006 |
| LY294002 (PI3-kinase inhibitor) [2-(4-morpholinyl)-8-phenylchromone] | Degradation | Park et al, 2002 |
| MC159 (Molluscum contagiosum virus) | Degradation of IkBb | Murao & Shisler, 2005 |
| Melatonin | Degradation | Zhang et al, 2004 |
| Meloxicam | Degradation | Liu et al, 2007 |
| 5'-methylthioadenosine | Degradation | Hevia et al, 2004 |
| Midazolam | Degradation | Kim et al, 2006 |
| Momordin I | Degradation | Hwang et al, 2005 |
| *Morinda officinalis* extract | Degradation | Kim et al, 2005 |
| *Mosla dianthera* extract | Degradation | Lee et al, 2006 |
| Mume fructus extract | Degradation | Choi et al, 2007 |
| Murr1 gene product | Degradation | Ganesh et al, 2003 |
| Neurofibromatosis-2 (NF-2; merlin) protein | Degradation | Kim et al, 2002 |
| *Opuntia ficus indica* va saboten extract | Degradation | Lee et al, 2006 |
| Ozone (aqueous) | Degradation | Huth et al, 2007 |
| Paeony total glucosides | Degradation | Chen et al, 2007 |

TABLE 3-continued

IκBα phosphorylation and/or degradation inhibitors

| Molecule | Point of Inhibition | References |
|---|---|---|
| Pectenotoxin-2 | Degradation | Kim et al, 2008 |
| Penetratin | Degradation | Letoya et al, 2006 |
| Pervanadate (tyrosine phosphatase inhibitor) | Degradation | Singh & Aggarwal, 1995; Singh et al, 1996 |
| Phenylarsine oxide (PAO, tyrosine phosphatase inhibitor) | Degradation | Mahboubi et al, 1998; Singh & Aggarwal, 1995 |
| beta-Phenylethyl (PEITC) and 8-methylsulphinyloctyl isothiocyanates (MSO) (watercress) | Degradation | Rose et al, 2005 |
| Phenytoin | Degradation | Kato et al, 2005 |
| c-phycocyanin | Degradation | Cherng et al, 2007 |
| Platycodin saponins | Degradation | Ahn et al, 2005; Leeet al, 2008 |
| Polymeric formula | Degradation | de Jong et al, 2007 |
| Polymyxin B | Degradation | Jiang et al, 2006 |
| *Poncirus trifoliata* fruit extract | Degradation; phosphorylation of IkBa | Shin et al, 2006; Kim et al, 2007 |
| Probiotics | Degradation | Petrof et al, 2004 |
| Pituitary adenylate cyclase-activating polypeptide (PACAP) | Degradation | Delgado & Ganea, 2001 |
| Prostaglandin 15-deoxy-Delta(12,14)-PGJ(2) | Degradation | Cuzzocrea et al, 2003; Chatterjee et al, 2004 |
| Prodigiosin (*Hahella chejuensis*) | Degradation | Huh et al, 2007 |
| PS-341 | Degradation/proteasome | Hideshima et al, 2002 |
| Radix asari extract | Degradation | Song et al, 2007 |
| Radix clematidis extract | Degradation | Lee et al, 2009 |
| Resiniferatoxin | Degradation | Singh et al, 1996 |
| Sabaeksan | Degradation | Choi et al, 2005 |
| SAIF (*Saccharomyces boulardii* anti-inflammatory factor) | Degradation | Sougioultzis et al, 2006 |
| Sanguis Draconis | Degradation | Choy et al, 2007 |
| San-Huang-Xie-Xin-Tang | Degradation | Shih et al, 2007 |
| Schisandra fructus extract | Degradation | Kang et al, 2006; Quo et al, 2008 |
| Scutellarin | Degradation | Tan et al, 2007 |
| Sesquiterpene lactones (parthenolide; ergolide; guaianolides; alpha-humulene; trans-caryophyllene) | Degradation | Hehner et al, 1998; Whan Han et al, 2001; Schorr et al, 2002; Medeiros et al, 2007 |
| Sevoflurane/isoflurane | Degradation | Boost et al, 2009 |
| Siegeskaurolic acid (from *Siegesbeckia pubescens* root) | Degradation | Park et al, 2007 |
| ST2 (IL-1-like receptor secreted form) | Degradation | Takezako et al, 2006 |
| *Synadenium* carinatum latex lectin | Degradation | Rogerio et al, 2007 |
| *Taiwanofungus camphoratus* | Degradation | Liu et al, 2007 |
| Taurene bromamine | Degradation | Tokunaga et al, 2007 |
| Thiopental | Degradation | Loop et al, 2002 |
| Tipifarnib | Degradation | Xue et al, 2005 |
| Titanium | Degradation | Yang et al, 2003 |
| TNP-470 (angiogenesis inhibitor) | Degradation | Mauriz et al, 2003 |
| Stinging nettle (*Urtica dioica*) plant extracts | Degradation | Riehemann et al, 1999 |
| *Trichomomas vaginalis* infection | Degradation | Chang et al, 2004 |
| Triglyceride-rich lipoproteins | Degradation | Kumwenda et al, 2002 |
| Tussilagone (Farfarae fios) | Degradation | Lim et al, 2008 |
| U0126 (MEK inhibitor) | Degradation | Takaya et al, 2003 |
| Ursodeoxycholic acid | Degradation | Joo et al, 2004 |
| *Xanthium strumarium* L. (methanol extract) | Degradation | Kim et al, 2005; Yoon et al, 2008 |
| Yulda-Hanso-Tang | Degradation | Jeong et al, 2007 |
| Zinc | Degradation | Uzzo et al, 2006; Bao et al, 2006 |
| Molluscum contagiosum virus MC159 protein | IkBbeta degradation | Murao & Shisler, 2005 |
| Vasoactive intestinal peptide | Degradation (and CBP-RelA interaction) | Delgado & Ganea, 2001; Delgado, 2002 |
| HIV-1 Vpu protein | TrCP ubiquitin ligase inhibitor | Bour et al, 2001 |

TABLE 3-continued

IκBα phosphorylation and/or degradation inhibitors

| Molecule | Point of Inhibition | References |
|---|---|---|
| Epoxyquinone A monomer | IKKb/DNA binding | Liang et al, 2006 |
| Ro106-9920 (small molecule) | IkBa ubiqutination inhibitor | Swinney et al, 2002 |
| Furonaphthoquinone | IKK activity | Shin et al, 2006 |

Pharmaceutical Compositions

In alternative embodiments, the invention provides pharmaceutical compositions for practicing the methods of the invention, e.g., pharmaceutical compositions for overcoming or diminishing or preventing Growth Factor Inhibitor (GFI) resistance in a cell, or, a method for increasing the growth-inhibiting effectiveness of a Growth Factor inhibitor on a cell, or, a method for re-sensitizing a cell to a Growth Factor Inhibitor.

In alternative embodiments, compositions used to practice the methods of the invention are formulated with a pharmaceutically acceptable carrier. In alternative embodiments, the pharmaceutical compositions used to practice the methods of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents used to practice the methods of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions used to practice the methods of the invention include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice the methods of the invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, geltabs, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations used to practice the methods of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a composition used to practice the methods of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration hydrophobic active agents used to practice the methods of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing this invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations used to practice the methods of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations used to practice the methods of the invention can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations used to practice the methods of the invention can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions of the invention are administered in an amount sufficient to treat, prevent and/or ameliorate normal, dysfunction (e.g., abnormally proliferating) cell, e.g., cancer cell, or blood vessel cell, including endothelial and/or capillary cell growth; including neovasculature related to (within, providing a blood supply to) hyperplastic tissue, a granuloma or a tumor. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of compositions used to practice the methods of the invention can be in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating cancer, septic shock, infection, fever, pain and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

The invention also provides nanoparticles and liposomal membranes comprising compounds used to practice the methods of the invention. In alternative embodiments, the invention provides nanoparticles and liposomal membranes targeting diseased and/or tumor (cancer) stem cells and dysfunctional stem cells, and angiogenic cells.

In alternative embodiments, the invention provides nanoparticles and liposomal membranes comprising (in addition to comprising compounds used to practice the methods of the invention) molecules, e.g., peptides or antibodies, that selectively target abnormally growing, diseased, infected, dysfunctional and/or cancer (tumor) cell receptors. In alternative embodiments, the invention provides nanoparticles and liposomal membranes using IL-11 receptor and/or the GRP78 receptor to targeted receptors on cells, e.g., on tumor cells, e.g., on prostate or ovarian cancer cells. See, e.g., U.S. patent application publication no. 20060239968.

In one aspect, the compositions used to practice the methods of the invention are specifically targeted for inhibiting, ameliorating and/or preventing endothelial cell migration and for inhibiting angiogenesis, e.g., tumor-associated or disease- or infection-associated neovasculature.

The invention also provides nanocells to allow the sequential delivery of two different therapeutic agents with different modes of action or different pharmacokinetics, at least one of which comprises a composition used to practice the methods of the invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as a retinal age-related macular degeneration, a diabetic retinopathy, a cancer or carcinoma, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, leprosy, multiple sclerosis, inflammatory bowel disease, or ulcerative colitis or Crohn's disease.

In treating cancer, a traditional antineoplastic agent is contained in the outer lipid vesicle of the nanocell, and an antiangiogenic agent of this invention is loaded into the nanocore. This arrangement allows the antineoplastic agent to be released first and delivered to the tumor before the tumor's blood supply is cut off by the composition of this invention.

The invention also provides multilayered liposomes comprising compounds used to practice this invention, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome used to practice the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as *acacia* gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles comprising compounds used to practice this invention to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Liposomes

The compositions and formulations used to practice the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. For example, in one embodiment, compositions and formulations used to practice the invention are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations used to practice the invention are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937. In another embodiment, compositions and formulations used to practice the invention are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations used to practice the invention are delivered by the use of liposomes comprising glycerides, glycerophospholipides, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

Antibodies as Pharmaceutical Compositions

In alternative embodiments, the invention provides compositions and methods for inhibiting or depleting an integrin $\alpha_v\beta_3$ (anb3), or inhibiting an integrin $\alpha_v\beta_3$ (anb3) protein activity, or inhibiting the formation or activity of an integrin anb3/RalB signaling complex, or inhibiting the formation or signaling activity of an integrin $\alpha_v\beta_3$ (anb3)/RalB/NFkB signaling axis; or inhibiting or depleting a RalB protein or an inhibitor of RalB protein activation; or inhibiting or depleting a Src or TBK1 protein or an inhibitor of Src or TBK1 protein activation. In alternative embodiments, this is achieved by administration of inhibitory antibodies. For example, in alternative embodiments, the invention uses isolated, synthetic or recombinant antibodies that specifically bind to and inhibit an integrin $\alpha_v\beta_3$ (anb3), or any protein of an integrin $\alpha_v\beta_3$ (anb3)/RalB/NFkB signaling axis, a RalB protein, a Src or TBK1 protein, or an NFkB protein.

In alternative aspects, an antibody for practicing the invention can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing the invention includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

In alternative embodiments, the invention uses "humanized" antibodies, including forms of non-human (e.g., murine) antibodies that are chimeric antibodies comprising minimal sequence (e.g., the antigen binding fragment) derived from non-human immunoglobulin. In alternative embodiments, humanized antibodies are human immunoglobulins in which residues from a hypervariable region (HVR) of a recipient (e.g., a human antibody sequence) are replaced by residues from a hypervariable region (HVR) of a non-human species (donor antibody) such as mouse, rat, rabbit or nonhuman primate having the desired specificity, affinity, and capacity. In alternative embodiments, framework region (FR) residues of the human immunoglobulin are replaced by corresponding non-human residues to improve antigen binding affinity.

In alternative embodiments, humanized antibodies may comprise residues that are not found in the recipient antibody or the donor antibody. These modifications may be made to improve antibody affinity or functional activity. In alternative embodiments, the humanized antibody can comprise substantially all of at least one, and typically two, variable domains, in which all or substantially all of the hypervariable regions correspond to those of a non-human immunoglobulin and all or substantially all of Ab framework regions are those of a human immunoglobulin sequence.

In alternative embodiments, a humanized antibody used to practice this invention can comprise at least a portion of an immunoglobulin constant region (Fc), typically that of or derived from a human immunoglobulin.

However, in alternative embodiments, completely human antibodies also can be used to practice this invention, including human antibodies comprising amino acid sequence which corresponds to that of an antibody produced by a human. This definition of a human antibody specifically excludes a humanized antibody comprising non-human antigen binding residues.

In alternative embodiments, antibodies used to practice this invention comprise "affinity matured" antibodies, e.g., antibodies comprising with one or more alterations in one or more hypervariable regions which result in an improvement in the affinity of the antibody for antigen; e.g., NFkB, an integrin $\alpha_v\beta_3$ (anb3), or any protein of an integrin $\alpha_v\beta_3$ (anb3)/RalB/NFkB signaling axis, a RalB protein, a Src or TBK1 protein, compared to a parent antibody which does not possess those alteration(s). In alternative embodiments, antibodies used to practice this invention are matured antibodies having nanomolar or even picomolar affinities for the target antigen, e.g., NFkB, an integrin $\alpha_v\beta_3$ (anb3), or any protein of an integrin $\alpha_v\beta_3$ (anb3)/RalB/NFkB signaling axis, a RalB protein, a Src or TBK1 protein. Affinity matured antibodies can be produced by procedures known in the art.

Antisense, siRNAs and microRNAs as Pharmaceutical Compositions

In alternative embodiments, the invention provides compositions and methods for inhibiting or depleting an integrin $\alpha_v\beta_3$ (anb3), or inhibiting an integrin $\alpha_v\beta_3$ (anb3) protein activity, or inhibiting the formation or activity of an integrin anb3/RalB signaling complex, or inhibiting the formation or signaling activity of an integrin $\alpha_v\beta_3$ (anb3)/RalB/NFkB signaling axis; or inhibiting or depleting a RalB protein or an inhibitor of RalB protein activation; or inhibiting or depleting a Src or TBK1 protein or an inhibitor of Src or TBK1 protein activation. In alternative embodiments, this is achieved by administration of inhibitory nucleic acids, e.g., siRNA, antisense nucleic acids, and/or inhibitory microRNAs.

In alternative embodiments, compositions used to practice the invention are formulated with a pharmaceutically acceptable carrier. In alternative embodiments, the pharmaceutical compositions used to practice the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

While the invention is not limited by any particular mechanism of action: microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA.

In alternative embodiments pharmaceutical compositions used to practice the invention are administered in the form of a dosage unit, e.g., a tablet, capsule, bolus, spray. In alternative embodiments, pharmaceutical compositions comprise a compound, e.g., an antisense nucleic acid, e.g., an siRNA or a microRNA, in a dose: e.g., 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, or 800 mg or more.

In alternative embodiments, an siRNA or a microRNA used to practice the invention is administered as a pharmaceutical agent, e.g., a sterile formulation, e.g., a lyophilized siRNA or microRNA that is reconstituted with a suitable diluent, e.g., sterile water for injection or sterile saline for injection. In alternative embodiments the reconstituted product is administered as a subcutaneous injection or as an intravenous infusion after dilution into saline. In alternative embodiments the lyophilized drug product comprises siRNA or microRNA prepared in water for injection, or in saline for injection, adjusted to pH 7.0-9.0 with acid or base during preparation, and then lyophilized. In alternative embodiments a lyophilized siRNA or microRNA of the invention is between about 25 to 800 or more mg, or about 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of a siRNA or microRNA of the invention. The lyophilized siRNA or microRNA of the invention can be packaged in a 2 mL Type I, clear glass vial (e.g., ammonium sulfate-treated), e.g., stoppered with a bromobutyl rubber closure and sealed with an aluminum overseal.

In alternative embodiments, the invention provides compositions and methods comprising in vivo delivery of antisense nucleic acids, e.g., siRNA or microRNAs. In practicing the invention, the antisense nucleic acids, siRNAs, or microRNAs can be modified, e.g., in alternative embodiments, at least one nucleotide of antisense nucleic acid, e.g., siRNA or microRNA, construct is modified, e.g., to improve its resistance to nucleases, serum stability, target specificity, blood system circulation, tissue distribution, tissue penetration, cellular uptake, potency, and/or cell-permeability of the polynucleotide. In alternative embodiments, the antisense nucleic acid, siRNA or microRNA construct is unmodified. In other embodiments, at least one nucleotide in the antisense nucleic acid, siRNA or microRNA construct is modified.

In alternative embodiments, guide strand modifications are made to increase nuclease stability, and/or lower interferon induction, without significantly decreasing antisense nucleic acid, siRNA or microRNA activity (or no decrease in antisense nucleic acid, siRNA or microRNA activity at all). In certain embodiments, the modified antisense nucleic acid, siRNA or microRNA constructs have improved stability in serum and/or cerebral spinal fluid compared to an unmodified structure having the same sequence.

In alternative embodiments, a modification includes a 2'-H or 2'-modified ribose sugar at the second nucleotide from the 5'-end of the guide sequence. In alternative embodiments, the guide strand (e.g., at least one of the two single-stranded polynucleotides) comprises a 2'-O-alkyl or 2'-halo group, such as a 2'-O-methyl modified nucleotide, at the second nucleotide on the 5'-end of the guide strand, or, no other modified nucleotides. In alternative embodiments, polynucleotide constructs having such modification may have enhanced target specificity or reduced off-target silencing compared to a similar construct without the 2'-O-methyl modification at the position.

In alternative embodiments, a second nucleotide is a second nucleotide from the 5'-end of the single-stranded polynucleotide. In alternative embodiments, a "2'-modified ribose sugar" comprises ribose sugars that do not have a 2'-OH group. In alternative embodiments, a "2'-modified ribose sugar" does not include 2'-deoxyribose (found in unmodified canonical DNA nucleotides), although one or more DNA nucleotides may be included in the subject constructs (e.g., a single deoxyribonucleotide, or more than one deoxyribonucleotide in a stretch or scattered in several parts of the subject constructs). For example, the 2'-modified ribose sugar may be 2'-O-alkyl nucleotides, 2'-deoxy-2'-fluoro nucleotides, 2'-deoxy nucleotides, or combination thereof.

In alternative embodiments, an antisense nucleic acid, siRNA or microRNA construct used to practice the invention comprises one or more 5'-end modifications, e.g., as described above, and can exhibit a significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the antisense nucleic acid, siRNA or microRNA construct of the invention.

In alternative embodiments, an antisense nucleic acid, siRNA or microRNA construct to practice the invention comprises a guide strand modification that further increase stability to nucleases, and/or lowers interferon induction, without significantly decreasing activity (or no decrease in microRNA activity at all). In alternative embodiments, the 5'-stem sequence comprises a 2'-modified ribose sugar, such as 2'-O-methyl modified nucleotide, at the second nucleotide on the 5'-end of the polynucleotide, or, no other modified nucleotides. In alternative embodiments the hairpin structure having such modification has enhanced target specificity or reduced off-target silencing compared to a similar construct without the 2'-O-methyl modification at same position.

In alternative embodiments, the 2'-modified nucleotides are some or all of the pyrimidine nucleotides (e.g., C/U). Examples of 2'-O-alkyl nucleotides include a 2'-O-methyl nucleotide, or a 2'-O-allyl nucleotide. In alternative embodiments, the modification comprises a 2'-O-methyl modification at alternative nucleotides, starting from either the first or the second nucleotide from the 5'-end. In alternative embodiments, the modification comprises a 2'-O-methyl modification of one or more randomly selected pyrimidine nucleotides (C or U). In alternative embodiments, the modification comprises a 2'-O-methyl modification of one or more nucleotides within the loop.

In alternative embodiments, the modified nucleotides are modified on the sugar moiety, the base, and/or the phosphodiester linkage. In alternative embodiments the modification comprise a phosphate analog, or a phosphorothioate linkage; and the phosphorothioate linkage can be limited to one or more nucleotides within the loop, a 5'-overhang, and/or a 3'-overhang.

In alternative embodiments, the phosphorothioate linkage may be limited to one or more nucleotides within the loop, and 1, 2, 3, 4, 5, or 6 more nucleotide(s) of the guide sequence within the double-stranded stem region just 5' to the loop. In alternative embodiments, the total number of nucleotides having the phosphorothioate linkage may be about 12-14. In alternative embodiments, all nucleotides having the phosphorothioate linkage are not contiguous. In alternative embodiments, the modification comprises a 2'-O-methyl modification, or, no more than 4 consecutive nucleotides are modified. In alternative embodiments, all nucleotides in the 3'-end stem region are modified. In alternative embodiments, all nucleotides 3' to the loop are modified.

In alternative embodiments, the 5'- or 3'-stem sequence comprises one or more universal base-pairing nucleotides. In alternative embodiments universal base-pairing nucleotides include extendable nucleotides that can be incorporated into a polynucleotide strand (either by chemical synthesis or by a polymerase), and pair with more than one pairing type of specific canonical nucleotide. In alternative embodiments, the universal nucleotides pair with any specific nucleotide. In alternative embodiments, the universal nucleotides pair with four pairings types of specific nucleotides or analogs thereof. In alternative embodiments, the universal nucleotides pair with three pairings types of specific nucleotides or analogs thereof. In alternative embodiments, the universal nucleotides pair with two pairings types of specific nucleotides or analogs thereof In alternative embodiments, an antisense nucleic acid, siRNA or microRNA used to practice the invention comprises a modified nucleoside, e.g., a sugar-modified nucleoside. In alternative embodiments, the sugar-modified nucleosides can further comprise a natural or modified heterocyclic base moiety and/or a natural or modified internucleoside linkage; or can comprise modifications independent from the sugar modification. In alternative embodiments, a sugar modified nucleoside is a 2'-modified nucleoside, wherein the sugar ring is modified at the 2' carbon from natural ribose or 2'-deoxy-ribose.

In alternative embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In alternative embodiments, the bicyclic sugar moiety is an L sugar in the beta configuration.

In alternative embodiments, the bicyclic sugar moiety comprises a bridge group between the 2' and the 4'-carbon atoms. In alternative embodiments, the bridge group comprises from 1 to 8 linked biradical groups. In alternative embodiments, the bicyclic sugar moiety comprises from 1 to 4 linked biradical groups. In alternative embodiments, the bicyclic sugar moiety comprises 2 or 3 linked biradical groups.

In alternative embodiments, the bicyclic sugar moiety comprises 2 linked biradical groups. In alternative embodiments, a linked biradical group is selected from —O—, —S—, —N(R1)-, —C(R1)(R$_2$)—, —C(R1)=C(R1)-, —C(R1)=N—, —C(=NR1)-, —Si(R1)(R$_2$)—, —S(=O)$_2$—, —S(=O)—, —C(=O)— and —C(=S)—; where each R1 and R$_2$ is, independently, H, hydroxyl, C1 to C$_{12}$ alkyl, substituted C1-C12 alkyl, C$_2$-C12 alkenyl, substituted C$_2$-C$_{12}$ alkenyl, C$_2$-C$_{12}$ alkynyl, substituted C$_2$-C12 alkynyl, C$_2$-C20 aryl, substituted C$_2$-C20 aryl, a heterocycle radical, a substituted heterocycle radical, heteroaryl, substituted heteroaryl, C$_2$-C$_7$ alicyclic radical, substituted C$_2$-C$_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, C1-C$_{12}$ alkyl, substituted C1-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, amino, substituted amino, acyl, substituted acyl, C1-C$_{12}$ aminoalkyl, C1-C$_{12}$ aminoalkoxy, substituted C1-C$_{12}$ aminoalkyl, substituted C1-C$_{12}$ aminoalkoxy or a protecting group.

In alternative embodiments, the bicyclic sugar moiety is bridged between the 2' and 4' carbon atoms with a biradical group selected from —O—(CH$_2$)x-, —O—CH$_2$—, —O—CH$_2$CH$_2$—, —O—CH(alkyl)-, —NH—(CH2)P—, —N(alkyl)-(CH$_2$)x-, —O—CH(alkyl)-, —(CH(alkyl))-(CH2)x-, —NH—O—(CH2)x-, —N(alkyl)-O—(CH$_2$)x-, or —O—N(alkyl)-(CH$_2$)x-, wherein x is 1, 2, 3, 4 or 5 and each alkyl group can be further substituted. In certain embodiments, x is 1, 2 or 3.

In alternative embodiments, a 2'-modified nucleoside comprises a 2'-substituent group selected from halo, allyl, amino, azido, SH, CN, OCN, CF$_3$, OCF$_3$, O—, S—, or N(Rm)-alkyl; O—, S—, or N(Rm)-alkenyl; O—, S— or N(Rm)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(Rm)(Rn) or O—CH2-C(=O)—N(Rm)(Rn), where each Rm and Rn is, independently, H, an amino protecting group or substituted or unsubstituted C1-C10 alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl. In alternative embodiments, a 2'-modified nucleoside comprises a 2'-substituent group selected from F, O—CH$_3$, and OCH$_2$CH$_2$OCH$_3$.

In alternative embodiments, a sugar-modified nucleoside is a 4'-thio modified nucleoside. In alternative embodiments, a sugar-modified nucleoside is a 4'-thio-2'-modified nucleoside. In alternative embodiments a 4'-thio modified nucleoside has a .beta.-D-ribonucleoside where the 4'-O replaced with 4'-S. A 4'-thio-2'-modified nucleoside is a 4'-thio modified nucleoside having the 2'-OH replaced with a 2'-substituent group. In alternative embodiments 2'-substituent groups include 2'-OCH$_3$, 2'-O—(CH2)$_2$—OCH$_3$, and 2'-F.

In alternative embodiments, a modified oligonucleotide of the present invention comprises one or more internucleoside modifications. In alternative embodiments, each internucleoside linkage of a modified oligonucleotide is a modified internucleoside linkage. In alternative embodiments, a modified internucleoside linkage comprises a phosphorus atom.

In alternative embodiments, a modified antisense nucleic acid, siRNA or microRNA comprises at least one phosphorothioate internucleoside linkage. In certain embodiments, each internucleoside linkage of a modified oligonucleotide is a phosphorothioate internucleoside linkage.

In alternative embodiments, a modified internucleoside linkage does not comprise a phosphorus atom. In alternative embodiments, an internucleoside linkage is formed by a short chain alkyl internucleoside linkage. In alternative embodiments, an internucleoside linkage is formed by a cycloalkyl internucleoside linkages. In alternative embodiments, an internucleoside linkage is formed by a mixed heteroatom and alkyl internucleoside linkage. In alternative embodiments, an internucleoside linkage is formed by a mixed heteroatom and cycloalkyl internucleoside linkages. In alternative embodiments, an internucleoside linkage is formed by one or more short chain heteroatomic internucleoside linkages. In alternative embodiments, an internucleoside linkage is formed by one or more heterocyclic internucleoside linkages. In alternative embodiments, an internucleoside linkage has an amide backbone, or an internucleoside linkage has mixed N, O, S and CH2 component parts.

In alternative embodiments, a modified oligonucleotide comprises one or more modified nucleobases. In certain embodiments, a modified oligonucleotide comprises one or more 5-methylcytosines, or each cytosine of a modified oligonucleotide comprises a 5-methylcytosine.

In alternative embodiments, a modified nucleobase comprises a 5-hydroxymethyl cytosine, 7-deazaguanine or 7-deazaadenine, or a modified nucleobase comprises a 7-deaza-adenine, 7-deazaguanosine, 2-aminopyridine or a 2-pyridone, or a modified nucleobase comprises a 5-substituted pyrimidines, 6-azapyrimidines and N-2, N-6 and O-6 substituted purines, or a 2 aminopropyladenine, 5-propynyluracil or a 5-propynylcytosine.

In alternative embodiments, a modified nucleobase comprises a polycyclic heterocycle, or a tricyclic heterocycle; or, a modified nucleobase comprises a phenoxazine derivative, or a phenoxazine further modified to form a nucleobase or G-clamp.

Therapeutically Effective Amount and Doses

In alternative embodiment, compounds, compositions, pharmaceutical compositions and formulations used to practice the invention can be administered for prophylactic and/or therapeutic treatments; for example, the invention provides compositions and methods for overcoming or diminishing or preventing Growth Factor Inhibitor (GFI) resistance in a cell, or, a method for increasing the growth-inhibiting effectiveness of a Growth Factor inhibitor on a cell, or, a method for re-sensitizing a cell to a Growth Factor Inhibitor. In alternative embodiments, the invention provides compositions and methods for treating, preventing or ameliorating: a disease or condition associated with dysfunctional stem cells or cancer stem cells, a retinal age-related macular degeneration, a diabetic retinopathy, a cancer or carcinoma, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, leprosy, multiple sclerosis, inflammatory bowel disease, or ulcerative colitis or Crohn's disease. In therapeutic applications, compositions are administered to a subject already suffering from a condition, infection or disease in an amount sufficient to cure, alleviate or partially arrest the clinical manifestations of the condition, infection or disease (e.g., disease or condition associated with dysfunctional stem cells or cancer stem cells) and its complications (a "therapeutically effective amount"). In the methods of the invention, a pharmaceutical composition is administered in an amount sufficient to treat (e.g., ameliorate) or prevent a disease or condition associated with dysfunctional stem cells or cancer stem cells. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

Kits and Instructions

The invention provides kits comprising compositions for practicing the methods of the invention, including instructions for use thereof. In alternative embodiments, the invention provides kits, blister packages, lidded blisters or blister cards or packets, clamshells, trays or shrink wraps comprising a combination of compounds. In alternative embodiments, the combination of compounds comprises:

(1) at least one compound comprising or consisting of:
(i) an inhibitor or depleter of integrin $\alpha_v\beta_3$ (anb3), or an inhibitor of integrin $\alpha_v\beta_3$ (anb3) protein activity, or an inhibitor of the formation or activity of an integrin anb3/RalB signaling complex, or an inhibitor of the formation or signaling activity of an integrin $\alpha_v\beta_3$ (anb3)/RalB/NFkB signaling axis,
wherein optionally the inhibitor of integrin $\alpha_v\beta_3$ protein activity is an allosteric inhibitor of integrin $\alpha_v\beta_3$ protein activity;
(ii) an inhibitor or depleter of RalB protein or an inhibitor of RalB protein activation,
wherein optionally the inhibitor of RalB protein activity is an allosteric inhibitor of RalB protein activity;
(iii) an inhibitor or depleter of Src or a Tank Binding Kinase (TBK1) protein or an inhibitor of Src or TBK1 protein activation,
wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™,
and optionally the inhibitor of the Src or the TBK1 protein activity is an allosteric inhibitor of Src or TBK1 protein activity;
(iv) an inhibitor or depleter of NFKB or IRF3 protein or an inhibitor of RalB protein activation,
wherein optionally the inhibitor of NFKB or IRF3 protein activity is an allosteric inhibitor of NFKB or IRF3 protein activity; or
(v) any combination of (i) to (iv); and
(2) at least one Growth Factor Inhibitor.

In alternative embodiments, the kit further comprises instructions for practicing a method of the invention.

The invention will be further described with reference to the following examples; however, it is to be understood that the invention is not limited to such examples.

EXAMPLES

Example 1

Methods of the Invention are Effective for Sensitizing and Re-Sensitizing Cancer Cells to Growth Factor Inhibitors The data presented herein demonstrates the effectiveness of the compositions and methods of the invention in sensitizing and re-sensitizing cancer cells, and cancer stem cells, to growth factor inhibitors, and validates this invention's therapeutic approach to overcome growth factor inhibitor, e.g., EGFR inhibitor, resistance for a wide range of cancers. The data presented herein demonstrates that genetic and pharmacological inhibition of RalB or NF-κB was able to re-sensitize αvβ3-expressing tumors to EGFR inhibitors.

Resistance to epidermal growth factor receptor (EGFR) inhibitors has emerged as a significant clinical problem in oncology owing to various resistance mechanisms[1,2]. Since cancer stem cells have been associated with drug resistance[3], we examined the expression of stem/progenitor cell markers for breast, pancreas and colon tumor cells with acquired resistance to EGFR inhibitors. We found that CD61 (β3 integrin) was the one marker consistently upregulated on EGFR inhibitor resistant tumor cells. Moreover, integrin αvβ3 expression was markedly enhanced in murine orthotopic lung and pancreas tumors following their acquired resistance to systemically delivered EGFR inhibitors. In fact, αvβ3 was both necessary and sufficient to account for the tumor cell resistance to EGFR inhibitors and other growth factor receptor inhibitors but not cytotoxic drugs.

Mechanistically, in drug resistant tumors αvβ3 forms a complex with KRAS via the adaptor Galectin-3 resulting in recruitment of RalB and activation of its effector TBK1/NF-κB, revealing a previously undescribed integrin-mediated pathway. Accordingly, genetic or pharmacological inhibition of Galectin-3, RalB or NF-κB was able to re-sensitize αvβ3-expressing tumors to EGFR inhibitors, demonstrating the effectiveness of the compositions and methods of the invention and validating this invention's therapeutic approach to overcome EGFR inhibitor resistance for a wide range of cancers.

Despite some level of clinical success achieved with EGFR Tyrosine Kinase inhibitors (TKIs), intrinsic and acquired cellular resistance mechanisms limit their efficacy[1,2,4]. A number of resistance mechanisms have been identified, including KRAS and EGFR mutations, resulting in constitutive activation of the ERK pathway[5-7]. While KRAS-mediated ERK signaling is associated with resistance to EGFR inhibition, KRAS also induces PI3K and Ral activation leading to tumor cell survival and proliferation[8,9].

Nevertheless, it is clear that treatment of tumors with EGFR inhibitors appears to select for a cell population that remains insensitive to EGFR blockade[1,2]. Prolonged administration of tumors with EGFR TKIs also selects for cells characterized by a distinct array of membrane proteins, including cancer stem/progenitor cell markers known to be associated with increased cell survival and metastasis[10]. While a number of EGFR-inhibitor resistance mechanisms have been defined, it is not clear whether a single unifying mechanism might drive the resistance of a broad range of cancers.

To investigate this, we exposed pancreatic (FG, Miapaca-2), breast (BT474, SKBR3 and MDAMB468) and colon (SW480) human tumor cell lines to increasing concentrations of erlotinib or lapatinib for three weeks, to select cell subpopulations that were at least 10-fold more resistant to these targeted therapies than their parental counterparts. Parent or resistant cells were then evaluated for a panel of stem/progenitor cell markers previously identified to be upregulated in the most aggressive metastatic tumor cells[11-13].

Figure 5:
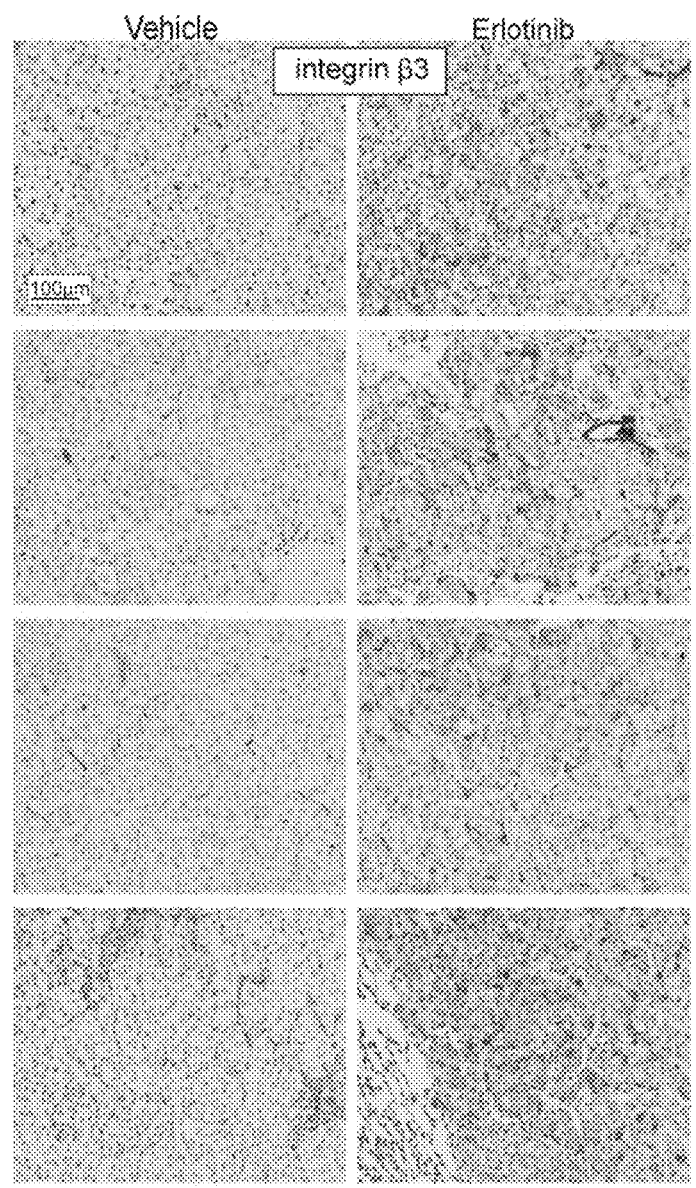
FIG. 5 (or Supplementary FIG. 1, Example 1) illustrates that prolonged exposure to erlotinib induces Integrin αvβ3 expression in lung tumors; representative immunohistochemical staining of integrin β3 in mouse tissues obtained from H441 orthotopic lung tumors long-term treated with either vehicle or erlotinib (scale bar, 100 μm); as discussed in detail in Example 1, below.

As expected, the expression of some of these markers was significantly increased in one or more of these resistant cell populations. Surprisingly, we observed that CD61 (integrin β3) was the one marker upregulated in all resistant cell lines tested, FIG. 1a. The longer cells were exposed to erlotinib the greater the expression level of αvβ3 was observed, FIG. 1b. These findings were extended in vivo as mice bearing orthotopic FG pancreatic tumors with minimal integrin αvβ3 evaluated following four weeks of erlotinib treatment showed a 10-fold increase in αvβ3 expression, FIG. 1c. Moreover, H441 human lung adenocarcinoma orthotopic tumors[14] exposed to systemic erlotinib treatment in vivo for 7-8 weeks developed resistance and a qualitative increase in integrin αvβ3 expression compared with vehicle-treated tumors, see FIG. 1d and FIG. 5 (Supplementary FIG. 1). Thus, exposure of histologically distinct tumor cells in vitro or in vivo to EGFR inhibitors selects for a tumor cell population expressing high levels of αvβ3.

In addition to being expressed on a subpopulation of stem/progenitor cells during mammary development[15], αvβ3 is a marker of the most malignant tumor cells in a wide range of cancers[16,17]. To determine whether endogenous expression of integrin αvβ3 might predict tumor cell resistance to EGFR blockade, various breast, lung and pancreatic tumor cells were first screened for αvβ3 expression and then analyzed for their sensitivity to EGFR inhibitors (Supplementary Table 1).

TABLE 1

Seguin et al, Supplementary Table 1
KRAS mutation, integrin αvβ3 expression and
EGFR TKI sensitivity of cancer cell lines

| Cell line | Origin | Mutated KRAS | integrin αvβ3 expression | EGFR TKI sensitive |
|---|---|---|---|---|
| PANC-1 | pancreas | yes | yes | no |
| FG | pancreas | yes | no | yes |
| Mapaca-2 (MP2) | pancreas | yes | no | yes |
| CAPAN-1 | pancreas | yes | no | yes |
| XPA-1 | pancreas | no | no | yes |
| CFPAC-1 | pancreas | yes | yes | no |
| A549 | lung | yes | yes | no |
| SKBR3 | breast | no | no | yes |
| MDAMB231 | breast | yes | yes | no |
| MDAMB468 (MDA468) | breast | no | no | yes |
| BT474 | breast | no | no | yes |
| BT20 | breast | no | yes | no |
| T47D | breast | yes | no | yes |
| SW480 | colon | yes | no | yes |

Figure 1B:
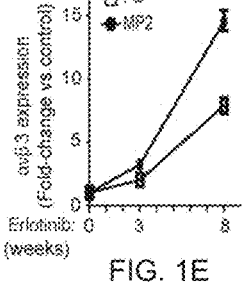
FIG. 1(b) illustrates flow cytometric analysis of αvβ3 expression in FG and Miapaca-2 cells following erlotinib.
Figure 1C:
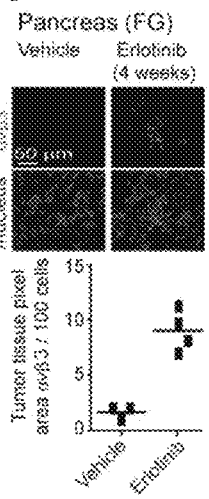
FIG. 1 illustrates that integrin αvβ3 expression promotes resistance to EGFR TKI.
FIG. 1(d) Right, intensity of β3 expression in mouse orthotopic lung tumors treated with vehicle or erlotinib, Left, immunohistochemical staining of β3.
FIG. 1(e) illustrates data showing that β3 expressing tumor cells were intrinsically more resistant to EGFR blockade than β3-negative tumor cell lines, where the cells were first screened for αvβ3 expression and then analyzed for their sensitivity to EGFR inhibitors erlotinib or lapatinib.
FIG. 1(f) illustrates tumor sphere formation assay to establish a dose-response for erlotinib.
FIG. 1(g) illustrates orthotopic FG tumors treated for 10 days with vehicle or erlotinib, results are expressed as % tumor weight compared to vehicle control, immunoblot analysis for tumor lysates after 10 days of erlotinib confirms suppressed EGFR phosphorylation; as discussed in detail in Example 1, below.
Figure 1D:
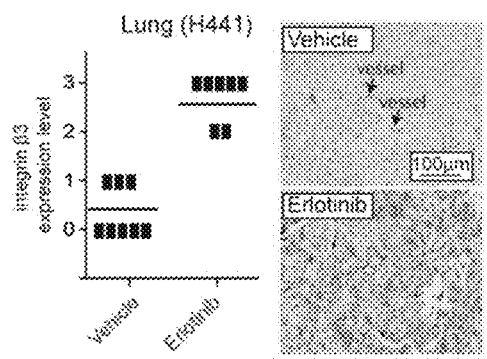
Figure 1E:
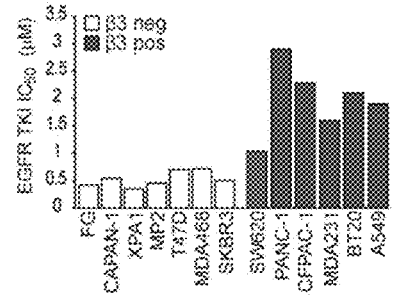
Figure 1F:
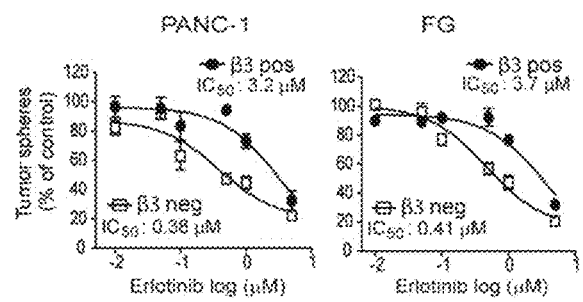
Figure 1G:
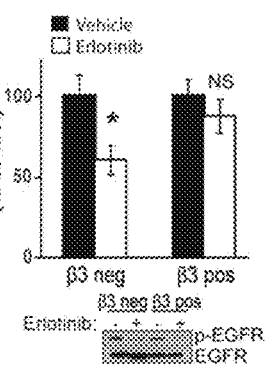

In all cases, β3 expressing tumor cells were intrinsically more resistant to EGFR blockade than β3-negative tumor cell lines (FIG. 1e). In fact, αvβ3 was required for resistance to EGFR inhibitors, since knockdown of αvβ3 in PANC-1 cells resulted in a 10-fold increase in tumor cell sensitivity to erlotinib (FIG. 1f). Moreover, integrin αvβ3 was sufficient to induce erlotinib resistance since ectopic expression of αvβ3 in FG cells lacking this integrin dramatically increased erlotinib resistance both, in vitro and in orthotopic pancreatic tumors after systemic treatment in vivo (FIGS. 1f and g).

Figure 6A:
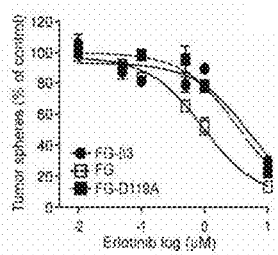
FIG. 6(a) illustrates a tumor sphere formation assay comparing FG lacking β3 (FG), FG expressing β3 wild type (FG-β3) or the β3 D119A (FG-D119A) ligand binding domain mutant, treated with a dose response of erlotinib (Error bars represent s.d. (n=3 independent experiments)

Integrin αvβ3 not only promotes adhesion-dependent signaling via activation of focal adhesion kinase FAK[16] but it can also activate a FAK-independent signaling cascade in the absence of integrin ligation that is associated with increased survival and tumor metastasis[17]. To determine whether αvβ3 ligation was required for its causative role in erlotinib resistance, FG cells transfected with either WT β3 or a ligation deficient mutant of the integrin (D119A)[17] were treated with erlotinib. The same degree of erlotinib resistance was observed in cells expressing either the ligation competent or incompetent form of integrin αvβ3, see FIG. 6a (Supplementary FIG. 2a) indicating that expression of αvβ3, even in the unligated state, was sufficient to induce tumor cell resistance to erlotinib.

Figure 6B:
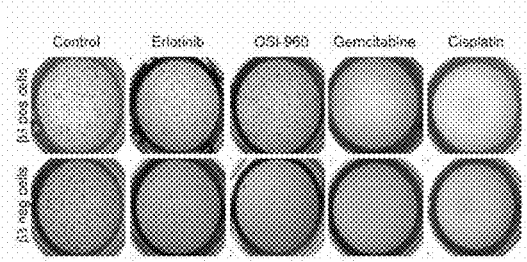
FIG. 6(b) illustrates tumor sphere formation assay of FG and FG-β3 cells untreated or treated with erlotinib (0.5 μM), OSI-906 (0.1 μM), gemcitabine (0.01 μM) or cisplatin (0.1 μM)
Figure 6C:
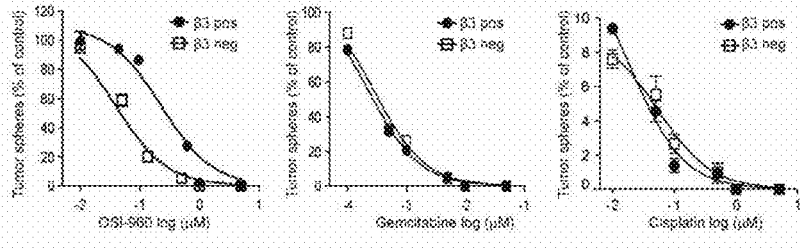
FIG. 6(c) illustrates the effect of dose response of indicated treatments on tumor sphere formation (Error bars represent s.d. (n=3 independent experiments); as discussed in detail in Example 1, below.

Tumor cells with acquired resistance to one drug can often display resistance to a wide range of drugs[18,19]. Therefore, we examined whether αvβ3 expression also promotes resistance to other growth factor inhibitors and/or cytotoxic agents. Interestingly, while αvβ3 expression accounted for EGFR inhibitor resistance, it also induced resistance to the IGFR inhibitor OSI-906, yet failed to protect cells from the antimetabolite agent gemcitabine and the chemotherapeutic agent cisplatin, see FIG. 6b and FIG. 6c (Supplementary FIGS. 2b and c). These results demonstrate that integrin αvβ3 accounts for tumor cell resistance to drugs that target growth factor receptor mediated pathways but does not promote for a more general resistant phenotype to all drugs, particularly those that induce cell cytotoxicity.

Figure 4A:
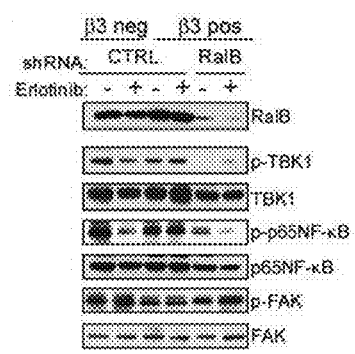
FIG. 4(a) illustrates an immunoblot analysis of FG, FG-β3 and FG-β stably expressing non-silencing or RalB-specific ShRNA, grown in suspension and treated with erlotinib (0.5 μM)
Figures 7A, 7B:
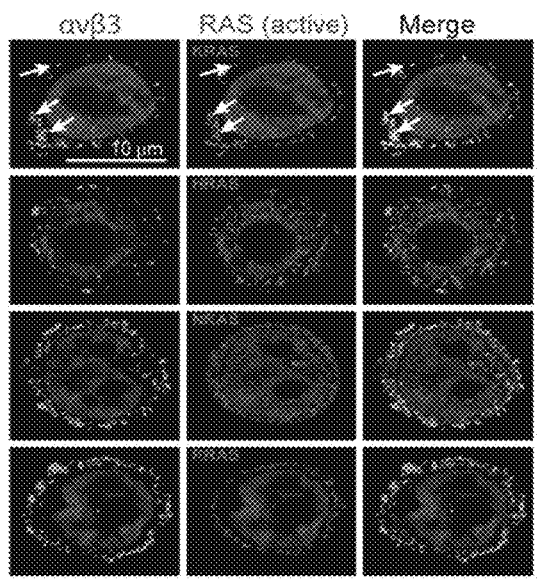
FIG. 7(a) illustrates that Ras activity was determined in PANC-1 cells grown in suspension by using a GST-Rafl-RBD immunoprecipitation assay as described in Methods, see Example 1 (data are representative of two independent experiments)
FIG. 7(b) illustrates confocal microscopy images of PANC-1 cells grown in suspension and stained for KRAS, RRAS, HRAS, NRAS (red), integrin αvβ3 (green) and DNA (TOPRO-3, blue) (Scale bar, 10 μm. Data are representative of two independent experiments); as discussed in detail in Example 1, below.

In some cases oncogenic KRAS has been associated with EGFR TKIs resistance[20], however, it remains unclear whether oncogenic KRAS is a prerequisite for EGFR resistance[21]. Thus, we examined the KRAS mutational status in various tumor cell lines and found that KRAS oncogenic status did not account for resistance to EGFR inhibitors (Supplementary Table 1). Nevertheless, knockdown of KRAS in αvβ3 expressing cells rendered them sensitive to erlotinib while KRAS knockdown in cells lacking αvβ3 had no such effect, see FIG. 6a and FIG. 6b, indicating that αvβ3 and KRAS function cooperatively to promote tumor cell resistance to erlotinib. Interestingly, even in non-adherent cells, αvβ3 colocalized with oncogenic KRAS in the plasma membrane (FIG. 2c) and could be co-precipitated in a complex with KRAS, see FIG. 6d. This interaction was specific for KRAS, as αvβ3 was not found to associate with N-, R- or H-RAS isoforms in these cells, see FIG. 6d and FIG. 7a and FIG. 7b (Supplementary FIGS. 3a and b). Furthermore, in BXPC3 human pancreatic tumor cells expressing wildtype KRAS, αvβ3 showed increased association with KRAS only after these cells were stimulated with EGF, see FIG. 6e. Previous studies have indicated that the KRAS interacting protein Galectin-3 can also couple to integrins[22,23]. Therefore, we considered whether Galectin-3 might serve as an adaptor facilitating an interaction between αvβ3 and KRAS in epithelial tumor cells. In PANC-1 cells with endogenous β3 expression, αvβ3, KRAS, and Galectin-3 co-localized to membrane clusters, see FIG. 8a and FIG. 8b (Supplementary FIG. 4a-b). Furthermore, knockdown of either β3 or Galectin-3 prevented the localization of KRAS to these membrane clusters or their co-immunoprecipitation, see FIG. 8 (Supplementary FIG. 4).

Figure 9A:
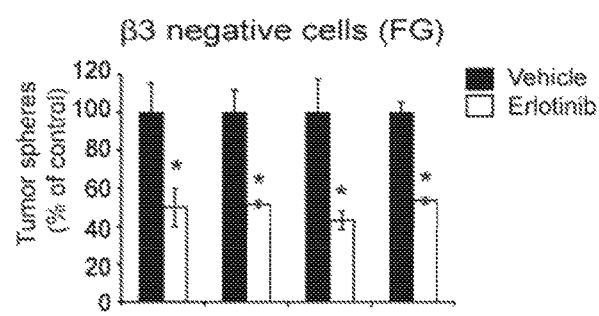
FIG. 9A β3-negative cells, and FIG. 9B, β3-positive cells; tumor spheres formation assay of FG and FG-β3 expressing non-silencing or ERK1/2, AKT1 and RalA-specific shRNA and treated with erlotinib (0.5 μM), error bars represent s.d. (n=3 independent experiments); as discussed in detail in Example 1, below.
Figure 9B:
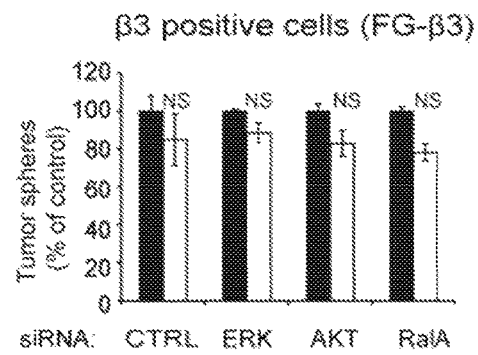
FIG. 9 (or Supplementary FIG. 5, Example 1) illustrates that ERK, AKT and RalA are not specifically required to promote integrin αvβ3-mediated resistance to EGFR™.
Figure 10A:
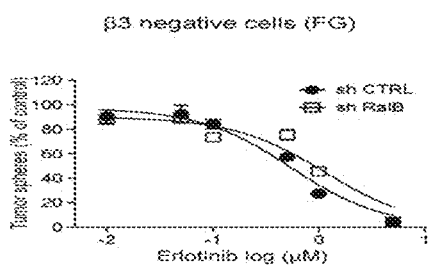
FIG. 10(a) (supplementary FIG. 6, Example 1) illustrates a tumor sphere formation assay of FG expressing non-silencing or RalB specific shRNA and treated with a dose response of erlotinib. Error bars represent s.d. (n=3 independent experiments)
Figure 10B:
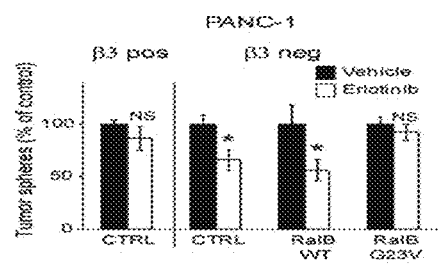
FIG. 10(b) (supplementary FIG. 6) illustrates a tumor spheres formation assay of PANC-1 stably expressing integrin β3-specific shRNA and ectopically expressing vector control, WT RalB FLAG tagged or a constitutively active RalB G23V FLAG tagged constructs treated with erlotinib (0.5 μM), error bars represent s.d. (n=3 independent experiments)
Figure 10C:
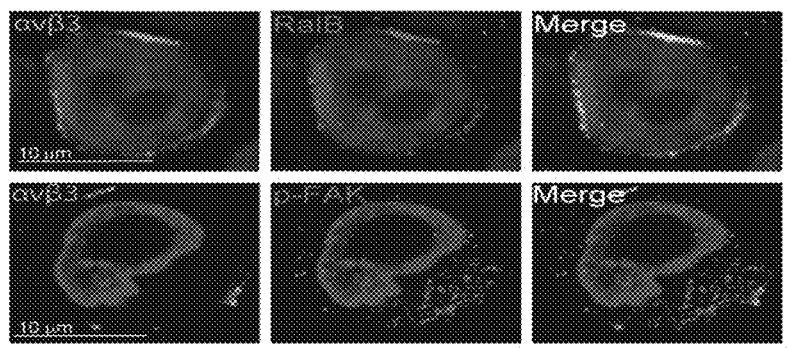
FIG. 10(c) (Supplementary FIG. 7, Example 1) shows that integrin αvβ3 colocalizes with RalB in cancer cells: illustrates confocal microscopy images of Panc-1 cells grown in suspension. Cells are stained for integrin αvβ3 (green), RalB (red), pFAK (red), and DNA (TOPRO-3, blue), scale bar, 10 μm, data are representative of three independent experiments; as discussed in detail in Example 1, below.
Figure 11A:
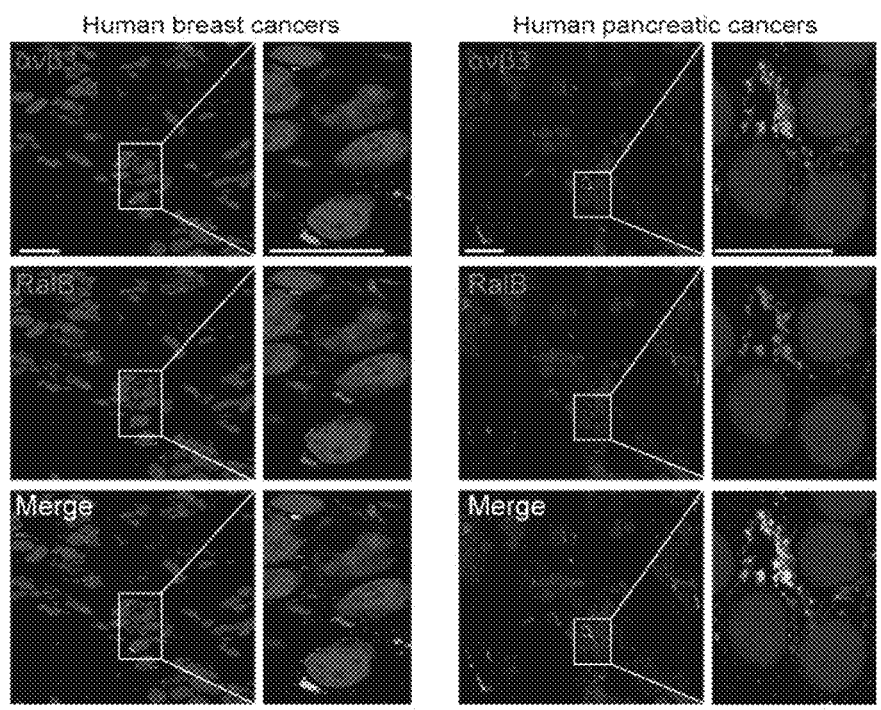
FIG. 11(a) illustrates confocal microscopy images of integrin αvβ3 (green), RalB (red) and DNA (TOPRO-3, blue) in tumor biopsies from breast and pancreatic cancer patients, Scale bar, 20 μm.
Figure 11B:
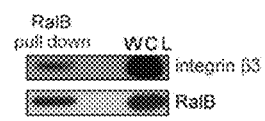
FIG. 11(b) illustrates a Ral activity assay performed in PANC-1 cells using GST-RalBP1-RBD immunoprecipitation assay, Immunoblot analysis of RalB and integrin β, data are representative of three independent experiments; as discussed in detail in Example 1, below.
Figure 13A:
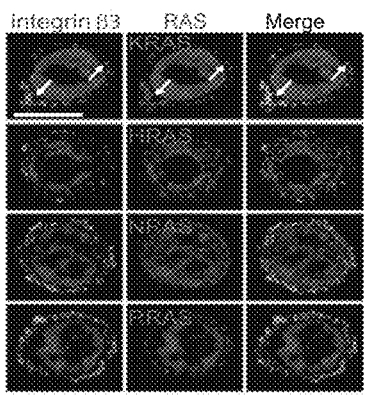
FIG. 13(A) illustrates confocal microscopy images showing immunostaining for integrin β3 (green), K-, N-, H-, R-Ras (red), and DNA (TOPRO-3, blue) for BxPc3 cells grown in suspension in media with 10% serum, arrows indicate clusters where integrin β3 and KRAS colocalize (yellow)
Figure 13B:
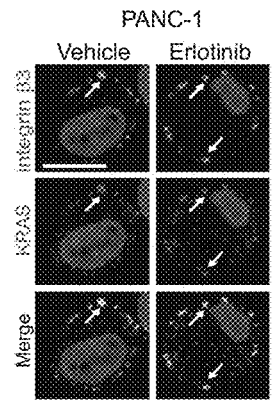
FIG. 13 (or FIG. 2 in Example 2) illustrates data showing that integrin β3 is required to promote KRAS dependency and KRAS-mediated EGFR inhibitor resistance.
FIG. 13(D) graphically illustrates the effect of KRAS knockdown on tumorspheres formation in a panel of lung and pancreatic cancer cells expressing or lacking integrin β3.
FIG. 13(E) graphically illustrates the effect of KRAS knockdown on tumorsphere formation in PANC-1 (KRAS mutant) stably expressing non-target shRNA control (0-positive) or specific-integrin β3 shRNA (β3 negative) in FG (KRAS mutant) and BxPc3 (KRAS wild-type) stably expressing vector control or integrin β3.
FIG. 13(F) graphically illustrates the effect of KRAS knockdown on erlotinib resistance of β3-negative and β3-positive epithelial cancer cell lines, cells were treated with a dose response of erlotinib.
FIG. 13(G) illustrates confocal microscopy images showing immunostaining for integrin β3 (green), KRAS (red) and DNA (TOPRO-3, blue) for PANC-1 cells expressing non-target shRNA control or Galectin 3-specific shRNA grown in suspension.
FIG. 13(H) illustrates: Top: immunoblot analysis of integrin β3 immunoprecipitates from PANC-1 cells expressing non-target shRNA control (CTRL) or Galectin-3-specific shRNA (Gal-3); Bottom: immunoblot analysis of Galectin-3 immunoprecipitates from PANC-1 cells expressing non-target shRNA control (CTRL) or integrin β3-specific shRNA (β3)
FIG. 13(I) graphically illustrates erlotinib dose response of FG-β3 cells expressing a non-target shRNA control or a Galectin-3-specific shRNA (sh Gal-3); as further described in Example 2, below.
Figure 13C:
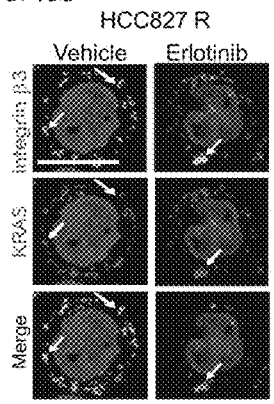
Figure 13D:
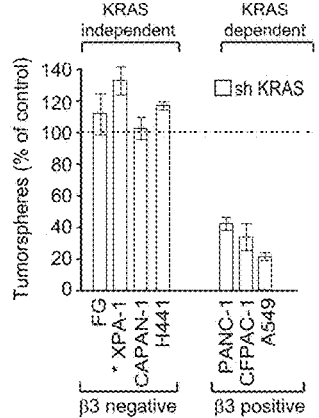
Figure 13E:
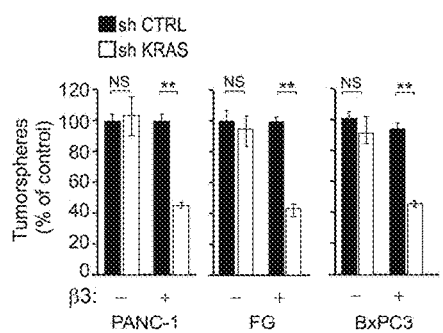
Figure 13F:
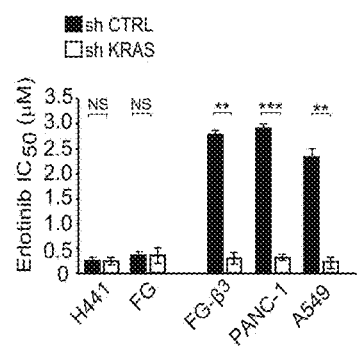

KRAS promotes multiple effector pathways including those regulated by RAF, phosphatidylinositol-3-OH kinases (PI3Ks) and RalGEFs leading to a variety of cellular functions[24]. To investigate whether one or more KRAS effector pathway(s) may contribute to integrin β3/KRAS-mediated tumor cell resistance to EGFR inhibitors, we individually knocked-down or inhibited each downstream RAS effector in cells expressing or lacking integrin αvβ3. While suppression of AKT, ERK and RalA sensitized tumor cells to erlotinib, regardless of the αvβ3 expression status, see FIG. 9 (Supplementary FIG. 5), knockdown of RalB selectively sensitized αvβ3 expressing tumor cells to erlotinib, see FIG. 7a and FIG. 10a (Supplementary FIG. 6a). This was relevant to pancreatic tumor growth in vivo since, knockdown of RalB re-sensitized αvβ3-expressing pancreatic orthotopic tumors to erlotinib in mice, see FIG. 7b. In fact, expression of a constitutively active RalB (G23V) mutant in β3-negative cells was sufficient to confer resistance to EGFR inhibition, see FIG. 7c and FIG. 10b (Supplementary FIG. 6b). Furthermore, ectopic expression of αvβ3 enhanced RalB activity in tumor cells in a KRAS-dependent manner, see FIG. 7d). Accordingly, integrin αvβ3 and RalB were co-localized in tumor cells, see FIG. 10c (Supplementary FIG. 7) and in human breast and pancreatic cancer biopsies, see FIG. 11 (Supplementary FIG. 8) and a strong correlation was found between αvβ3 expression and Ral GTPase activity in patients biopsies suggesting the αvβ3/RalB signaling module is clinically relevant, see FIG. 7e. Together, these findings indicate that integrin αvβ3 promotes erlotinib resistance of cancer cells by complexing with KRAS and RalB resulting in RalB activation.

RalB, an effector of RAS has been shown to induce TBK1/NF-κB activation leading to enhanced tumor cell survival[25,26]. In addition, it has been shown that NF-κB signaling is essential for KRAS-driven tumor growth and resistance to EGFR blockade[27-29]. This prompted us to ask whether αvβ3 could regulate NF-κB activity through RalB activation and thereby promote tumor cell resistance to EGFR targeted therapy. To test this, tumor cells expressing or lacking integrin αvβ3 and/or RalB were grown in the presence or absence of erlotinib and lysates of these cells were analyzed for activated downstream effectors of RalB. We found that erlotinib treatment of αvβ3 negative cells reduced levels of phosphorylated TBK1 and NF-κB, whereas in β3-positive cells these effectors remained activated unless RalB was depleted, see FIG. 4a. NF-κB activity was sufficient to account for EGFR inhibitor resistance since ectopically expressed a constitutively active NF-κB (S276D) in β3-negative FG pancreatic tumor cells[30] conferred resistance to EGFR inhibition, see FIG. 4b). Accordingly, genetic or pharmacological inhibition of NF-κB in β3-positive cells completely restored erlotinib sensitivity[31], see FIGS. 4c and d). These findings demonstrate that RalB, the effector of the αvβ3/KRAS complex, promotes tumor cell resistance to EGFR targeted therapy via TBK1/NF-κB activation. Together, our studies describe a role for αvβ3 mediating resistance to EGFR inhibition via RalB activation and its downstream effector NF-κB, opening new avenues to target tumors that are resistant to EGFR targeted therapy, see FIG. 4e.

Recent studies have shown that, upon prolonged treatment with EGFR inhibitors, tumor cells develop alternative or compensatory pathways to sustain cell survival, leading to drug resistance[1,32]. Here we show that integrin αvβ3 is specifically upregulated in histologically distinct tumors where it accounts for resistance to EGFR inhibition. At present, it is not clear whether exposure to EGFR inhibitors may promote increased αvβ3 expression or whether these drugs simply eliminate cells lacking αvβ3 allowing the expansion of αvβ3-expressing tumor cells. Given that integrin αvβ3 is a marker of mammary stem cells[15], it is possible that acquired resistance to EGFR inhibitors selects for a tumor stem-like cell population[3,33]. While integrins can promote adhesion dependent cell survival and induce tumor progression[16], here, we show that integrin αvβ3, even in the unligated state, can drive tumor cell survival and resistance to EGFR blockade by interaction with KRAS. This action leads to the recruitment and activation of RalB and its downstream signaling effector NF-κB. In fact, NF-κB inhibition re-sensitizes αvβ3-bearing tumors to EGFR blockade. Taken together, our findings not only identify αvβ3 as a tumor cell marker of drug resistance but reveal that inhibitors of EGFR and NF-κB should provide synergistic activity against a broad range of cancers.

Figure Legends

FIG. 1. Integrin αvβ3 expression promotes resistance to EGFR TKI.

(a) Flow cytometric quantification of cell surface markers after 3 weeks treatment with erlotinib (pancreatic and colon cancer cells) or lapatinib (breast cancer cells). (b) Flow cytometric analysis of αvβ3 expression in FG and Miapaca-2 cells following erlotinib. Error bars represent s.d. (n=3 independent experiments). (c) Top, immunofluorescence staining of integrin αvβ3 in tissue specimens obtained from orthotopic pancreatic tumors treated with vehicle (n=3) or erlotinib (n=4). Scale bar, 50 μm. Bottom, Integrin αvβ3 expression was quantified as ratio of integrin αvβ3 pixel area over nuclei pixel area using Metamorph (*P=0.049 using Mann-Whitney U test). (d) Right, intensity (scale 0 to 3) of β3 expression in mouse orthotopic lung tumors treated with vehicle (n=8) or erlotinib (n=7). Left, immunohistochemical staining of β3. Scale bar, 100 μm. (**P=0.0012 using Mann-Whitney U test) (e) $IC_{50}$ for cells treated with erlotinib or lapatinib. (f) Tumor sphere formation assay to establish a dose-response for erlotinib. Error bars represent s.d. (n=3 independent experiments). (g) Orthotopic FG tumors (>1000 mm$^3$; n=10 per treatment group) were treated for 10 days with vehicle or erlotinib. Results are expressed as % tumor weight compared to vehicle control. *P<0.05 Immunoblot analysis for tumor lysates after 10 days of erlotinib confirms suppressed EGFR phosphorylation.

FIG. 2. Integrin αvβ3 cooperates with KRAS to promote resistance to EGFR blockade.

(a-b) Tumor sphere formation assay of FG expressing (a) or lacking (b) integrin β3 depleted of KRAS (shKRAS) or not (shCTRL) and treated with a dose response of erlotinib. Error bars represent s.d. (n=3 independent experiments). (c) Confocal microscopy images of PANC-1 and FG-β3 cells grown in suspension. Cells are stained for integrin αvβ3 (green), KRAS (red), and DNA (TOPRO-3, blue). Scale bar, 10 m. Data are representative of three independent experiments. (d) RAS activity assay performed in PANC-1 cells using GST-Rafl-RBD immunoprecipitation as described in Methods Immunoblot analysis of KRAS, NRAS, HRAS, RRAS, integrin β1 and integrin β3. Data are representative of three independent experiments. (e) Immunoblot analysis of Integrin αvβ3 immunoprecipitates from BxPC-3 β3-positive cells grown in suspension and untreated or treated with EGF 50 ng/ml for 5 minutes. RAS activity was determined using a GST-Rafl-RBD immunoprecipitation assay. Data are representative of three independent experiments.

FIG. 3. RalB is a key modulator of integrin αvβ3-mediated EGFR TKI resistance.

(a) Tumor spheres formation assay of FG-β3 treated with non-silencing (shCTRL) or RalB-specific shRNA and exposed to a dose response of erlotinib. Error bars represent s.d. (n=3 independent experiments). Immunoblot analysis showing RalB knockdown. (b) Effects of depletion of RalB on erlotinib sensitivity in β3-positive tumor in a pancreatic orthotopic tumor model. Established β3-positive tumors expressing non-silencing (shCTRL) or RalB-specific shRNA (>1000 mm$^3$; n=13 per treatment group) were randomized and treated for 10 days with erlotinib. Results are expressed as % of tumor weight changes after erlotinib treatment compared to control. *P<0.05, **P<0.01. Tumor images, average weights+/−s.e are shown. (c) Tumor spheres formation assay of FG cells ectopically expressing vector control, WT RalB FLAG tagged constructs or a constitutively active RalB G23V FLAG tagged treated with erlotinib (0.5 μM). Error bars represent s.d. (n=3 independent experiments). *P<0.05, NS=not significant. Immunoblot analysis showing RalB WT and RalB G23 FLAG tagged constructs transfection efficiency. (d) RalB activity was determined in FG, FG-β3 expressing non-silencing or KRAS-specific shRNA, by using a GST-RalBP1-RBD immunoprecipitation assay as described in Methods. Data are representative of three independent experiments. (e) Right, overall active Ral immunohistochemical staining intensity between β3 negative (n=15) and β3 positive (n=70) human tumors. Active Ral staining was compared between each group by Fisher's exact test (*P<0.05, P=0.036, two-sided). Left, representative immunohistochemistry images of human tumor tissues stained with an integrin β3-specific antibody and an active Ral antibody. Scale bar, 50 μm.

FIG. 4. Integrin αvβ3/RalB complex leads to NF-μB activation and resistance to EGFR TKI.

Immunoblot analysis of FG, FG-β3 and FG-β3 stably expressing non-silencing or RalB-specific ShRNA, grown in suspension and treated with erlotinib (0.5 μM). pTBK1 refers to phospho-S172 TBK1, p-p65 NF-κB refers to phospho-p65 NF-κB S276, pFAK refers to phospho-FAK Tyr 861. Data are representative of three independent experiments. (b) Tumor spheres formation assay of FG cells ectopically expressing vector control, WT NF-κB FLAG tagged or constitutively active S276D NF-κB FLAG tagged constructs treated with erlotinib (0.5 μM). Error bars represent s.d. (n=3 independent experiments). *P<0.05, **P<0.001, NS=not significant Immunoblot analysis showing NF-κB WT and S276D NF-κB FLAG transfection efficiency. (c) Tumor spheres formation assay of FG-β3 treating with non-silencing (shCTRL) or NF-κB-specific shRNA and exposed to erlotinib (0.5 μM). Error bars represent s.d. (n=3 independent experiments). *P<0.05, NS=not significant. (d) Dose response in FG-β3 cells treated with erlotinib (10 nM to 5 μM), lenalidomide (10 nM to 5 μM) or a combination of erlotinib (10 nM to 5 μM) and lenalidomide (1 μM). Error bars represent s.d. (n=3 independent experiments). *P<0.05, NS=not significant. (e) Model depicting the integrin αvβ3-mediated EGFR TKI resistance and conquering EGFR TKI resistance pathway and its downstream RalB and NF-κB effectors.

Methods

Compounds and Cell Culture.

Human pancreatic (FG, PANC-1, Miapaca-2 (MP2), CFPAC-1, XPA-1, CAPAN-1, BxPc3), breast (MDAMB231, MDAMB468 (MDA468), BT20, SKBR3, BT474), colon (SW480) and lung (A549, H441) cancer cell lines were grown in ATCC recommended media supplemented with 10% fetal bovine serum, glutamine and non-essential amino acids. We obtained FG-β3, FG-D119A mutant and PANC-shβ3 cells as previously described[17]. Erlotinib, OSI-906, Gemcitabine and Lapatinib were purchased from Chemietek. Cisplatin was generated from Sigma-Aldrich. Lenalidomide was purchased from LC Laboratories. We established acquired EGFR™ resistant cells by adding an increasing concentration of erlotinib (50 nM to 15 μM) or lapatinib (10 nM to 15 μM), daily in 3D culture in 0.8% methylcellulose.

Lentiviral Studies and Transfection.

Cells were transfected with vector control, WT, G23V RalB-FLAG, WT and S276D NF-κB-FLAG using a lentiviral system. For knock-down experiments, cells were transfected with KRAS, RalA, RalB, AKT1, ERK1/2, p65 NF-κB siRNA (Qiagen) using the lipofectamine reagent (Invitrogen) following manufacturer's protocol or transfected with shRNA (Open Biosystems) using a lentiviral system. Gene silencing was confirmed by immunoblots analysis.

Tumor Sphere Formation.

Tumor spheres formation assays were performed essentially as described previously[17]. Briefly, cells were seeded at 1000 to 2000 cells per well and grown for 12 days to 3 weeks. Cells were treated with vehicle (DMSO), erlotinib (10 nM to 5 μM), lapatinib (10 nM to 5 μM), gemcitabine (0.001 nM to 5 μM), OSI-906 (10 nM to 5 μM), lenalidomide (10 nM to 5 μM), or cisplatin (10 nM to 5 μM), diluted in DMSO. The media was replaced with fresh inhibitor every day for erlotinib, lapatinib, lenalidomide and 3 times a week for cisplatin and gemcitabine. Colonies were stained with crystal violet and scored with an Olympus SZH10 microscope. Survival curves were generated at least with five concentration points.

Flow Cytometry.

200,000 cells, after drug or vehicle treatment, were washed with PBS and incubated for 20 minutes with the Live/Dead reagent (Invitrogen) according to the manufacturer's instruction, then, cells were fixed with 4% paraformaldehyde for 15 min and blocked for 30 min with 2% BSA in PBS. Cells were stained with fluorescent-conjugated antibodies to CD61 (LM609), CD44 (eBioscience), CD24 (eBioscience), CD34 (eBioscience), CD133 (Santa Cruz), CD56 (eBioscience), CD29 (P4C10) and CD49f (eBioscience). All antibodies were used at 1:100 dilutions, 30 minutes at 4° C. After washing several times with PBS, cells were analyzed by FACS.

Immunohistochemical Analysis.

Immunostaining was performed according to the manufacturer's recommendations (Vector Labs) on 5 μM sections of paraffin-embedded tumors from the orthotopic xenograft pancreas and lung cancer mouse models[14] or from a metastasis tissue array purchased from US Biomax (MET961). Antigen retrieval was performed in citrate buffer pH 6.0 at 95° C. for 20 min. Sections were treated with 0.3% $H_2O_2$ for 30 min, blocked in normal goat serum, PBS-T for 30 min followed by Avidin-D and then incubated overnight at 4° C. with primary antibodies against integrin β3 (Abeam) and active Ral (NewEast) diluted 1:100 and 1:200 in blocking solution. Tissue sections were washed and then incubated with biotinylated secondary antibody (1:500, Jackson ImmunoResearch) in blocking solution for 1 h. Sections were washed and incubated with Vectastain ABC (Vector Labs) for 30 min. Staining was developed using a Nickel-enhanced diamino-benzidine reaction (Vector Labs) and sections were counter-stained with hematoxylin. Sections stained with integrin β3 and active Ral were scored by a H-score according to the staining intensity (SI) on a scale 0 to 3 within the whole tissue section.

Immunoprecipitation and Immunoblot Analysis.

Cells were lysed in either RIPA lysis buffer (50 mM Tris pH 7.4, 100 mM NaCL, 2 mM EDTA, 10% DOC, 10% Triton, 0.1% SDS) or Triton lysis buffer (50 mM Tris pH 7.5, 150 mN NaCl, 1 mM EDTA, 5 mM $MgCl2$, 10% Glycerol, 1% Triton) supplemented with complete protease and phosphatase inhibitor mixtures (Roche) and centrifuged at 13,000 g for 10 min at 4° C. Protein concentration was determined by BCA assay. 500 μg to 1 mg of protein were immunoprecipitated with 3 μg of anti-integrin αvβ-3 (LM609) overnight at 4° C. following by capture with 25 μl of protein A/G (Pierce). Beads were washed five times, eluted in Laemmli buffer, resolved on NuPAGE 4-12% Bis-Tris Gel (Invitrogen) and immunoblotting was performed with anti-integrin β3 (Santa Cruz), anti-RalB (Cell Signaling Technology), anti KRAS (Santa Cruz). For immunoblot analysis, 25 μg of protein was boiled in Laemmli buffer and resolved on 8% to 15% gel. The following antibodies were used: KRAS (Santa Cruz), NRAS (Santa Cruz), RRAS (Santa Cruz), HRAS (Santa Cruz), phospho-S172 NAK/TBK1 (Epitomics), TBK1 (Cell Signaling Technology), phospho-p65NF-κB S276 (Cell Signaling Technology), p65NF-κB (Cell Signaling Technology), RalB (Cell Signaling Technology), phospho-EGFR (Cell Signaling Technology), EGFR (Cell Signaling Technology), FLAG (Sigma), phospho-FAK Tyr 861 (Cell Signaling Technology), FAK (Santa Cruz), Galectin 3 (BioLegend) and Hsp90 (Santa Cruz).

Affinity Pull-Down Assays for Ras and Ral.

RAS and Ral activation assays were performed in accordance with the manufacturer's (Upstate) instruction. Briefly, cells were cultured in suspension for 3 h, lysed and protein concentration was determined. 10 μg of Ral Assay Reagent (Ral BP1, agarose) or RAS assay reagent (Raf-1 RBD, agarose) was added to 500 mg to 1 mg of total cell protein in MLB buffer (Millipore). After 30 min of rocking at 4° C., the activated (GTP) forms of RAS/Ral bound to the agarose beads were collected by centrifugation, washed, boiled in Laemmli buffer, and loaded on a 15% SDS-PAGE gel.

Immunofluorescence Microscopy.

Frozen sections from tumors from the orthotopic xenograft pancreas cancer mouse model or from patients diagnosed with pancreas or breast cancers (as approved by the institutional Review Board at University of California, San Diego) or tumor cell lines were fixed in cold acetone or 4% paraformaldehyde for 15 min, permeabilized in PBS containing 0.1% Triton for 2 min and blocked for 1 h at room temperature with 2% BSA in PBS. Cells were stained with antibodies to integrin αvβ3 (LM609), RalB (Cell Signaling Technology), Galectin 3 (BioLegend), pFAK (Cell Signaling Technology), NRAS (Santa Cruz), RRAS (Santa Cruz), HRAS (Santa Cruz) and KRAS (Abgent). All primary antibodies were used at 1:100 dilutions, overnight at 4° C. Where mouse antibodies were used on mouse tissues, we used the MOM kit (Vector Laboratory). After washing several times with PBS, cells were stained for two hours at 4° C. with secondary antibodies specific for mouse or rabbit (Invitrogen), as appropriate, diluted 1:200 and co-incubated with the DNA dye TOPRO-3 (1:500) (Invitrogen). Samples were mounted in VECTASHIELD hard-set media (Vector Laboratories) and imaged on a Nikon Eclipse C1 confocal microscope with 1.4 NA 60× oil-immersion lens, using minimum pinhole (30 m). Images were captured using 3.50 imaging software. Colocalization between Integrin αvβ3 and KRAS was studied using the Zenon Antibody Labeling Kits (Invitrogen).

Orthotopic Pancreas Cancer Xenograft Model.

All mouse experiments were carried out in accordance with approved protocols from the UCSD animal subjects committee and with the guidelines set forth in the NIH Guide for the Care and Use of Laboratory Animals. Tumors were generated by injection of FG human pancreatic carcinoma cells ($10^6$ tumor cells in 30 μL of sterile PBS) into the tail of the pancreas of 6-8 week old male immune compromised nu/nu mice. Tumors were established for 2-3 weeks (tumor sizes were monitored by ultrasound) before beginning dosing. Mice were dosed by oral gavage with vehicle (6% Captisol) or 100 mg/kg/day erlotinib for 10 to 30 days prior to harvest.

Orthotopic Lung Cancer Xenograft Model.

Tumors were generated by injection of H441 human lung adenocarcinoma cells ($10^6$ tumor cells per mouse in 50 μL of HBSS containing 50 mg growth factor-reduced Matrigel (BD Bioscience) into the left thorax at the lateral dorsal axillary line and into the left lung, as previously described[14] of 8 week old male immune-compromised nu/nu mice. 3 weeks after tumor cell injection, the mice were treated with vehicle or erlotinib (100 mg/kg/day) by oral gavage until moribund (approximately 50 and 58 days, respectively).

Statistical Analyses.

All statistical analyses were performed using Prism software (GraphPad). Two-tailed Mann Whitney U tests, Fisher's exact tests, or t-tests were used to calculate statistical significance. A P value<0.05 was considered to be significant.

References—Example 1
1. Wheeler, D. L., Dunn, E. F. & Harari, P. M. Understanding resistance to EGFR inhibitors-impact on future treatment strategies. Nat Rev Clin Oncol 7, 493-507 (2010).
2. Dorans, K. Outpacing cancer. Nature Medicine 15, 718-722 (2009).
3. Dean, M., Fojo, T. & Bates, S. Tumour stem cells and drug resistance. Nature Reviews 5, 275-284 (2005).
4. Engelman, J. A. & Janne, P. A. Mechanisms of acquired resistance to epidermal growth factor receptor tyrosine kinase inhibitors in non-small cell lung cancer. Clin Cancer Res 14, 2895-2899 (2008).
5. Montagut, C., et al. Identification of a mutation in the extracellular domain of the Epidermal Growth Factor Receptor conferring cetuximab resistance in colorectal cancer. Nature Medicine 18, 221-223 (2012).
6. Sharma, S. V., Bell, D. W., Settleman, J. & Haber, D. A. Epidermal growth factor receptor mutations in lung cancer. Nature Reviews 7, 169-181 (2007).
7. Zoppoli, G., et al. Ras-induced resistance to lapatinib is overcome by MEK inhibition. Current Cancer Drug Targets 10, 168-175 (2010).
8. Gupta, S., et al. Binding of ras to phosphoinositide 3-kinase p110alpha is required for ras-driven tumorigenesis in mice. Cell 129, 957-968 (2007).
9. Lim, K. H., et al. Activation of RalA is critical for Ras-induced tumorigenesis of human cells. Cancer Cell 7, 533-545 (2005).
10. Sharma, S. V., et al. A chromatin-mediated reversible drug-tolerant state in cancer cell subpopulations. Cell 141, 69-80 (2010).
11. Liu, C., et al. The microRNA miR-34a inhibits prostate cancer stem cells and metastasis by directly repressing CD44. Nature Medicine 17, 211-215 (2011).
12. Vaillant, F., et al. The mammary progenitor marker CD61/beta3 integrin identifies cancer stem cells in mouse models of mammary tumorigenesis. Cancer Research 68, 7711-7717 (2008).
13. Adhikari, A. S., Agarwal, N. & Iwakuma, T. Metastatic potential of tumor-initiating cells in solid tumors. Front Biosci 16, 1927-1938 (2011).
14. Cascone, T., et al. Upregulated stromal EGFR and vascular remodeling in mouse xenograft models of angiogenesis inhibitor-resistant human lung adenocarcinoma. J Clin Invest 121, 1313-1328 (2011).

15. Asselin-Labat, M. L., et al. Gata-3 is an essential regulator of mammary-gland morphogenesis and luminal-cell differentiation. Nature Cell Biology 9, 201-209 (2007).
16. Desgrosellier, J. S. & Cheresh, D. A. Integrins in cancer: biological implications and therapeutic opportunities. Nature Reviews 10, 9-22 (2010).
17. Desgrosellier, J. S., et al. An integrin alpha(v)beta(3)-c-Src oncogenic unit promotes anchorage-independence and tumor progression. Nature Medicine 15, 1163-1169 (2009).
18. Borst, P., Jonkers, J. & Rottenberg, S. What makes tumors multidrug resistant? Cell Cycle 6, 2782-2787 (2007).
19. Schmitt, C. A., et al. A senescence program controlled by p53 and p16INK4a contributes to the outcome of cancer therapy. Cell 109, 335-346 (2002).
20. Baselga, J. & Rosen, N. Determinants of RASistance to anti-epidermal growth factor receptor agents. J Clin Oncol 26, 1582-1584 (2008).
21. Moore, M. J., et al. Erlotinib plus gemcitabine compared with gemcitabine alone in patients with advanced pancreatic cancer: a phase III trial of the National Cancer Institute of Canada Clinical Trials Group. J Clin Oncol 25, 1960-1966 (2007).
22. Levy, R., Grafi-Cohen, M., Kraiem, Z. & Kloog, Y. Galectin-3 promotes chronic activation of K-Ras and differentiation block in malignant thyroid carcinomas. Molecular Cancer Therapeutics 9, 2208-2219 (2010).
23. Markowska, A. I., Liu, F. T. & Panjwani, N. Galectin-3 is an important mediator of VEGF- and bFGF-mediated angiogenic response. The Journal of Experimental Medicine 207, 1981-1993 (2010).
24. Buday, L. & Downward, J. Many faces of Ras activation. Biochim Biophys Acta 1786, 178-187 (2008).
25. Barbie, D. A., et al. Systematic RNA interference reveals that oncogenic KRAS-driven cancers require TBK1. Nature 462, 108-112 (2009).
26. Chien, Y., et al. RalB GTPase-mediated activation of the IkappaB family kinase TBK1 couples innate immune signaling to tumor cell survival. Cell 127, 157-170 (2006).
27. Ling, J., et al. Kras(G12D)-Induced IKK2/beta/NF-kappaB Activation by IL-1 alpha and p62 Feedforward Loops Is Required for Development of Pancreatic Ductal Adenocarcinoma. Cancer Cell 21, 105-120 (2012).
28. Bivona, T. G., et al. FAS and NF-kappaB signalling modulate dependence of lung cancers on mutant EGFR. Nature 471, 523-526 (2011).
29. Min, J., et al. An oncogene-tumor suppressor cascade drives metastatic prostate cancer by coordinately activating Ras and nuclear factor-kappaB. Nature Medicine 16, 286-294 (2010).
30. Dong, J., Jimi, E., Zeiss, C., Hayden, M. S. & Ghosh, S. Constitutively active NF-kappaB triggers systemic TNFalpha-dependent inflammation and localized TNFalpha-independent inflammatory disease. Genes & Development 24, 1709-1717 (2011).
31. Braun, T., et al. Targeting NF-kappaB in hematologic malignancies. Cell Death Differ 13, 748-758 (2006).
32. Workman, P. & Clarke, P. A. Resisting targeted therapy: fifty ways to leave your EGFR. Cancer Cell 19, 437-440 (2011).
33. Lewis, M. T. & Wicha, M. S. Tumor-initiating cells and treatment resistance: how goes the war? Journal of Mammary Gland Biology and Neoplasia 14, 1-2 (2009).

Example 2

Methods of the Invention are Effective for Sensitizing and Re-Sensitizing Cancer Cells to Growth Factor Inhibitors The data presented herein demonstrates the effectiveness of the compositions and methods of the invention in sensitizing and re-sensitizing cancer cells, and cancer stem cells, to growth factor inhibitors, and validates this invention's therapeutic approach to overcome growth factor inhibitor resistance for a wide range of cancers. In particular, the data presented in this Example demonstrates that β3 integrin induces erlotinib resistance in cancer cells by switching tumor dependency from EGFR to KRAS.

In alternative embodiments, the compositions and methods of the invention overcome tumor drug resistance that limits the long-term success of therapies targeting EGFR. Here, we identify integrin αvβ3 as a biomarker of intrinsic and acquired resistance to erlotinib in human pancreatic and lung carcinomas irrespective of their KRAS mutational status. Functionally, αvβ3 is necessary and sufficient for this resistance where it acts in the unligated state as a scaffold to recruit active KRAS into membrane clusters switching tumor dependency from EGFR to KRAS. The KRAS effector RalB is recruited to this complex, where it mediates erlotinib resistance via a TBK-1/NF-κB pathway. Disrupting assembly of this complex or inhibition of its downstream effectors fully restores tumor sensitivity to EGFR blockade. Our findings uncouple KRAS mutations from erlotinib resistance, revealing an unexpected requirement for integrin αvβ3 in this process.

We hypothesized that upregulation of specific genes common to multiple tumor types exposed to erlotinib drives a conserved pathway that governs both intrinsic and acquired resistance. To identify genes associated with erlotinib (N-(3-ethynylphenyl)-6,7-bis(2-methoxyethoxy) quinazolin-4-amine) resistance, we analyzed the expression of a tumor progression gene array for human cell lines with intrinsic resistance or murine xenografts following the acquisition of resistance in vivo. The most upregulated gene common to all drug resistant carcinomas tested was the cell surface ITGB3, integrin β3 (FIG. 1A, and table S1) associated with the integrin αvβ3 whose expression has been linked to tumor progression. αvβ3 expression completely predicted erlotinib resistance for a panel of histologically distinct tumor cell lines (FIG. 1B and FIG. S1B). Moreover, chronic treatment of the erlotinib sensitive lines resulted in the induction of β3 expression concomitantly with drug resistance (FIG. 1C and FIG. S1B, C). We also detected increased β3 expression in lung carcinoma patients who had progressed on erlotinib therapy (FIG. S2). In addition, we examined both treatment naive and erlotinib resistant NSCLC patients from the BATTLE Study (10) of non-small cell lung cancer (NSCLC) and found β3 gene expression was significantly higher in patients who progressed on erlotinib (FIG. 1D). Finally, we examined serial primary lung tumors biopsies from patients before treatment or after erlotinib resistance and found a qualitative increase in integrin β3 expression concurrent with the loss of erlotinib sensitivity (FIG. 1E). Taken together, our findings show that integrin β3 is a marker of acquired and intrinsic erlotinib resistance for pancreas and lung cancer.

To assess the functional role of αvβ3 in erlotinib resistance we used a gain and loss-of-function approach and found that integrin β3 was both necessary and sufficient to account for erlotinib resistance in vitro and during systemic treatment of lung and orthotopic pancreatic tumors in vivo (FIG. 1F, G and FIG. S3A-C). Interestingly, integrin β3 expression did not impact resistance to chemotherapeutic agents such as gemcitabine and cisplatin while conferring resistance to inhibitors targeting EGFR1/EGFR2 or IGFR (FIG. S3C-E), suggesting this integrin plays a specific role in tumor cell resistance to RTK inhibitors.

As integrin αvβ3 is functions as an adhesion receptor, ligand binding inhibitors could represent a therapeutic strategy to sensitize tumors to EGFR inhibitors. However, αvβ3 expression induced drug resistance in cells growing in suspension. Also, neither function blocking antibodies nor cyclic peptide inhibitors sensitized integrin αvβ3-expressing tumors to EGFR inhibitors (not shown), and tumor cells expressing wild-type integrin β3 or the ligation-deficient mutant β3 D119A (11) showed equivalent drug resistance (FIG. S4). Since the contribution of integrin αvβ3 to erlotinib resistance appears to involve a non-canonical, ligation-independent mechanism that is not sensitive to traditional integrin antagonists, understanding the molecular mechanisms driving this pathway could provide therapeutic opportunities.

Integrins function in the context of RAS family members. Interestingly, we found that αvβ3 associated with KRAS but not N-, H- or R-RAS (FIG. 2A). While oncogenic KRAS has been linked to erlotinib resistance, there are many notable exceptions (6-9). In fact, we observed a number of tumor cell lines with oncogenic KRAS to be sensitive to erlotinib (FG, H441, and CAPAN1), whereas H1650 cells were erlotinib resistant despite their expression of wildtype KRAS and mutant EGFR (table S2). In fact, αvβ3 expression consistently correlated with erlotinib resistance for all cell lines tested (Pearson's correlation coefficient $R^2$=0.87) making a better predictor of erlotinib resistance. Interestingly, we observed active KRAS to be distributed within the cytoplasm in β3-negative cells (FIG. S5A) whereas in cells expressing β3 endogenously or ectopically, KRAS was localized to β3-containing membrane clusters, even in the presence of erlotinib (FIG. 2B,C and FIG. S5A) a relationship that was not observed for β1 integrin (FIGS. S5B and C). Furthermore, knockdown of KRAS impaired tumorsphere formation and restored erlotinib sensitivity in β3-positive cells (FIG. 2D-F and FIG. S6A-C). In contrast, KRAS was dispensable for tumorsphere formation and erlotinib response the in cells lacking β3 expression (FIG. 2D-F). Thus, β3 integrin expression switches tumor cell dependency from EGFR to KRAS, and that the localization of β3 with KRAS at the plasma membrane appears to be a critical determinant of tumor cell resistance to erlotinib. Also, our results reveal that tumors expressing oncogenic KRAS without β3 remain sensitive to EGFR blockade.

Independent studies have shown that galectin-3 can interact with either KRAS (12) or β3 (13) so we asked whether this protein might serve as an adaptor to promote KRAS/β3 complex formation. Under anchorage-independent growth conditions, integrin β3, KRAS, and Galectin-3 were co-localized in membrane clusters (FIG. 2G and FIG. S7), and knockdown of either integrin β3 or Galectin-3 prevented complex formation, KRAS membrane localization, and importantly sensitized αvβ3 expressing tumors to erlotinib (FIG. 2G-I).

Figure 4B:
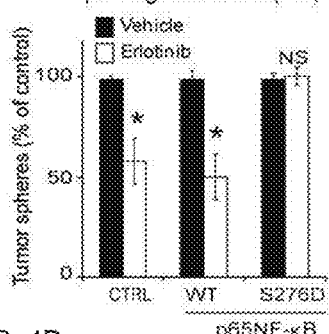
FIG. 4(b) illustrates tumor spheres formation assay of FG cells ectopically expressing vector control, WT NF-κB FLAG tagged or constitutively active S276D NF-κB FLAG tagged constructs treated with erlotinib.
Figure 4C:
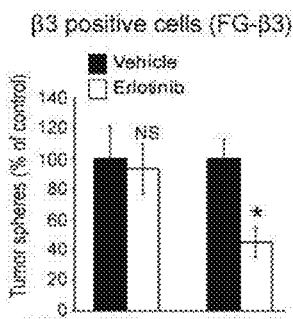
FIG. 4(c) illustrates tumor spheres formation assay of FG-β3 treating with non-silencing (shCTRL) or NF-κB-specific shRNA and exposed to erlotinib.
Figure 4D:
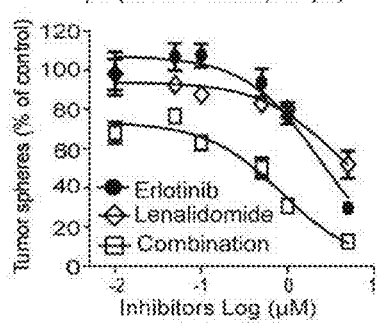
FIG. 4(d) illustrates dose response in FG-β3 cells treated with erlotinib (10 nM to 5 μM), lenalidomide (10 nM to 5 μM) or a combination of erlotinib (10 nM to 5 μM) and lenalidomide (1 μM)
Figure 4E:
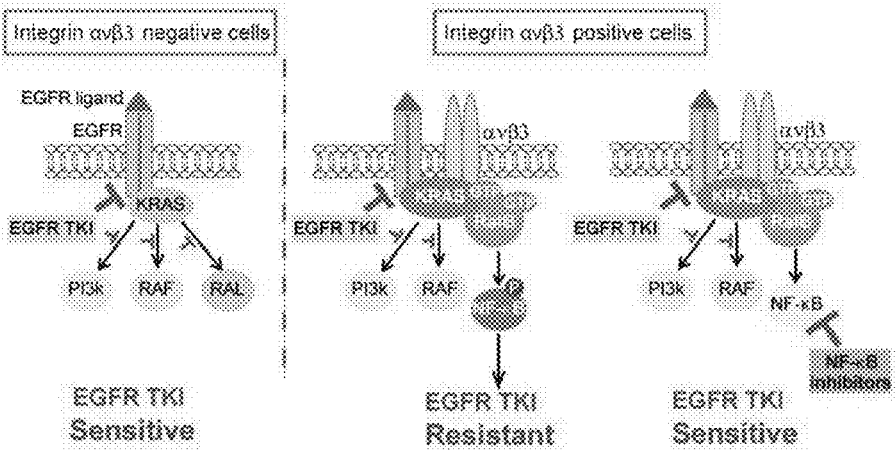
FIG. 4(e) illustrates Model depicting the integrin avβ3-mediated EGFR TKI resistance and conquering EGFR™ resistance pathway and its downstream RalB and NF-κB effectors; as discussed in detail in Example 1, below.

We next evaluated the signaling pathways driven by the integrin β3/KRAS complex. Erlotinib resistance of β3-positive cells was not affected by depletion of known KRAS effectors, including AKT, ERK, or RalA (FIG. S8A,B). However, knockdown of RalB sensitized β3-expressing cells to erlotinib in vitro (FIG. 3A and FIG. S8A-C) and in pancreatic orthotopic tumors in vivo (FIG. 3B). Accordingly, expression of constitutively active RalB in β3-negative cells conferred erlotinib resistance (FIG. 3C). Mechanistically, RalB was recruited to the β3/KRAS membrane clusters (FIG. 3D-F) where it became activated in a KRAS-dependent manner (FIG. 3G). Recent studies have reported that TBK1 and NF-κB are RalB effectors linked to KRAS dependency (14) and erlotinib resistance (15). We found that erlotinib decreased the activation of these effectors only in the absence of integrin β3 (FIG. 3H). In fact, loss of RalB in β3-expressing cells restored erlotinib-mediated inhibition of TBK1 and NF-κB (FIG. 3H). Accordingly, depletion of either TBK1 or NF-κB sensitized β3-positive cells to erlotinib (FIG. 3I and FIG. S9A), while ectopic expression of activated NF-κB was sufficient to promote drug resistance in β3-negative cells (FIG. S9B). To evaluate the therapeutic potential of targeting this pathway, we examined whether erlotinib resistance of β3-expressing tumors could be reversed with approved drugs known to suppress NF-κB activation, lenalidomide/REVLIMID®(16) and bortezomib/VELCADE® (17). While monotherapy with these drugs failed to impact tumor growth, either drug used combination with erlotinib decreased tumorsphere formation in vitro (FIG. 4A) and completely suppressed tumor growth in vivo (FIG. 4B, C and FIG. S10). These findings support the model depicted in FIG. 4D where inhibition of NF-κB restores erlotinib sensitivity in β3 expressing tumors. These findings support the model depicted in FIG. 4D that αvβ3 expression in lung and pancreatic tumors recruits oncogenic KRAS facilitating NFκB activity leading to erlotinib resistance which can be overcome by a combination of currently approved inhibitors of NF-κB and EGFR.

Figure 40B:
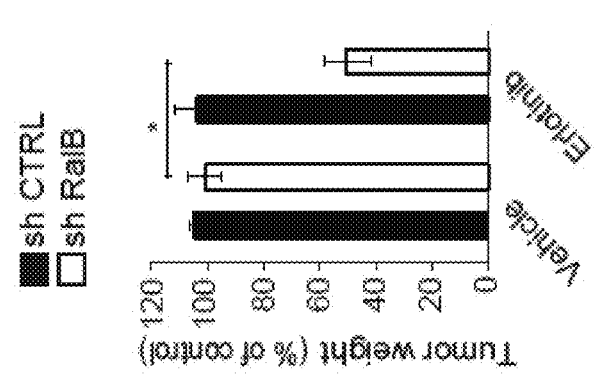
FIG. 40B graphically illustrates tumor weight as a percent of control, in in vivo orthotopic pancreas xenograft; as discussed in detail in Example 2, below.
Figure 40A:
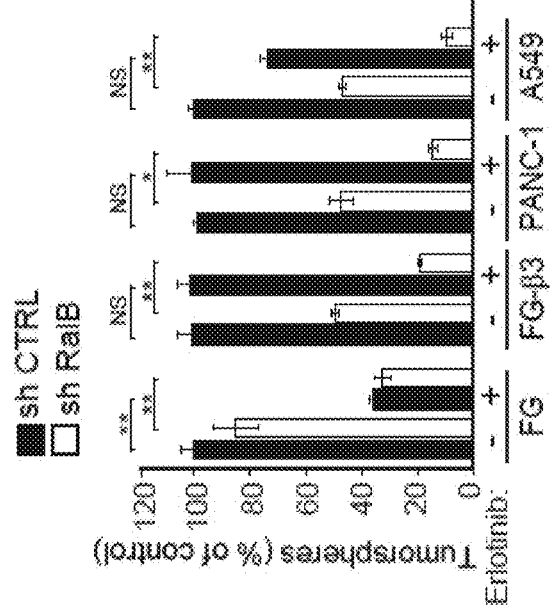
FIG. 40A graphically illustrates number of tumorspheres as a percent of control for FG, FG-beta3, PANC-1, and A539 expressing cells, with or without erlotinib, in vitro soft agar conditions.
Figures 41A, 41B, 41C:
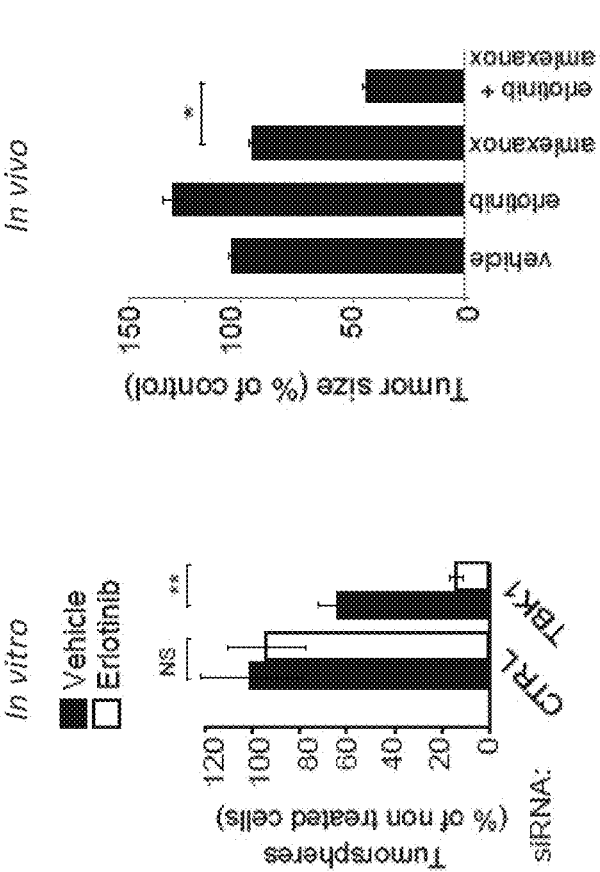
FIG. 41A illustrates data demonstrating that integrin mediates TBK1 activation through Ral b.
FIG. 41B and FIG. 41C graphically illustrate data demonstrating TBK1 depletion (with siRNA) overcomes integrin beta-3-mediated erlotinib resistance, where

See also FIG. 40 and FIG. 41, graphically illustrating data demonstrating that depletion of RalB overcomes erlotinib resistance in KRAS mutant cells, and depletion of TBK1 overcomes erlotinib resistance in KRAS mutant cells, respectively. In FIG. 41: Integin b3 mediates TBK1 activation through RalB and TBK1 depletion overcomes integrin b3-mediated erlotinib resistance.

Our observations demonstrate that the ability of β3 integrin to recruit KRAS into a membrane complex along with Galectin-3 and RalB functions to switch tumor cell dependency from EGFR to KRAS. In fact, oncogenic KRAS requires this non-canonical β3-mediated pathway to drive erlotinib resistance. We show that currently available approved inhibitors of this pathway can be used to practice the methods of this invention to treat patients with solid tumors, rendering them sensitive to EGFR inhibitors such as erlotinib.

Material and Methods

Compounds and cell culture. Human pancreatic (FG, PANC-1, CFPAC-1, XPA-1, HPAFII, CAPAN-1, BxPC3) and lung (A549, H441, HCC827 and H1650) cancer cell lines were grown in ATCC recommended media supplemented with 10% fetal bovine serum, glutamine and non-essential amino acids. We obtained FG-β3, FG-D119A mutant and PANC-shβ3 cells as previously described (10). Erlotinib, OSI-906, Gemcitabine, Bortezomib and Lapatinib were purchased from Chemietek. Cisplatin was generated from Sigma-Aldrich. Lenalidomide was purchased from LC Laboratories. Gene expression analysis. The Tumor Metastasis PCR Array (Applied Biosystem), consisting of 92 genes known to be involved in tumor progression and metastasis, was used to profile the common genes upregulated in erlotinib-resistant cells compared to erlotinib-sensitive cells according to the manufacturer's instructions. Briefly, total RNA was extracted and reverse transcribed into cDNA using the RNeasy kit (Qiagen). The cDNA was combined with a SYBR Green qPCR Master Mix (Qiagen), and then added to each well of the same PCR Array plate that contained the predispensed gene-specific primer sets.

Tumor digestion and Flow Cytometry. Fresh tumor tissue from lung cancer cell lines was mechanically dissociated and then enzymatically digested in trypsin. The tissue was further filtered through a cell strainer to obtain a suspension of single tumor cells. Then, cells were washed were washed with PBS and incubated for 20 minutes with the Live/Dead reagent (Invitrogen) according to the manufacturer's instruction, then, cells were fixed with 4% paraformaldehyde for 15 min and blocked for 30 min with 2% BSA in PBS. Cells were stained with fluorescent-conjugated antibodies to integrin αvβ3 (LM609, Cheresh Lab), After washing several times with PBS, cells were analyzed by FACS.

Tumorsphere assay. Tumorsphere assay was performed as previously described (10). Cells were treated with vehicle (DMSO), erlotinib (10 nM to 5 µM), lapatinib (10 nM to 5 µM), gemcitabine (0.001 nM to 5 µM), OSI-906 (10 nM to 5 µM), lenalidomide (1 µM), cisplatin (10 nM to 5 µM), or bortezomib (4 nM) diluted in DMSO. The media was replaced with fresh inhibitor 2/6 times a week. Survival curves were generated at least with five concentration points.

Mouse cancer models. All research was conducted under protocol S05018 and approved by the University of California—San Diego Institutional Animal Care and Use Committee (IACUC). FG pancreatic carcinoma cells (1×106 tumor cells in 30 µl of PBS) were injected into the pancreas of 6- to 8-week-old male nude mice as previously described (10). Tumors were established for 2-3 weeks (tumor sizes were monitored by ultrasound) before beginning dosing. Mice were dosed by oral gavage with vehicle (6% Captisol) or 10, 25 and 50 mg/kg/day erlotinib for 10 to 30 days prior to harvest. H441 lung adenocarcinoma cells were generated as previously described (21). 3 weeks after tumor cell injection, the mice were treated with vehicle or erlotinib (100 mg/kg/day) by oral Mouse cancer models. All research was conducted under protocol S05018 and approved by the University of California—San Diego Institutional Animal Care and Use Committee (IACUC). FG pancreatic carcinoma cells (1×106 tumor cells in 30 µl of PBS) were injected into the pancreas of 6- to 8-week-old male nude mice as previously described (10). Tumors were established for 2-3 weeks (tumor sizes were monitored by ultrasound) before beginning dosing. Mice were dosed by oral gavage with vehicle (6% Captisol) or 10, 25 and 50 mg/kg/day erlotinib for 10 to 30 days prior to harvest. H441 lung adenocarcinoma cells were generated as previously described (21). 3 weeks after tumor cell injection, the mice were treated with vehicle or erlotinib (100 mg/kg/day) by oral gavage until moribund (approximately 50 and 58 days, respectively). To generate subcutaneous tumors, FG-β3, FG-R (after erlotinib resistance) and HCC-827 human carcinoma cells (5×106 tumor cells in 200 µl of PBS) were injected subcutaneously to the left or right flank of 6-8-week-old female nude mice. Tumors were measured every 2-3 days with calipers until they were harvested at day 10, 16 or after acquired resistance.

NSCLC specimens from the BATTLE trial. The BATTLE (Biomarker-integrated Approaches of Targeted Therapy for Lung Cancer Elimination) trial was a randomized phase II, single-center, open-label study in patients with advanced NSCLC refractory to prior chemotherapy and included patients with and without prior EGFR inhibitor treatment (12). Patients underwent a tumor new biopsy prior to initiating study treatment. The microarray analysis of mRNA expression on frozen tumor core biopsies was conducted using the Affymetrix Human Gene 1.ST™ platform as previously described (22).

Serial biopsies from NSCLC patients. Tumor biopsies from University of California, San Diego (UCSD) Medical Center stage IV non-small cell lung cancer patients were obtained before erlotinib treatment and 3 patients before and after erlotinib resistance. All biopsies are from lung or pleural effusion. Patients 1 had a core biopsy from the primary lung tumor, and Patient 2 and 3 had a fine needle biopsy from a pleural effusion. All patients had an initial partial response, followed by disease progression after 920, 92, and 120 days of erlotinib therapy, respectively. This work was approved by the UCSD Institutional Review Board (IRB).

Immunofluorescence microscopy. Frozen sections from tumors from orthotopic pancreatic tumors, from patients diagnosed with pancreas cancers (as approved by the institutional Review Board at University of California, San Diego) or tumor cell lines were processed as previously described (23). Cells were stained with indicated primary, followed by secondary antibodies specific for mouse or rabbit (Invitrogen), as appropriate. Samples imaged on a Nikon ECLIPSE C1™ confocal microscope with 1.4 NA 60× oil-immersion lens, using minimum pinhole (30 µm). The following antibodies were used: anti-integrin β3 (LM609), KRAS (Pierce and Abgent M01), Galectin-3, NRAS, RRAS, Genetic knockdown and expression of mutant constructs. Cells were transfected with vector control, WT, G23V RalB-FLAG, WT and S276D NF-κB-FLAG using a lentiviral system. For knock-down experiments, cells were transfected with a pool of RalA, RalB, AKT1, ERK1/2 siRNA (Qiagen) using the lipofectamine reagent (Invitrogen) following manufacturer's protocol or transfected with shRNA (integrin β3, KRAS, Galectin-3, RalB, TBK1 and p65NF-κB) (Open Biosystems) using a lentiviral system. Gene silencing was confirmed by immunoblots analysis.

Immunohistochemical analysis Immunostaining was performed according to the manufacturer's recommendations (Vector Labs) on 5 µM sections of paraffin-embedded tumors from tumor biopsies from lung cancer patients. Tumor sections were processed as previously described (23) using integrin β3 (Abcam clone EP2417Y). Sections stained with integrin β3 were scored by a H-score according to the staining intensity (SI) on a scale 0 to 3 within the whole tissue section.

Immunoprecipitation and immunoblots. Lysates from cell lines and xenograft tumors were generated using standard methods and RIPA or Triton buffers.

Immunoprecipitation experiments were performed as previously described (23) with anti-integrin αvβ3 (LM609) or Galectin-3. For immunoblot analysis, 25 µg of protein was boiled in Laemmli buffer and resolved on 8% to 15% gel. The following antibodies were used: anti-integrin β3, KRAS, NRAS, RRAS, HRAS, Hsp60 and Hsp90 from Santa Cruz, phospho-S172 NAK/TBK1 from Epitomics, TBK1, phospho-p65NF-κB S276, p65NF-κB, RalB, phospho-EGFR, EGFR, from Cell Signaling Technology, and Galectin 3 from BioLegend.

Membrane extract. Membrane fraction from FG and FG-β3 grown in suspension in media complemented with 0.1% BSA were isolated using the MEM-PER membrane extraction kit (Fisher) according to the manufacturer's instructions. Affinity pull-down assays for Ras and Ral. RAS and Ral activation assays were performed in accordance with the manufacturer's (Upstate) instruction. Briefly, cells were cultured in suspension for 3 h. 10 µg of Ral Assay Reagent (Ral BP1, agarose) or RAS assay reagent (Raf-1 RBD, agarose) was added to 500 mg to 1 mg of total cell protein in MLB buffer (Millipore). After 30 min of rocking at 40 C, the activated (GTP) forms of RAS/Ral bound to the agarose beads were collected by centrifugation, washed, boiled in Laemmli buffer, and loaded on a 15% SDS-PAGE gel.

Statistical Analyses. All statistical analyses were performed using Prism software (GRAPHPAD™). Two-tailed Mann Whitney U tests, Chi-squared tests, one way ANOVA tests or t-tests were used to calculate statistical significance. A P value<0.05 was considered to be significant.

Figure Legends

FIG. 1 (FIG. 12/31) illustrates data showing that integrin β3 is expressed in EGFR inhibitor resistant tumors and is necessary and sufficient to drive EGFR inhibitor resistance.

(A) Identification of the most upregulated tumor progression genes common to erlotinib resistant carcinomas. (B) Erlotinib $IC_{50}$ in a panel of human carcinoma cell lines treated with erlotinib in 3D culture. n=3 independent experiments. (C) Percentage of integrin β3 positive cells in parental lines vs. after 3 or 8 weeks treatment with erlotinib. (D) Quantification of integrin β3 (ITGβ3) gene expression in human lung cancer biopsies from patients from the BATTLE Study (18) who were previously treated with an EGFR inhibitor and progressed (n=27), versus patients who were EGFR inhibitor naïve (n=39). (*P=0.04 using a Student's t test). (E) Paired human lung cancer biopsies obtained before and after erlotinib resistance were immunohistochemically stained for integrin β3. Scale bar, 50 (F) Right, effect of integrin β3 knockdown on erlotinib resistance of β3-positive cells. Cells were treated with 0.5 µM of erlotinib. Results are normalized using non-treated cells as controls. n=3; mean±SEM. *P<0.05, **P<0.001. Left, effect of integrin β3 ectopic expression on erlotinib resistance in FG and H441 cells. Cells were treated with 0.5 µM of erlotinib. n=3; mean±SEM. *P<0.05, **P<0.001. (G) Right, effect of integrin β3 knockdown on erlotinib resistance in vivo, A549 shCTRL and A549 sh integrin β3 (n=8 per treatment group) were treated with erlotinib (25 mg/kg/day) or vehicle during 16 days. Results are expressed as average of tumor volume at day 16. *P<0.05. Left, orthotopic FG and FG-β3 tumors (>1000 mm³; n=5 per treatment group) were treated for 30 days with vehicle or erlotinib. Results are expressed as % tumor weight compared to vehicle control. *P<0.05.

FIG. 2 (FIG. 13/31) illustrates data showing that integrin β3 is required to promote KRAS dependency and KRAS-mediated EGFR inhibitor resistance.

(A) Confocal microscopy images show immunostaining for integrin β3 (green), K-, N-, H-, R-Ras (red), and DNA (TOPRO-3, blue) for BxPc3 cells grown in suspension in media with 10% serum. Arrows indicate clusters where integrin β3 and KRAS colocalize (yellow). Scale bar, 10 µm. Data are representative of three independent experiments. Erlotinib $IC_{50}$ in a panel of human carcinoma cell lines expressing non-target shRNA control or KRAS-specific shRNA and treated with erlotinib. n=3 mean±SEM. *P<0.05, **P<0.01. (B-C) Confocal microscopy images show immunostaining for integrin β3 (green), KRas (red) and DNA (Topro-3, blue) for PANC-1 (KRAS mutant) and HCC827 (KRAS wild-type) after acquired resistance to erlotinib (HCC827R) grown in suspension in absence (Vehicle) or in presence of erlotinib (0.5 µM and 0.1 µM respectively). Arrows indicate clusters where integrin β3 and KRAS colocalize (yellow). Scale bar, 10 µm. Data are representative of three independent experiments. (D) Effect of KRAS knockdown on tumorspheres formation in a panel of lung and pancreatic cancer cells expressing or lacking integrin β3. n=3 mean±SEM. *P<0.05, **P<0.01. (E) Effect of KRAS knockdown on tumorsphere formation in PANC-1 (KRAS mutant) stably expressing non-target shRNA control (µ3-positive) or specific-integrin β3 shRNA (β3 negative) in FG (KRAS mutant) and BxPc3 (KRAS wild-type) stably expressing vector control or integrin β3. *n=3; mean+SEM. *P<0.05. **P<0.01. (F) Effect of KRAS knockdown on erlotinib resistance of β3-negative and β3-positive epithelial cancer cell lines. Cells were treated with a dose response of erlotinib. n=3; mean±SEM, *P<0.05, **P<0.01. (G) Confocal microscopy images show immunostaining for integrin β3 (green), KRAS (red) and DNA (TOPRO-3, blue) for PANC-1 cells expressing non-target shRNA control or Galectin 3-specific shRNA grown in suspension. Scale bar=10 µm. Data are representative of three independent experiments. (H) Top: immunoblot analysis of integrin β3 immunoprecipitates from PANC-1 cells expressing non-target shRNA control (CTRL) or Galectin-3-specific shRNA (Gal-3). Bottom: immunoblot analysis of Galectin-3 immunoprecipitates from PANC-1 cells expressing non-target shRNA control (CTRL) or integrin β3-specific shRNA (β3). Data are representative of three independent experiments. (I) Erlotinib dose response of FG-β3 cells expressing a non-target shRNA control or a Galectin-3-specific shRNA (sh Gal-3). n=3; mean±SEM.

FIG. 3 (FIG. 14/31) illustrates data showing that RalB is a central player of integrin β3-mediated EGFR inhibitor resistance.

(A) Effect of RalB knockdown on erlotinib resistance of β3-positive epithelial cancer cell lines. Cells were treated with 0.5 µM of erlotinib. n=3; mean±SEM, *P<0.05, P<0.01. (B) Effect of RalB knockdown on erlotinib resistance of β3-positive human pancreatic (FG-β3) orthotopic tumor xenografts. Established tumors expressing non-target shRNA, (shCTRL) or a shRNA targeting RalB (sh RalB) (>1000 mm³; n=13 per treatment group) were randomized and treated for 10 days with vehicle or erlotinib. Results are expressed as % of tumor weight changes after erlotinib treatment compared to vehicle. P<0.01. (C) Effect of expression of a constitutively active Ral G23V mutant on erlotinib response of β3 negative cells. Cells were treated with 0.5 µM of erlotinib. n=3; mean±SEM. *P<0.05. (D) Effect of expression of integrin β3 on KRAS and RalB membrane localization. Data are representative of two independent experiments. (E) Ral activity was determined in PANC-1 cells grown in suspension by using a GST-RalBP1-RBD immunoprecipitation assay Immunoblots indicate RalB activity and association of active RalB with integrin β3. Data are representative of three independent experiments. (F) Confocal microscopy images of integrin αvβ3 (green), RalB (red) and DNA (TOPRO-3, blue) in tumor biopsies from pancreatic cancer patients. Scale bar, 20 (G) Effect of β3 expression and KRAS expression on RalB activity, measured using a GST-RalBP1-RBD immunoprecipitation assay. Data are representative of three independent experiments. (H) Immunoblot analysis of FG and FG-β3 stably expressing non-target shRNA control or RalB-specific shRNA, grown in suspension and treated with erlotinib (0.5 µM). Data are representative of three independent experiments. (I) Effect of TBK1 and p65 NFκB on erlotinib resistance of FG-β3 cells. Cells were treated with 0.5 µM of erlotinib. n=3; mean±SEM. *P<0.05, **P<0.01.

Figure 15A:
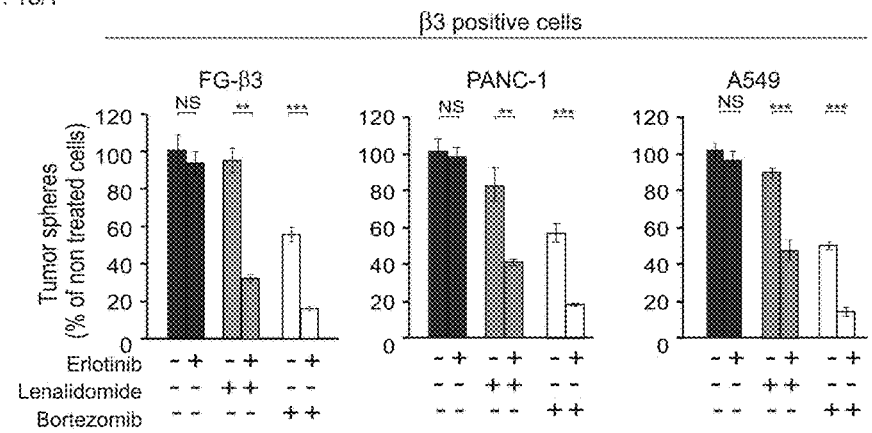
FIG. 15(A) graphically illustrates the effect of NFkB inhibitors on erlotinib response of β3-positive cells (FG-β3, PANC-1 and A549), cells were treated with vehicle, erlotinib (0.5 μM), lenalidomide (1-2 μM), bortezomib (4 nM) alone or in combination.
Figure 15B:
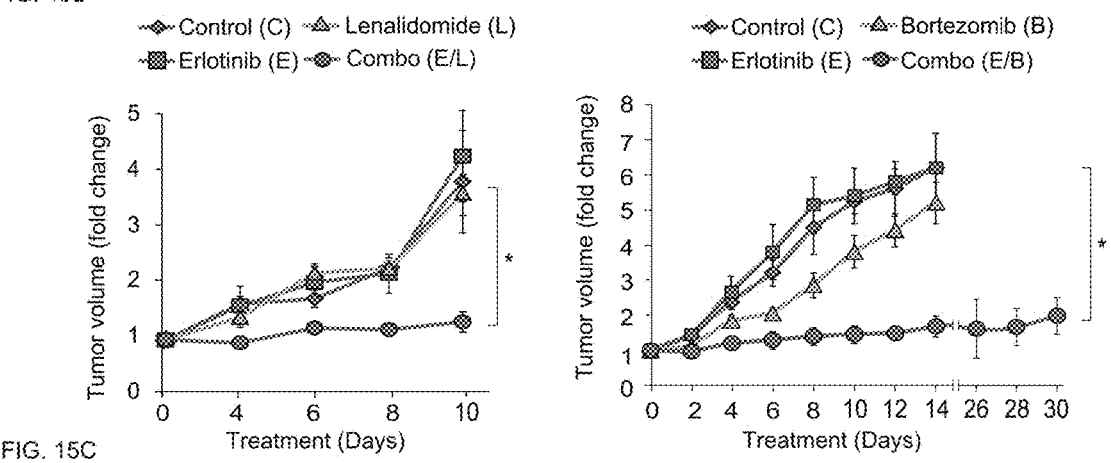
FIG. 15(B) graphically illustrates data from: Left, mice bearing subcutaneous β3-positive tumors (FG-β3) were treated with vehicle, erlotinib (25 mg/kg/day), lenalidomide (25 mg/kg/day) or the combination of erlotinib and lenalidomide, tumor dimensions are reported as the fold change relative to size of the same tumor on Day 1; Right, mice bearing subcutaneous β3-positive tumors (FG-R) after acquired resistance to erlotinib were treated with vehicle, erlotinib (25 mg/kg/day), bortezomib (0.25 mg/kg), the combination of erlotinib and bortezomib, tumor dimensions are reported as the fold change relative to size of the same tumor on Day 1.
Figure 15C:
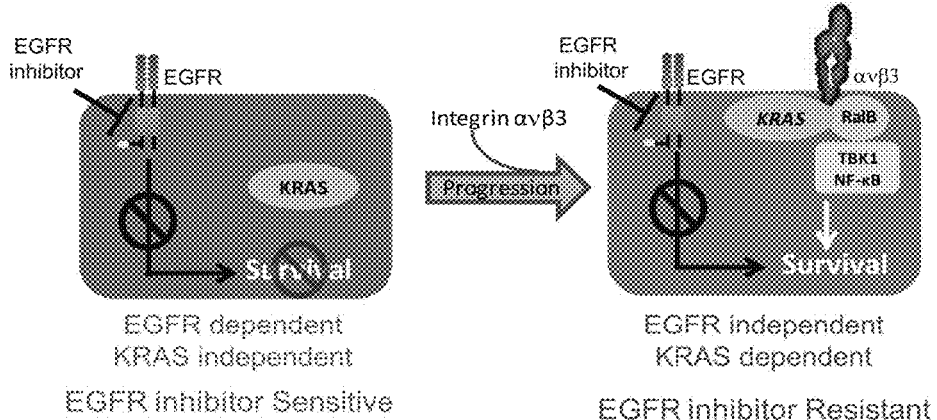
FIG. 15(C) schematically illustrates a model depicting an integrin αvβ3-mediated KRAS dependency and EGFR inhibitor resistance mechanism; as further described in Example 2, below.

FIG. 4 (FIG. 15/31) illustrates data showing that reversal of β3-mediated EGFR inhibitor resistance in oncogenic KRAS model by pharmacological inhibition.

(A) Effect of NFkB inhibitors on erlotinib response of β3-positive cells (FG-β3, PANC-1 and A549). Cells were treated with vehicle, erlotinib (0.5 lenalidomide (1-bortezomib (4 nM) alone or in combination. n=3; mean±SEM. *P<0.05, **P<0.01. (B) Left, mice bearing subcutaneous β3-positive tumors (FG-β3) were treated with vehicle, erlotinib (25 mg/kg/day), lenalidomide (25 mg/kg/day) or the combination of erlotinib and lenalidomide. Tumor dimensions are reported as the fold change relative to size of the same tumor on Day 1. Mean±SEM, (A) *P=0.042 using a one way ANOVA test. n=6 mice per group. Right, mice bearing subcutaneous β3-positive tumors (FG-R) after acquired resistance to erlotinib were treated with vehicle, erlotinib (25 mg/kg/day), bortezomib (0.25 mg/kg), the combination of erlotinib and bortezomib. Tumor dimensions are reported as the fold change relative to size of the same tumor on Day 1. *P=0.0134 using a one way ANOVA test. n=8 mice per group. (C) Model depicting the proposed integrin αvβ3-mediated KRAS dependency and EGFR inhibitor resistance mechanism.

Supplementary FIG. S1 (FIG. 16/31) illustrates resistance to EGFR inhibitor is associated with integrin β3 expression in pancreatic and lung human carcinoma cell lines. (A) Immunoblots showing integrin β3 expression in human cell lines used in FIG. 1A and FIG. 1B. (B) Effect of erlotinib on HCC827 xenograft tumors in immuno—compromised mice (n=5 mice per treatment group) relative to vehicle-treated control tumors. Representative Integrin β3 cell surface quantification in HCC827 treated with vehicle or erlotinib during 64 days. (C) Integrin αvβ3 quantification in orthotopic lung and pancreas tumors treated with vehicle or erlotinib until resistance. For lung cancer, integrin β3 expression was scored (scale 0 to 3) and representative images are shown. For pancreatic cancer, integrin β3 expression was quantified as ratio of integrin αvβ3 pixel area over nuclei pixel area using METAMORPH™ (**P=0.0012, *P=0.049 using Mann-Whitney U test). Representative immunofluorescent staining of integrin αvβ3 in pancreatic human xenografts treated 4 weeks with vehicle or erlotinib.

Figure 17A:
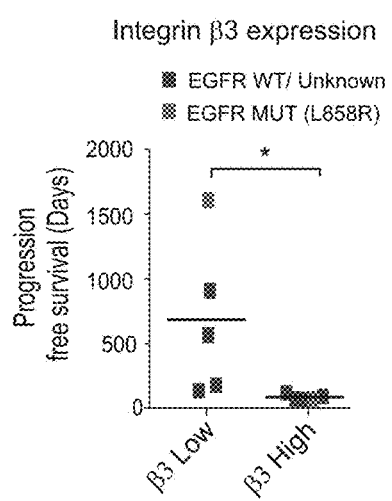
FIG. 17A graphically illustrates a plot of progression-free survival for erlotinib-treated patients with low versus (vs.) high protein expression of β3 integrin measured from non-small cell lung cancer biopsy material (FIG. 17B illustrates: in right panel β3 integrin high cells and left panel β3 integrin low cells) obtained at diagnosis; as further described in Example 2, below.
Figure 17B:
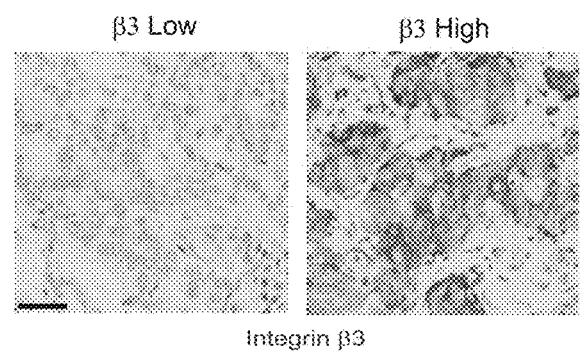
FIG. 17 (or supplementary FIG. S2, in Example 2) illustrates Integrin β3 expression predicts intrinsic resistance to EGFR inhibitors in tumors.
Figure 18A:
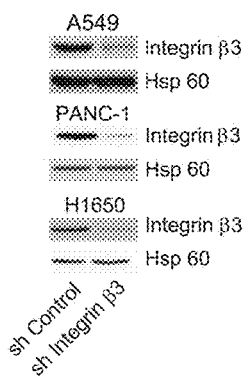
FIG. 18(A) illustrates immunoblots showing integrin β3 knockdown efficiency in cells used in FIG. 12.
Figure 18B:
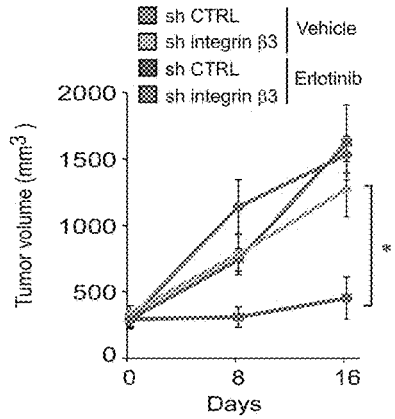
FIG. 18(B) graphically illustrates response of A549 lung carcinoma cells non-target shRNA control or shRNA targeting integrin β3 to treatment with either vehicle or erlotinib (25 mg/kg/day) during 16 days.
Figure 18C:
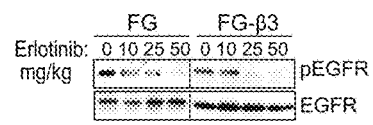
FIG. 18(C) illustrates immunoblots showing expression of indicated proteins of representative tumors.
Figure 18D:
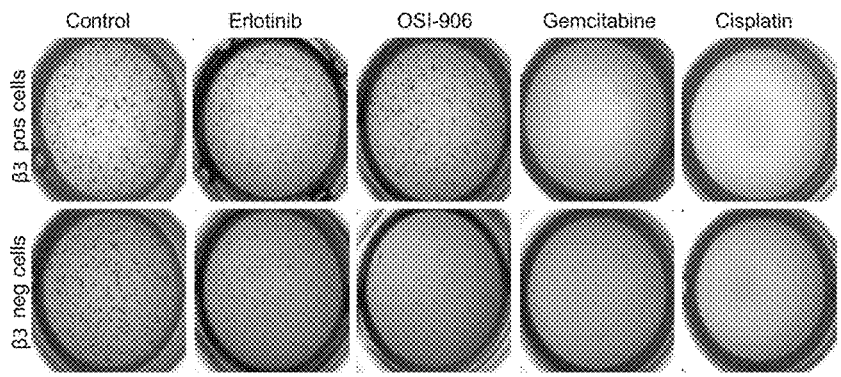
FIG. 18(D) illustrates representative photographs of crystal violet-stained tumorspheres of β3-negative and β3-positive cells after erlotinib, OSI-906, gemcitabine and cisplatin treatment.
Figure 18E:
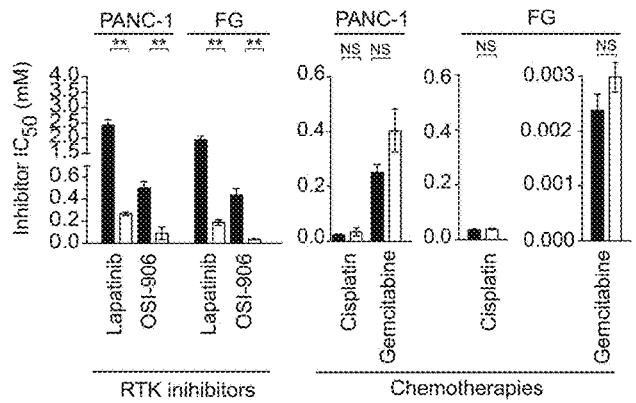
FIG. 18(E) graphically illustrates the effect of integrin β3 expression on lapatinib and OSI-906 (left panel), and cisplatin and gemcitabine (right panel)
Figure 18F:
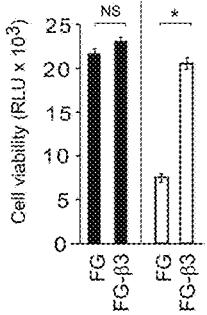
FIG. 18(F) graphically illustrates data from a viability assay of FG and FG-β3 cells grown in suspension in media with or without serum; as further described in Example 2, below.

Supplementary FIG. S2 (FIG. 17/31) illustrates Integrin β3 expression predicts intrinsic resistance to EGFR inhibitors in tumors. Plot of progression-free survival for erlotinib-treated patients with low vs. high protein expression of β3 integrin measured from non-small cell lung cancer biopsy material obtained at diagnosis (*P=0.0122, using Mann-Whitney U test). Representative images showing immunohistochemical staining for β3 integrin (brown) are shown.

Supplementary FIG. S3 (FIG. 18/31) illustrates Integrin β3 confers Receptor Tyrosine Kinase inhibitor resistance.
(A) Immunoblots showing integrin β3 knockdown efficiency in cells used in FIG. 1. (B) Response of A549 lung carcinoma cells non-target shRNA control or shRNA targeting integrin β3 to treatment with either vehicle or erlotinib (25 mg/kg/day) during 16 days. Tumor volumes are expressed as mean±SEM. n=8 mice per group. (C) Immunoblots showing expression of indicated proteins of representative tumors. (D) Representative photographs of crystal violet-stained tumorspheres of β3-negative and β3-positive cells after erlotinib, OSI-906, gemcitabine and cisplatin treatment. (E) Effect of integrin β3 expression on lapatinib, OSI-906, cisplatin and gemcitabine n=3; mean±SEM. (F) Viability assay (CellTiter-Glo assay) of FG and FG-β3 cells grown in suspension in media with or without serum. n=2; mean+SEM. *P<0.05, **P<0.01.

Figures 19A, 19B:
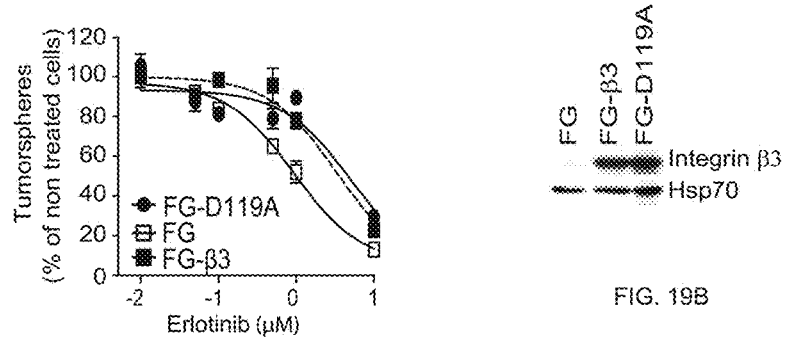
FIG. 19A graphically illustrates the effect of ectopic expression of β3 wild-type (FG-β3) or the β3 D119A (FG-D119A) ligand binding domain mutant on erlotinib response.
FIG. 19B illustrates an immunoblot showing transfection efficiency of vector control, integrin β3 wild-type and integrin β3 D119A; as further described in Example 2, below.

Supplementary FIG. S4 (FIG. 19/31) illustrates Integrin β3-mediated EGFR inhibitor resistance is independent of its ligand binding.

Effect of ectopic expression of β3 wild-type (FG-β3) or the β3 D119A (FG-D119A) ligand binding domain mutant on erlotinib response. n=3; mean±SEM Immunoblot showing transfection efficiency of vector control, integrin β3 wild-type and integrin β3 D119A.

Figure 20A:
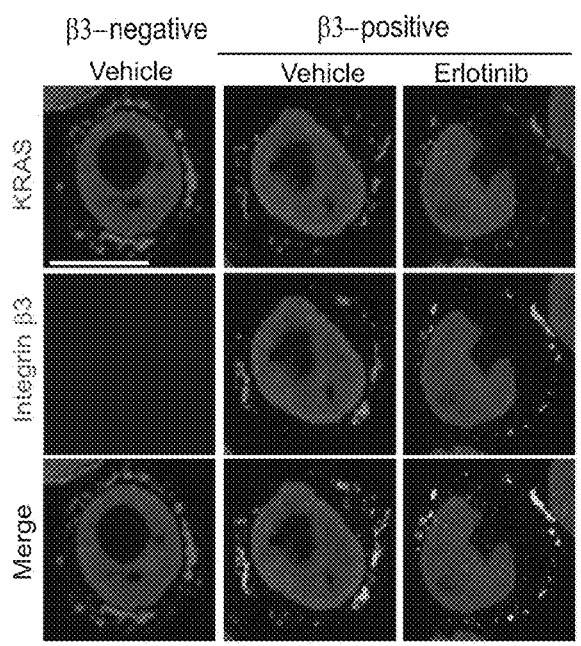
FIG. 20(A) illustrates confocal microscopy images of FG and FG-β3 cells grown in suspension in media 10% serum with or without erlotinib (0.5 μM) and stained for KRAS (red), integrin αvβ3 (green) and DNA (TOPRO-3, blue)
Figure 20B:
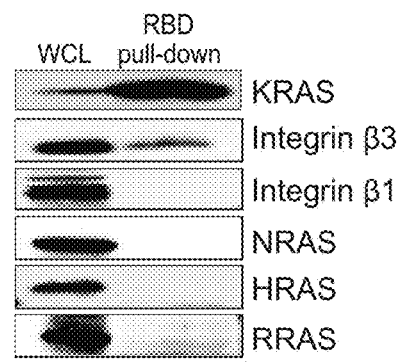
FIG. 20(B) illustrates Ras activity was determined in PANC-1 cells grown in suspension by using a GST-Rafl-RBD immunoprecipitation assay, immunoblots indicate KRAS activity and association of active KRAS with integrin β3.
Figure 20C:
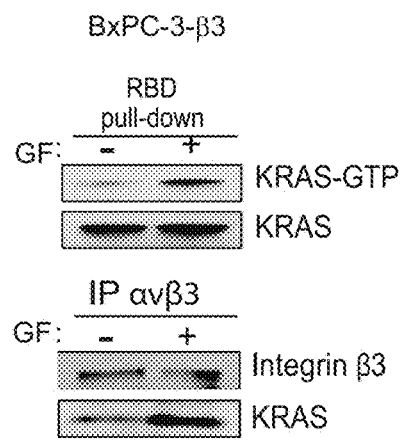
FIG. 20(C) illustrates an immunoblot analysis showing that Integrin αvβ3 immunoprecipitates from BxPC-3 cells grown in suspension in presence or absence of growth factors; as further described in Example 2, below.

Supplementary FIG. S5 (FIG. 20/31) illustrates Integrin β3 colocalizes and interacts with oncogenic and active wild-type KRAS.
(A) Confocal microscopy images of FG and FG-β3 cells grown in suspension in media 10% serum with or without erlotinib (0.5 μM) and stained for KRAS (red), integrin αvβ3 (green) and DNA (TOPRO-3, blue). Scale bar, 10 μm. Data are representative of three independent experiments. (B) Ras activity was determined in PANC-1 cells grown in suspension by using a GST-Rafl-RBD immunoprecipitation assay Immunoblots indicate KRAS activity and association of active KRAS with integrin β3. Data are representative of three independent experiments. (C) Immunoblot analysis of Integrin αvβ3 immunoprecipitates from BxPC-3 cells grown in suspension in presence or absence of growth factors.

Supplementary FIG. S6 (FIG. 21/31) illustrates Integrin β3 expression promotes KRAS dependency.
(A) Immunoblots showing KRAS knockdown efficiency in cells used in FIG. 2. (B) Representative photographs of crystal violet-stained tumorspheres of FG and A549 cells expressing non-target shRNA control or specific-KRAS shRNA. (C) Effect of an additional KRAS knockdown on tumorspheres formation in PANC-1 stably expressing non-target shRNA control (β3-positive) or specific-integrin β3 shRNA (β3 negative). n=3; mean+SEM. *P<0.05. Immunoblots showing KRAS knockdown efficiency.

Figure 22:
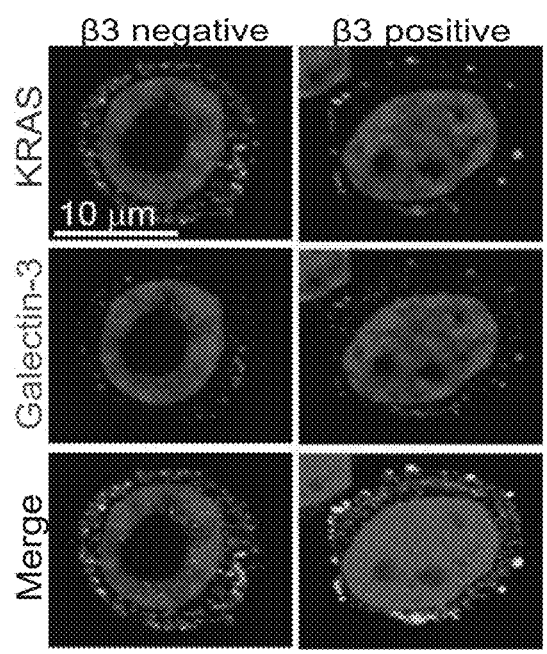
FIG. 22 (or supplementary FIG. S7, in Example 2) illustrates images showing that KRAS and Galectin-3 colocalize in integrin β3-positive cells, in particular, confocal microscopy images of FG and FG-β3 cells grown in suspension and stained for KRAS (green), galectin-3 (red) and DNA (TOPRO-3, blue); as further described in Example 2, below.
Figure 23A:
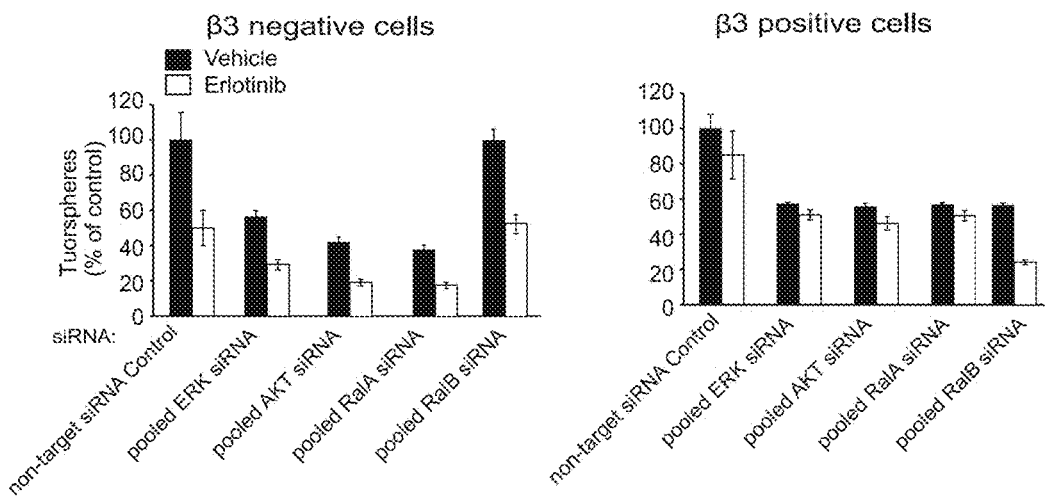
FIG. 23(A) graphically illustrates the effect of ERK, AKT, RalA and RalB knockdown on erlotinib response (erlotinib 0.5 μM) of β3-negative FG (left panel) and β3-positive FG-β3 cells (right panel)
Figure 23B:
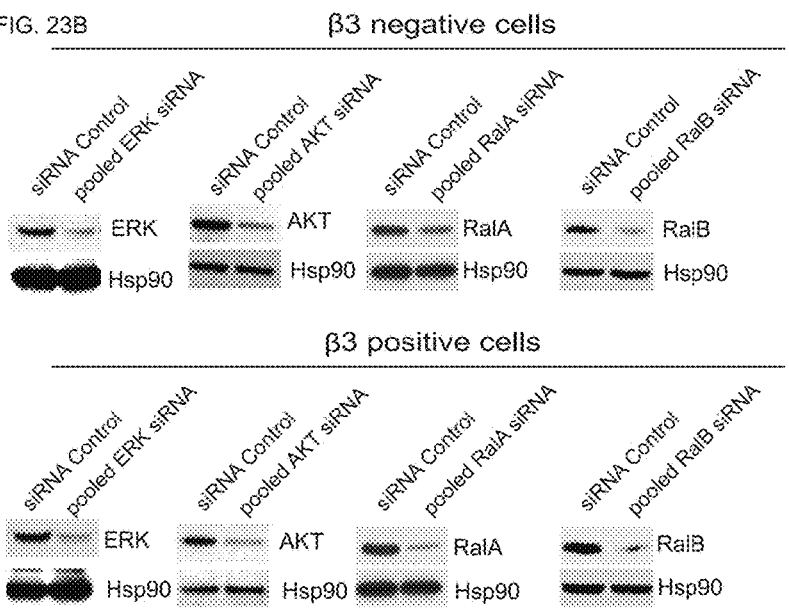
FIG. 23(B) illustrates Immunoblots showing ERK, AKT RalA and RalB knockdown efficiency on β3-negative FG (upper panel) and β3-positive FG-β3 cells (lower panel)
Figure 23C:
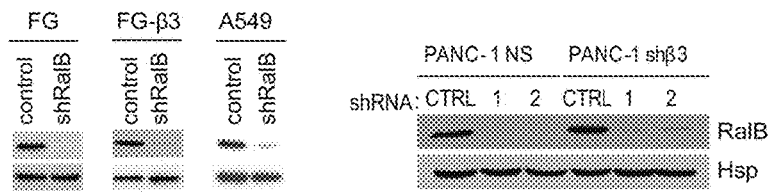
FIG. 23(C) illustrates Immunoblots showing RalB knockdown efficiency in the β3-positive epithelial cancer cells used in FIG. 14; as further described in Example 2, below.

Supplementary FIG. S7 (FIG. 22/31) illustrates KRAS and Galectin-3 colocalize in integrin β3-positive cells.
Confocal microscopy images of FG and FG-β3 cells grown in suspension and stained for KRAS (green), galectin-3 (red) and DNA (TOPRO-3, blue). Scale bar, 10 μm. Data are representative of three independent experiments.
Supplementary FIG. S8 (FIG. 23/31) illustrates Integrin β3-mediated KRAS dependency and erlotinib resistance is independent of ERK, AKT and RalA.
(A) Effect of ERK, AKT, RalA and RalB knockdown on erlotinib response (erlotinib 0.5 μM) of β3-negative FG and β3-positive FG-β3 cells. n=triplicate. (B) Immunoblots showing ERK, AKT RalA and RalB knockdown efficiency. (C) Immunoblots showing RalB knockdown efficiency in cells used in FIG. 3.

Figure 24A:
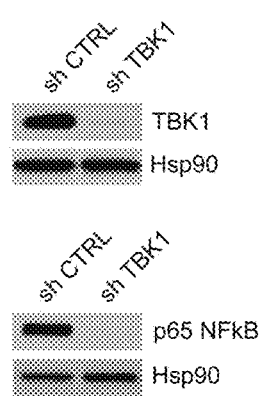
FIG. 24(A) illustrates immunoblots showing a Tank Binding Kinase (TBK1) (upper panel) and NFkB knockdown efficiency (lower panel) used in FIG. 14.
Figure 24B:
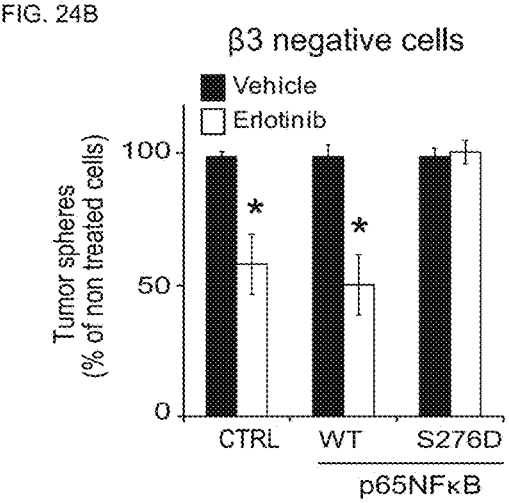
FIG. 24(B) graphically illustrates the effect of constitutive active S276D p65NFkB on erlotinib response (erlotinib 0.5 OA) of β3-negative cells (FG cells); as further described in Example 2, below.
Figure 25A:
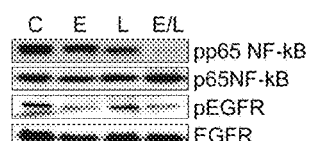
Figure 25B:
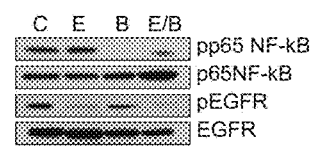
Figure 25C:
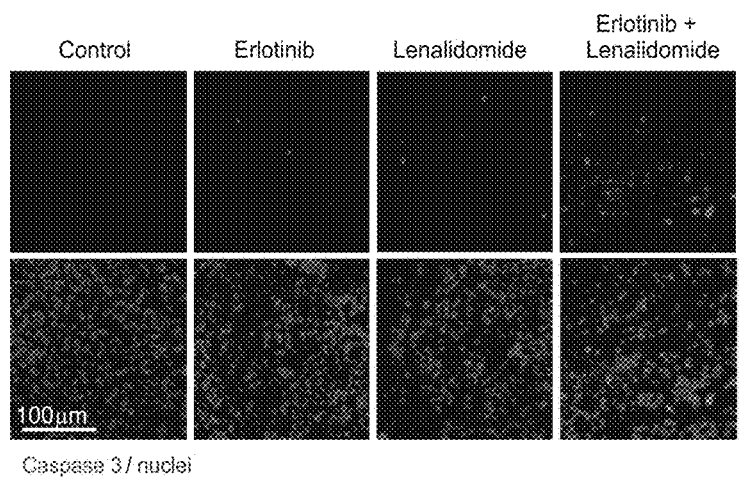
FIG. 25(C) illustrates Confocal microscopy images of cleaved caspase 3 (red) and DNA (TOPRO-3, blue) in tumor biopsies from xenografts tumors used in FIG. 15B treated with vehicle, erlotinib, lenalidomide or lenalidomide and erlotinib in combo.
Figure 25D:
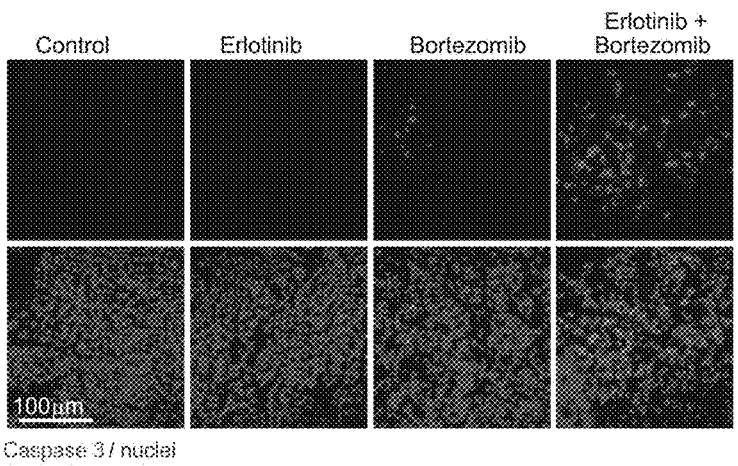
FIG. 25(D) illustrates Confocal microscopy images of cleaved caspase 3 (red) and DNA (TOPRO-3, blue) in tumor biopsies from xenografts tumors used in FIG. 15B treated with vehicle, erlotinib, bortezomib or bortezomib and erlotinib in combo); as further described in Example 2, below.
Figure 30A:
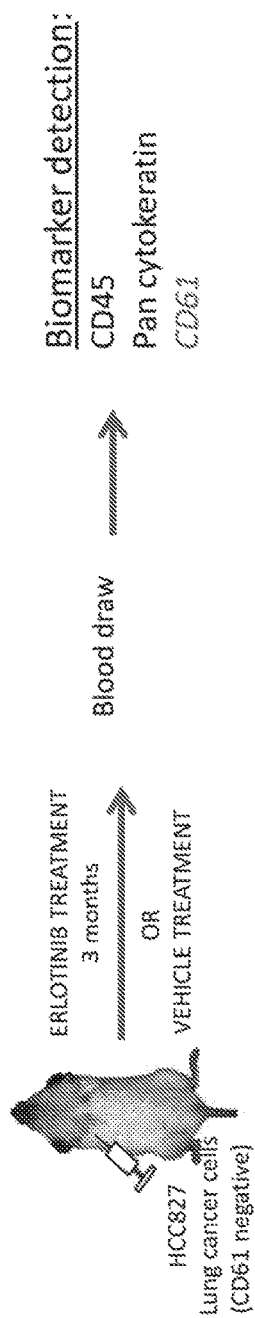
FIG. 30 illustrates data showing integrin β3 (CD61) is a RTKI (Receptor Tyrosine Kinase (RTK) Inhibitor) drug resistance biomarker on the surface of circulating tumor cells; as discussed in detail in Example 2, below. As schematically illustrated in FIG. 30A, CD61 (β3, or beta3) negative human lung cancer cells (HCC827; this lung adenocarcinoma has an acquired mutation in the EGFR tyrosine kinase domain (E746-A750 deletion), and they are sensitive to erlotinib and develop acquired resistance after 6/8 weeks) were injected orthotopically into the lung of mice and treated over 3 months with erotinib at 25 mg/kg/day. As graphically illustrated in FIG. 30B, Human lung cancer cells detected in the circulation were positive for αvβ3 (or avb3, CD61) whereas the cells in the untreated group were essentially negative for this marker. CD45 negative cells indicates that the detected cells were not leukocytes and pan cytokeratin positive cells indicate tumor cells. CD61 (beta3) positive expression correlated with tumor expression.
Figure 30B:
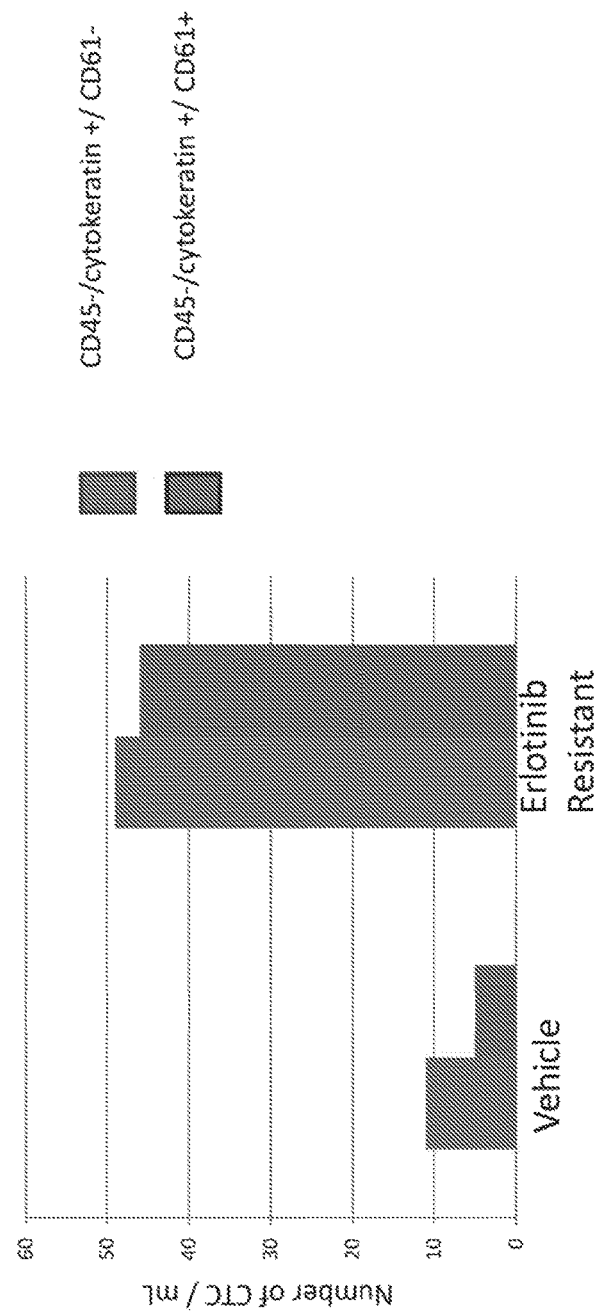

Supplementary FIG. S9 (FIG. 24/31) illustrates Constitutive active NFkB is sufficient to promote erlotinib resistance.
(A) Immunoblots showing TBK1 and NFkB knockdown efficiency used in FIG. 3. (B) Effect of constitutive active S276D p65NFkB on erlotinib response (erlotinib 0.5 μM) of β3-negative cells (FG cells). n=3; mean±SEM. *P<0.05.

Supplementary FIG. S10 (FIG. 25/31) illustrates NFkB inhibitors in combination with erlotinib increase cell death in vivo.
(A-B) Immunoblots showing expression of indicated proteins of representative tumors from shown in FIG. 4B (C) Confocal microscopy images of cleaved caspase 3 (red) and DNA (TOPRO-3, blue) in tumor biopsies from xenografts tumors used in FIG. 4B treated with vehicle, erlotinib, lenalidomide or lenalidomide and erlotinib in combo. Scale bar, 20 μm. (D) Confocal microscopy images of cleaved caspase 3 (red) and DNA (TOPRO-3, blue) in tumor biopsies from xenografts tumors used in FIG. 4B treated with vehicle, erlotinib, bortezomib or bortezomib and erlotinib in combo.

Supplementary Table 1: shows differentially expressed genes in cells resistant to erlotinib (PANC-1, H1650, A459) compared with the average of two sensitive cells (FG, H441) and in HCC827 after acquired resistance in vivo (HCC827R) vs. the HCC827 vehicle-treated control. The genes upregulated more than 2.5 fold are in red.

Supplementary Table 2: shows KRAS mutational status of the pancreatic and lung cancer cell lines used in this study.

References—Example 2
1. R. J. Gillies, D. Verduzco, R. A. Gatenby, Evolutionary dynamics of carcinogenesis and why targeted therapy does not work. *Nature reviews. Cancer* 12, 487 (July, 2012).
2. S. Zhang et al., Combating trastuzumab resistance by targeting SRC, a common node downstream of multiple resistance pathways. *Nature medicine* 17, 461 (April, 2011).
3. J. S. Duncan et al., Dynamic reprogramming of the kinome in response to targeted MEK inhibition in triple-negative breast cancer. *Cell* 149, 307 (Apr. 13, 2012).
4. D. L. Wheeler, E. F. Dunn, P. M. Harari, Understanding resistance to EGFR inhibitors-impact on future treatment strategies. *Nature reviews* 7, 493 (September, 2010).
5. F. Ciardiello, G. Tortora, EGFR antagonists in cancer treatment. *The New England journal of medicine* 358, 1160 (Mar. 13, 2008).
6. C. M. Ardito et al., EGF receptor is required for KRAS-induced pancreatic tumorigenesis. *Cancer Cell* 22, 304 (Sep. 11, 2012).
7. C. Navas et al., EGF receptor signaling is essential for k-ras oncogene-driven pancreatic ductal adenocarcinoma. *Cancer Cell* 22, 318 (Sep. 11, 2012).
8. C. Ferte et al., Durable responses to Erlotinib despite KRAS mutations in two patients with metastatic lung adenocarcinoma. *Ann Oncol* 21, 1385 (June, 2010).
9. M. J. Moore et al., Erlotinib plus gemcitabine compared with gemcitabine alone in patients with advanced pancreatic cancer: a phase III trial of the National Cancer Institute of Canada Clinical Trials Group. *J Clin Oncol* 25, 1960 (May 20, 2007).
10. E. S. Kim et al., The BATTLE Trial: Personalizing Therapy for Lung Cancer. *Cancer discovery* 1, 44 (June, 2012).
11. J. S. Desgrosellier et al., An integrin alpha(v)beta(3)-c-Src oncogenic unit promotes anchorage-independence and tumor progression. *Nature medicine* 15, 1163 (October, 2009).
12. A. U. Newlaczyl, L. G. Yu, Galectin-3—a jack-of-all-trades in cancer. *Cancer letters* 313, 123 (Dec. 27, 2011).
13. A. I. Markowska, F. T. Liu, N. Panjwani, Galectin-3 is an important mediator of VEGF- and bFGF-mediated angiogenic response. *The Journal of experimental medicine* 207, 1981 (Aug. 30, 2010).
14. D. A. Barbie et al., Systematic RNA interference reveals that oncogenic KRAS-driven cancers require TBK1. *Nature* 462, 108 (Nov. 5, 2009).
15. Y. Chien et al., RalB GTPase-mediated activation of the IkappaB family kinase TBK1 couples innate immune signaling to tumor cell survival. *Cell* 127, 157 (Oct. 6, 2006).
16. Y. Yang et al., Exploiting Synthetic Lethality for the Therapy of ABC Diffuse Large B Cell Lymphoma. *Cancer Cell* 21, 723 (Jun. 12, 2012).
17. M. S. Kumar et al., The GATA2 transcriptional network is requisite for RAS oncogene-driven non-small cell lung cancer. *Cell* 149, 642 (Apr. 27, 2012).
18. E. S. Kim et al., The BATTLE Trial: Personalizing Therapy for Lung Cancer. *Cancer discovery*, (Apr. 3, 2011, 2011).

Example 3

A β3 Integrin/KRAS Complex Shift Tumor Phenotype Toward Stemness

The data presented herein demonstrates the effectiveness of the compositions and methods of the invention in reversing tumor initiation and self-renewal, and resensitizing tumors to Receptor Tyrosine Kinase (RTK) inhibition.

Integrin αvβ3 expression is a marker of tumor progression for a wide range of histologically distinct cancers[1], yet the molecular mechanism by which αvβ3 influences the growth and malignancy of cancer is poorly understood. Here, we reveal that integrin αvβ3, in the unligated state, is both necessary and sufficient to promote tumor initiation and self-renewal through its recruitment of KRAS/RalB to the plasma membrane leading to the activation of TBK-1/NFkB. Accordingly, this pathway also drives KRAS-mediated resistance to receptor tyrosine kinases inhibitors such as erlotinib Inhibition of RalB or its effectors not only reverses tumor initiation and self renewal but resensitizes tumors to Receptor Tyrosine Kinase (RTK) inhibition. These findings provide a molecular basis to explain how αvβ3 drives tumor progression and reveals a therapeutic strategy to target and destroy these cells.

Tumor-initiating cells (also known as cancer stem cells), EMT, and drug resistance have recently been linked together as a challenge for cancer therapy[2]. Here, we propose integrin αvβ3 as a potential lynchpin capable of influencing and integrating these three critical determinants of cancer progression. Indeed, expression of β3 integrin has long been associated with poor outcome and higher incidence of metastasis for a variety of epithelial cancers[1], its expression has been reported on a subpopulation of breast[3,4] and myeloid leukemia cancer stem cells, and β3 has been implicated in the process of epithelial-to-mesenchymal transition, especially in the context of TGF-β[5,6]. Although the primary influence of integrins is considered to be their regulation of cell-matrix adhesion events leading to clustering of focal adhesions to drive intracellular signaling cascades, we have recently made the surprising observation that αvβ3 integrin is capable of forming clusters on the surface of non-adherent cells to recruit signaling complexes that can drive cell survival in the absence of ligand binding[7]. This property is not shared by other integrins, including β1, suggesting that αvβ3 expression may provide a critical survival signal for cells invading hostile environments. Indeed, exposing quiescent endothelial cells to angiogenic growth factors results in the upregulation of αvβ3 expression that is required for their conversion to the angiogenic/invasive state[8]. We propose that expression of αvβ3 offers tumor cells an equivalent survival advantage, and that targeting this pathway could undercut a tumors ability to metastasize and resist therapy.

Since we previously reported that integrin αvβ3 expression was associated with increased anchorage-independent growth[7], we postulated that β3 expression may play a role in tumor progression by shifting epithelial tumor cells toward a stem-like phenotype. To evaluate a possible effect of β3 expression on tumor stemness in vivo, we knocked down integrin β3 in various human carcinoma cells expressing this receptor, or ectopically expressed β3 in tumor cells lacking this integrin. Compared with their respective β3-negative counterparts, β3-positive cells showed a 50-fold increased tumor-initiating capacity, measured as a higher frequency of tumor initiating cells in a limiting dilution assay (see FIG. 1a and FIG. S1a-c (of Example 3), which are FIG. 32a and FIGS. 36a, 36b and 36c, respectfully).

In vitro, tumor stemness is also associated with an increased capacity to form tumorspheres and undergo self-renewal. Consequently, we measured the capacity of β3 expressing tumor cells to form primary and secondary tumorspheres. Notably, the ratio of secondary tumorspheres to primary tumorspheres was 2-4 fold higher for cells expressing integrin β3 (see FIG. 1b-d and FIG. S1c (of Example 3); which are FIG. 32b-d and FIG. 36c, respectively). Together, these findings indicate that β3 expression enhances the stem-like behavior of these tumors.

Figure 33A:
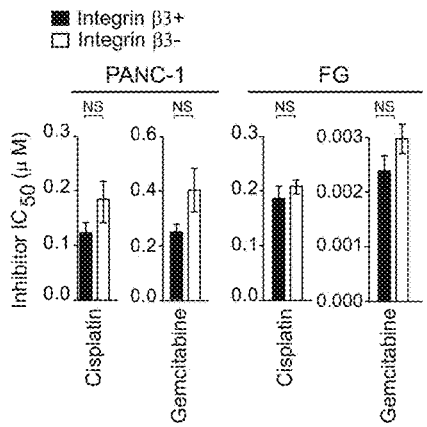
FIG. 33(a) graphically illustrates the Effect of integrin β3 expression (ectopic expression for FG and integrin β3-specific knockdown for PANC-1) cells on drug treatment response.
Figure 33B:
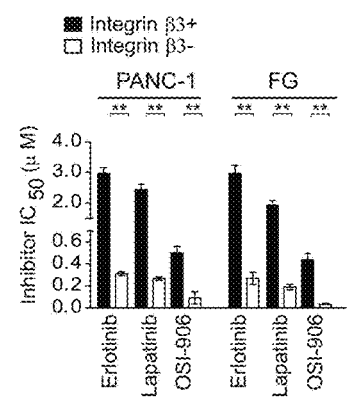
FIG. 33(b) graphically illustrates the Effect of integrin β3 knockdown on erlotinib response in MDA-MB-231 (MDA231), A549 and H1650.
Figure 33C:
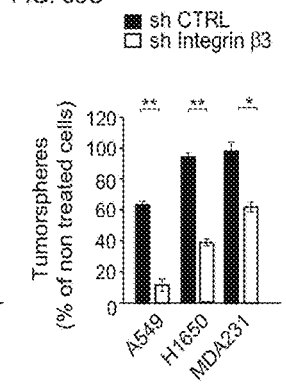
FIGS. 33(c) and 33(d) graphically illustrate the effect of integrin β3 knockdown on erlotinib resistance in vivo using A549 shCTRL and A549 sh β3 treated with erlotinib or vehicle, FIG. 33(c) measuring tumorspheres, and β3(d) measuring tumor volume in A549 shCTRL (integrin β3+), left panel, and A549 (integrin β3−) (right panel)

Tumor-initiating cells are known to be particularly resistant to cellular stresses, such as nutrient deprivation or exposure to anti-cancer drugs[9]. Indeed, β3-positive cells survived to a greater degree when stressed by removal of serum from their growth media compared with cells lacking this integrin (FIG. S1d (of Example 3), or FIG. 36d). However, β3 expression did not impact the response to the chemotherapeutic agent cisplatin or the anti-metabolite agent gemcitabine for cells growing in 3D (FIG. 2a, or FIG. 33a). Under these same conditions, β3 expression did strongly correlate with reduced sensitivity to Receptor Tyrosine Kinase (RTK) inhibitors, including the EGFR1 inhibitor erlotinib, the EGFR1/EGFR2 inhibitor lapatinib, and the IGF-1R inhibitor linsitinib (OSI906) (FIG. 2b-c, or FIG. 33b-c).

Figure 33D:
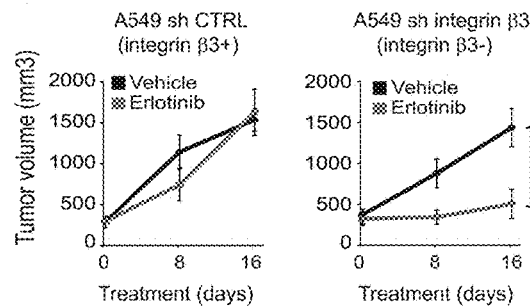
Figure 33E:
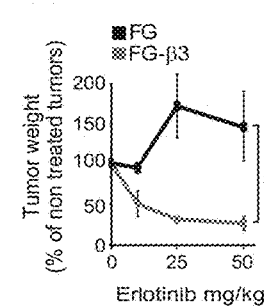
FIG. 33(e) [[33(d)]] graphically illustrates Orthotopic FG and FG-β3 tumors (>1000 mm$^3$; n=5 per treatment group) were treated for 30 days with vehicle or erlotinib.

This link between β3 expression and RTK inhibitor resistance was also observed in vivo, as knockdown of integrin β3 overcame erlotinib resistance for subcutaneous A549 xenografts (FIG. 2d, or FIG. 33d), while ectopic expression of integrin β3 conferred erlotinib resistance to FG tumors growing orthotopically in the pancreas (FIG. 2e, or FIG. 33e).

Figure 33G:
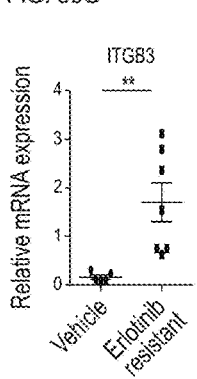
FIG. 33(g) H&E sections and immunohistochemical analysis of integrin β3 expression in paired human lung cancer biopsies obtained before and after erlotinib resistance.

In clinic, human non-small cell lung cancer harboring activating mutations in EGFR often initially respond to erlotinib but invariably develop resistance through multiple mechanisms including acquired or selected mutations, gene amplification and alternate routes of kinase pathway activation. Recent studies indicate that multiple resistance mechanisms may operate within an individual tumor to promote acquired resistance to EGFR TKIs in persons with NSCLC and accumulating evidence supports the concept that the tumor-initiating cells contribute to EGFR TKI resistance in lung. To assess the clinical relevance of our findings, mice with established HCC827 (human NSCLC cells with deletion of exon 19 of EGFR) have been treated with erlotinib until development of acquired resistance (FIG. 2f, or FIG. 33f). Integrin β3 expression was significantly higher in erlotinib resistant tumors compared to vehicle-treated tumors (FIG. 2g, or FIG. 33g).

Figure 33I:
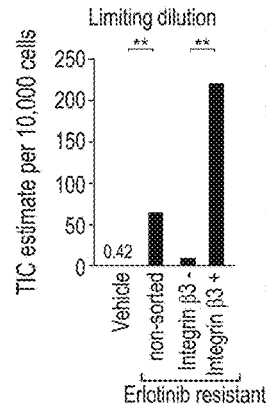
FIG. 33(i) and FIG. 33(j) graphically illustrate the Self-renewal capacity of HCC827 vehicle-treated (vehicle), erlotinib-treated (erlotinib resistant non-sorted), erlotinib-treated integrin β3-population and erlotinib-treated integrin β3+ population; as described in detail in Example 3, below.
Figure 33J:
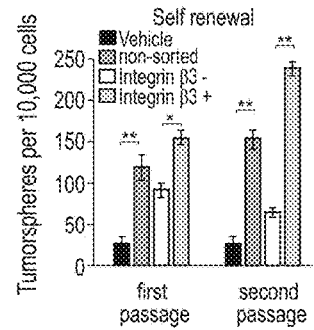

To validate these findings, we examined biopsies from lung cancer patients harboring an EGFR mutation before erlotinib treatment and after acquired resistance and we found that integrin β3 expression was qualitatively higher after acquired resistance to erlotinib (FIG. 2h, or FIG. 33h; FIG. S1e, or, or FIG. 36e). To investigate the role of integrin β3 in this context, we sorted erlotinib-resistant HCC827 tumors into integrin β3$^+$ and Integrin β3$^-$ populations and tested them for tumor initiating cell abilities. As expected, the integrin β3$^+$ population showed enhanced tumor initiating and self-renewal capacities compared to the integrin β3$^-$ population (FIG. 2i j, or FIG. 33i-j; FIG. S1f, or FIG. 36f) suggesting that integrin β3 contribute to the stem-like phenotype of the drug resistance tumor. In addition integrin β3 has been found in a subpopulation of the CD166+ cells in human adenocarcinoma after acquired resistance to erlotinib (FIG. S1g, or FIG. 36g). Together these findings reveal that β3 expression is both necessary and sufficient to account for tumor stem-like properties in vitro and in vivo.

Figure 37A:
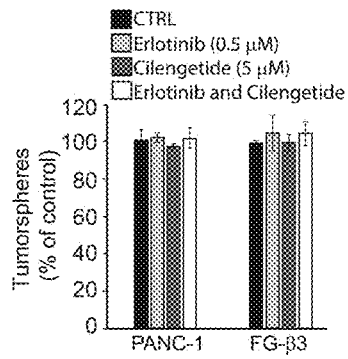
FIG. 37(a) Effect of cilengetide treatment on erlotinib resistance in FG-β3 and PANC-1 cells.
Figure 37B:
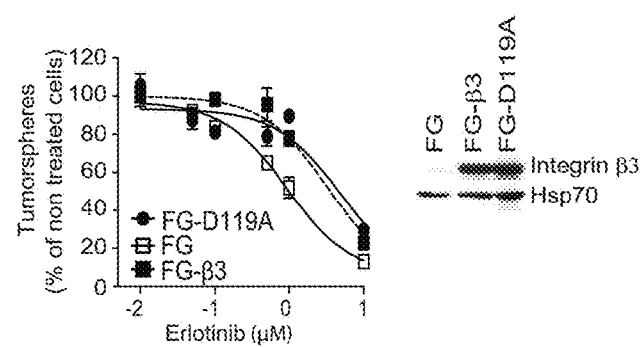
FIG. 37(b) Effect of ectopic expression of β3 wild-type (FG-β3) or the β3 D119A (FG-D119A) ligand binding domain mutant on erlotinib response.

Our results suggest that targeting integrin β3 function may represent a viable approach to reverse stem-like properties and sensitize tumors to RTK inhibitors. However, integrin antagonists that compete for ligand binding sites and disrupt cell adhesion are not likely to have an impact on the stemness and drug resistance properties that are represented by 3D growth of tumor cells under anchorage-independent conditions. Accordingly, neither expression of a mutant integrin β3 (D119A) incapable of binding ligand nor treating cells with cyclic peptides that compete with αvβ3 for ligand binding impacted the β3-mediated enhancement of 3D colony formation in the presence of erlotinib (FIG. S2a-b, or FIG. 37a-b). Thus, the contribution of β3 integrin to stemness and drug resistance appears to involve a non-canonical function for this integrin, independent from its traditional role as a mediator of cell adhesion to specific β3 ligands. If this is the case, then blocking this pathway will require understanding the downstream molecular mechanism(s) that become engaged in the presence of β3.

Figure 37C:
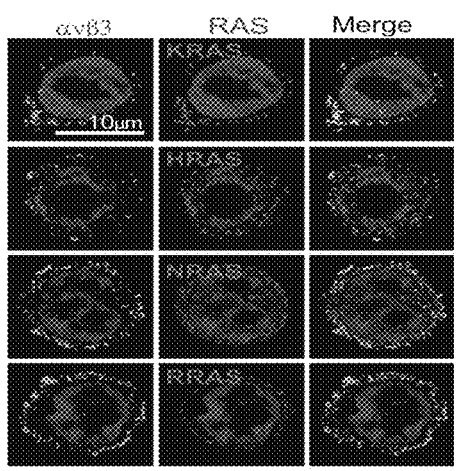
FIG. 37(c) Confocal microscopy images of FG-β3 cells grown in 3D and stained for integrin—β3 (green) and RAS family members (red)
Figure 37D:
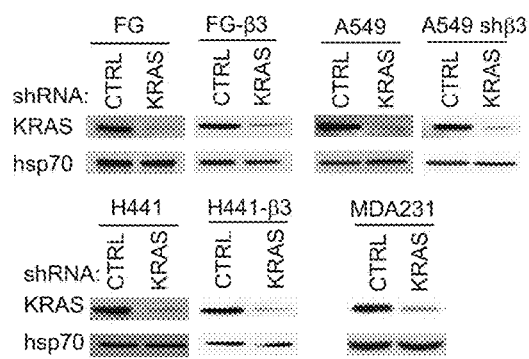
FIG. 37(d) Immunoblots showing KRAS knockdown efficiency in cells used in FIG. 3 (of Example 3)
Figure 37E:
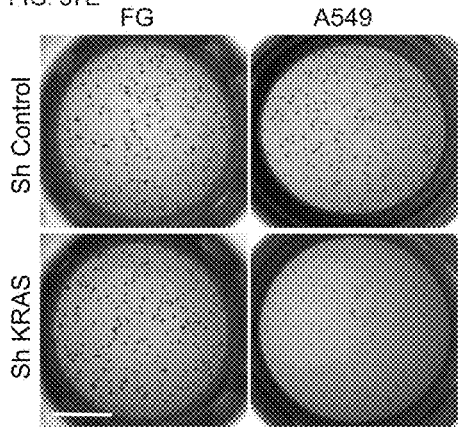
FIG. 37(e) Representative photographs of crystal violet-stained tumorspheres of FG and A549 cells expressing non-target shRNA control or specific-KRAS.
Figure 37F:
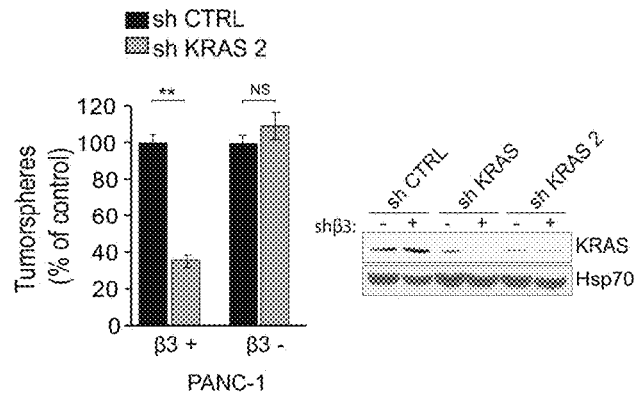
FIG. 37(f) illustrates the Effect of a second KRAS knockdown (shKRAS 2) on tumorspheres formation in PANC-1 stably expressing non-target shRNA control (3-positive) or specific-integrin-β3 shRNA (3 negative), left panel graphically presenting data and right panel illustrating an immunoblot showing KRAS expression in sh CTRL, SH KRAS and sh KRAS 2; as described in detail in Example 3, below.
Figure 39A:
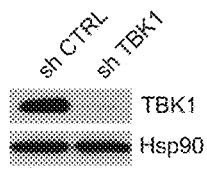
FIG. 39(a) Immunoblot showing TBK1 knockdown efficiency in PANC-1 cells used in FIG. 4 (of Example 3)
Figure 39B:
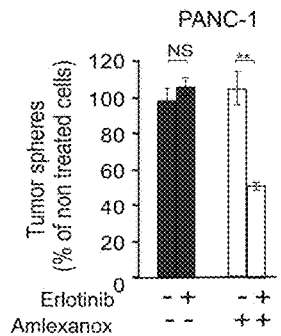
FIG. 39(b) Effect of the TBK1 inhibitor amlexanox on erlotinib response of PANC-1 cells.
Figure 39C:
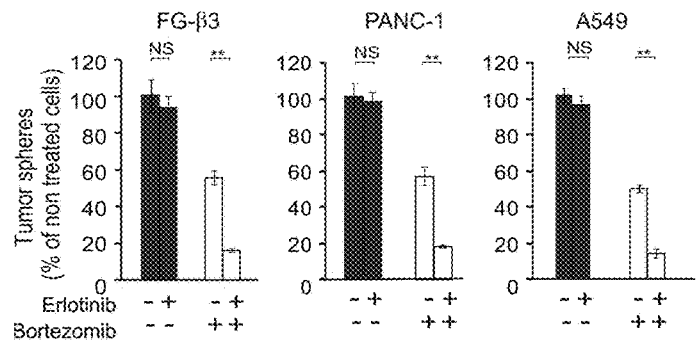
FIG. 39(c) Effect of the NFkB inhibitor borthezomib on β3-positive cells (FG-β3 (left panel), PANC-1 (middle panel) and A549 (right panel))
Figure 39D:
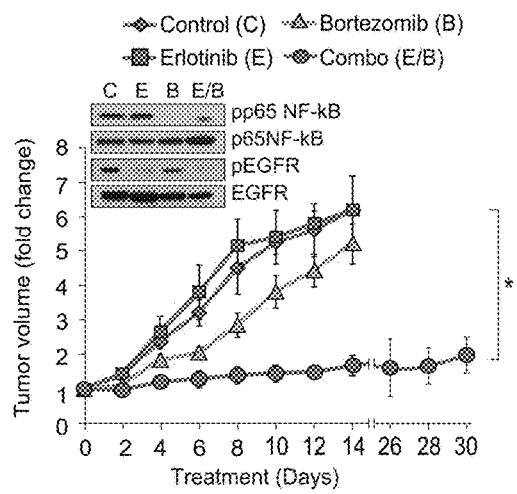
FIG. 39(d) Mice bearing subcutaneous β3-positive tumors (FG-β3) were treated with vehicle, erlotinib (25 mg/kg/day), bortezomib (0.25 mg/kg), the combination of erlotinib and bortezomib.
Figure 39E:
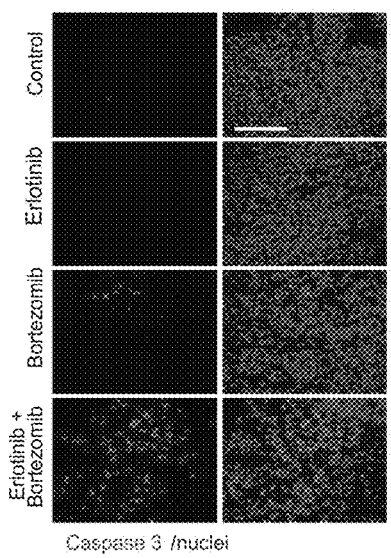
FIG. 39(e) Confocal microscopy images of cleaved caspase 3 (red) and DNA (TOPRO-3, blue) in tumor biopsies from xenografts tumors used in (d) treated with vehicle, erlotinib, bortezomib or bortezomib and erlotinib in combo; as described in detail in Example 3, below.

To study how β3 integrin influences tumor stemness, we considered that integrins frequently transmit signals in the context of RAS family members[10]. To examine a possible link between β3 expression and RAS, tumor cells growing in 3D were stained for β3 and various RAS family members. Interestingly, in cells growing in suspension, β3 co-localized in clusters at the plasma membrane with KRAS, but not with NRAS, RRAS, or HRAS (FIG. 3a, or FIG. 34a, FIG. S2c, or FIG. 37c). In fact, KRAS could be specifically co-immunoprecipitated with β3 but not 31 integrin (FIG. 3b, or FIG. 34b), indicating a specific interaction between β3 and KRAS in cells undergoing anchorage-independent growth. Finally, we observed that KRAS knockdown abolished the β3-induced anchorage independence, self-renewal, and erlotinib resistance (FIG. 3c-e, or FIG. 34c-e), indicating that β3 and KRAS cooperate to drive β3-mediated stem-like phenotype.

Since there are no known KRAS binding sites on the β3 cytoplasmic tail, it is likely that this KRAS/β3 interaction occurs through an intermediary. Galectin-3 is a carbohydrate-binding lectin linked to tumor progression[11] that is known to separately interact with KRAS[12] and integrin αvβ3[13]. Therefore, we considered whether Galectin-3 might serve as an adaptor facilitating the β3/KRAS interaction in anchorage-independent tumor cells. Indeed, we observed co-localization of β3, KRAS, and Galectin-3 within membrane clusters for cells grown under anchorage-independent conditions (FIG. 3f, or FIG. 34f). Knockdown of Galectin-3 not only prevented formation of the KRAS/β3 complex (FIG. 3f-g, or FIG. 34f-g), but also reversed the advantage of β3 expression for anchorage independence erlotinib resistance and self-renewal (FIG. 3h-i, or FIG. 34h-i). These findings provide evidence that Galectin-3 facilitates an interaction between β3 and KRAS that is required for the promotion of stemness.

The activation of KRAS elicits changes in cellular function by signaling through a number of downstream effectors, most prominently AKT/PI3K, RAF/MEK/ERK, and Ral GTPases[14]. Depletion of Akt, Erk, or RalA inhibited the 3D growth of β3⁺ versus β3⁻ tumor cells equally (FIG. S3a-b, or FIG. 38a-b), suggesting these effectors were not selectively involved in the ability of β3 to enhance stemness. In contrast, knockdown of RalB not only selectively impaired colony formation for β3⁺ cells (FIG. 4a, or FIG. 35a; FIG. S3c-d), but it also negated the effect of β3 expression and stem-like phenotype (FIG. 4b-c; FIG. S3e, or FIG. 38e) and erlotinib resistance (FIG. 4d-e, or FIG. 35d-e). Mechanistically, the association between KRAS and integrin β3 at the plasma membrane was able to recruit and activate RalB (Supplementary Information, FIG. S3f-h, or FIG. 38f-h). In fact, the activation of RalB alone is sufficient to drive this pathway, since expression of a constitutively active RalB G23V mutant in β3-negative tumor cells conferred erlotinib resistance (FIG. S3i, or FIG. 38i).

Consistent with recent studies that have linked the RalB effectors TBK1 and RelA to RTKI resistance and stemness[15], β3⁺ tumor cells showed activation of these effectors even in the presence of erlotinib (FIG. 4f, or FIG. 35f). Loss of RalB restored erlotinib-mediated inhibition of TBK1 and RelA for β3⁺ tumor cells (FIG. 4f, or FIG. 35f), suggesting these as therapeutic targets relevant for this pathway. Since targeting integrin ligation events cannot perturb this pathway, and RAS inhibitors have underperformed expectations in the clinic, interrupting signaling downstream of RalB could reverse the stemness potential of β3⁺ tumor cells. Indeed, genetic or pharmacological inhibition of TBK1 or RelA overcame self-renewal and β3-mediated erlotinib resistance (FIG. 4g-i, or FIG. 35g-i; FIG. S4a-e, or FIG. 39a-e). Taken together, our observations indicate that integrin β3 expression promotes a cancer stem-like program by cooperating with KRAS to regulate the activity of RalB, and that elements of this pathway can be disrupted to provide therapeutic benefit in mouse models of lung and pancreatic cancer.

Despite numerous advances in our knowledge of cancer, most advanced cancers remain incurable. At present, conventional therapies can control tumor growth initially but most patients ultimately relapse, highlighting the urgent need for new approaches to treat cancerous tumors. One such approach may be to target the tumor-initiating cells. An emerging picture is that tumor-initiating cells do not constitute a homogenous population of cells explaining the lack of reliability of cancer stem markers. We discovered an integrin β3+ subpopulation of tumor-initiating cells that are specifically resistant to RTKIs. Several studies have shown that integrin-mediated cellular adhesion to extracellular matrix components is an important determinant of therapeutic response. In fact, integrin β3 increases adhesion-mediated cell survival, drug resistance and suppresses antitumor immunity[16] suggesting that blocking integrin β3 could offer a therapeutic strategy. We and other previously established that besides the adhesion-dependent functions, integrins can also be involved in different cellular mechanisms. In fact, we recently showed the ability of β3 to drive anchorage-independent growth in 3D without providing any growth or survival advantage in 2D[7]. Since there is also evidence that 3D cultures mimic drug sensitivity in vivo more accurately than 2D cultures[17], we focused on the role of β3 in promoting stemness and drug resistance using 3D culture models in vitro and tumor growth in vivo.

Although KRAS mutations, present in 95% of pancreatic tumors and 25% of lung cancers, have been linked to RTK inhibitor resistance, recent studies have demonstrated that expression of oncogenic KRAS is an incomplete predictor of erlotinib resistance in pancreatic and lung cancer, since a number of individual patients presenting with KRAS mutation unexpectedly respond to therapy. In fact, for 3D growth in soft agar and in vivo experiments, we found that erlotinib resistance could be predicted by evaluating integrin β3 expression in KRAS mutant cancers suggesting that oncogenic KRAS is not sufficient to drive erlotinib resistance. It has been demonstrated that its localization to the plasma membrane is a critical component to its function and inhibiting its membrane localization could represent a therapeutic strategy. Here, we revealed an unexpected role for integrin b3 that can maintain KRAS in membrane clusters through its interaction with Galectin-3 representing a potential therapeutic opportunity. KRAS dependency had previously been linked to erlotinib sensitivity for tumor cells growing in 2D[18]. These results emphasize the contribution of β3 integrin to tumor cell behavior for cells grown in 3D, and suggest that alternative or even opposing pathways may dominate when cells are grown in 2D under adherent conditions.

The invention thus provides methods for determining or predicting the course of cancer therapy in terms of personalized medicine. Our results demonstrate that biopsies taken at diagnosis can be screened for β3 expression to predict a poor response to RTK-targeted therapies. If a biopsy is positive, we would predict that co-administering an inhibitor of RalB/TBK1/RelA could improve the response. Since β3⁺ tumor cells are particularly sensitive to KRAS knockdown, such tumors represent a population of particularly good candidates for KRAS-directed therapies which have shown only poor responses thus far.

Our work demonstrates that a tumor could be sensitized to therapy by reversing the advantages of β3 expression. We demonstrate this can be achieved by inhibiting RalB-mediated signaling using genetic knockdown or by treating with a number of FDA-approved drugs. We focused our efforts on the role of β3 expression on lung and pancreatic cancers in the context of erlotinib therapy, since it is approved for these patients. However, we were able to correlate KRAS dependency and β3 expression for a diverse panel of epithelial cancer cells.

Methods

Compounds and Cell Culture.

Human pancreatic (FG, PANC-1), breast (MDAMB231 (MDA231) and lung (A549 and H1650) cancer cell lines were grown in ATCC recommended media supplemented with 10% fetal bovine serum, glutamine and non-essential amino acids. We obtained FG-β3, FG-D119A mutant and PANC-shβ3 cells as previously described. Erlotinib, linsitinib, Gemcitabine, Bortezomib and Lapatinib were purchased from Chemietek. Cisplatin was generated from Sigma-Aldrich.

Self Renewal Tumorsphere Assay and Soft Agar Assay.

Tumorsphere assay was performed as previously described. Soft agar formation assays were performed essentially as described previously. Cells were treated with vehicle (DMSO), erlotinib (10 nM to 5 µM), lapatinib (10 nM to 5 µM), gemcitabine (0.001 nM to 5 µM), linsitinib (10 nM to 5 µM), cisplatin (10 nM to 5 µM), or bortezomib (4 nM) diluted in DMSO. The media was replaced with fresh inhibitor 2/5 times a week. Survival curves were generated at least with five concentration points.

Limiting Dilution.

All mouse experiments were carried out in accordance with approved protocols from the UCSD animal subjects committee and with the guidelines set forth in the NIH Guide for the Care and Use of Laboratory Animals. $10^2$, $10^3$, $10^4$, $10^5$ and $10^6$ of A549 NS, A549 shβ3, FG, FG-β3 and FG-β3 sh RalB cells were suspended in a mixture of Basement Membrane Matrix Phenol Red-free (BD Biosciences) and PBS 1:1 and injected in the flanks of 6/8 weeks old female immune compromised nu/nu mice. After 30/40 days, palpable tumors were counted and the tumor-initiating cells frequency was calculated using the ELDA software.

Orthotopic Pancreas Cancer Xenograft Model.

Tumors were generated as previously described (JAY). Tumors were established for 2-3 weeks (tumor sizes were monitored by ultrasound) before beginning dosing. Mice were dosed by oral gavage with vehicle (6% captisol) or 10, 25 and 50 mg/kg/day erlotinib for 10 to 30 days prior to harvest.

Immunofluorescence Microscopy.

Frozen sections from tumors from patients diagnosed with pancreas or tumor cell lines were processed as previously described (Mielgo). Cells were stained with indicated primary, followed by secondary antibodies specific for mouse or rabbit (Invitrogen), as appropriate. Samples imaged on a Nikon Eclipse C1 confocal microscope with 1.4 NA 60× oil-immersion lens, using minimum pinhole (30 μm). Colocalization between Integrin β3 and KRAS was studied using the Zenon Antibody Labeling Kits (Invitrogen) and the KRAS rabbit antibody.

Biopsies from NSCLC Patients.

Tumor biopsies from University of California, San Diego (UCSD) Medical Center breast, pancreas and non-small cell lung cancer patients were obtained. This work was approved by the UCSD Institutional Review Board (IRB).

Cell Viability Assay.

Cell viability assays were performed as described[12]. Briefly cells were seeded in low adherent plates 7 days in DMEM containing 10% or 0% serum, 0.1% BSA.

Genetic knockdown and expression of mutant constructs.

Cells were transfected with vector control, WT, G23V RalB-FLAG, using a lentiviral system. For knock-down experiments, cells were transfected with KRAS, RalA, RalB, AKT1, ERK1/2, TBK1, siRNA (Qiagen) using the lipofectamine reagent (Invitrogen) following manufacturer's protocol or transfected with shRNA (Open Biosystems) using a lentiviral system. Gene silencing was confirmed by immunoblots analysis.

Immunohistochemical Analysis.

Immunostaining was performed according to the manufacturer's recommendations (Vector Labs) on 5 M sections of paraffin-embedded tumors from tumor biopsies from lung cancer patients. Tumor sections were processed as previously described[27] using integrin β3 (Abcam)+stem markers, diluted 1:200. Sections stained with integrin β3 were scored by a H-score according to the staining intensity (SI) on a scale 0 to 3 within the whole tissue section.

RNA Extraction PCR

Immunoprecipitation and Immunoblots.

Lysates from cell lines and xenograft tumors were generated using standard methods and RIPA or Triton buffers. Immunoprecipitation experiments were performed as previously described[59] with anti-integrin-3 (LM609) or Galectin-3. For immunoblot analysis, 25 μg of protein was boiled in Laemmli buffer and resolved on 8% to 15% gel. The following antibodies were used: anti-integrin β3 ( ), KRAS, NRAS, RRAS, HRAS, FAK and Hsp90 from Santa Cruz, phospho-S172 NAK/TBK1 from Epitomics, TBK1, phospho-p65NFκB S276, p65NFκB, RalB, phospho-EGFR, EGFR, phospho-FAK Tyr 861 from Cell Signaling Technology, and Galectin 3 from BioLegend.

Affinity Pull-Down Assays for Ras and Ral.

RAS and Ral activation assays were performed in accordance with the manufacturer's (Upstate) instruction. Briefly, cells were cultured in suspension for 3 h. 10 μg of Ral Assay Reagent (Ral BP1, agarose) or RAS assay reagent (Raf-1 RBD, agarose) was added to 500 mg to 1 mg of total cell protein in MLB buffer (Millipore). After 30 min of rocking at 4° C., the activated (GTP) forms of RAS/Ral bound to the agarose beads were collected by centrifugation, washed, boiled in Laemmli buffer, and loaded on a 15% SDS-PAGE gel.

Statistical Analyses.

All statistical analyses were performed using Prism software (GraphPad). Two-tailed Mann Whitney U tests, Chi-squared tests, Fisher's exact tests, one way ANOVA tests or t-tests were used to calculate statistical significance. A P value<0.05 was considered to be significant.

Figure Legends—Example 3

FIG. 1: Integrin β3 expression increase tumor-initiating and self-renewal capacities:

(a) Limiting dilution in vivo determining the frequency of tumor-initiating cells for A549 cells expressing non-target shRNA control or integrin β3-specific shRNA and for FG cells expressing control vector or integrin β3 (FG-β3). The frequency of tumor-initiating cells per 10,000 cells was calculated using the ELDA extreme limiting dilution software. (b-c-d) Self-renewal capacity of A549 and PANC-1 cells expressing non-target shRNA control (CTRL) or integrin β3-specific shRNA and of FG expressing control vector or integrin β3 (FG-β3), measured by quantifying the number of primary and secondary tumorspheres. Representative images of tumorspheres are shown. n=3; mean±SEM. *P<0.05, **P<0.01.

FIG. 2: Integrin β3 drives resistance to EGFR inhibitors:

(a) Effect of integrin β3 expression (ectopic expression for FG and integrin β3-specific knockdown for PANC-1) cells on drug treatment response. Cells were treated with a dose response of gemcitabine, cisplatin, erlotinib, lapatinib and linsitinib. Results are normalized using non-treated cells as controls. n=3; mean±SEM. *P<0.05, **P<0.001. (b) Effect of integrin β3 knockdown on erlotinib response in MDA-MB-231 (MDA231), A549 and H1650. n=3; mean±SEM. *P<0.05, **P<0.001. (c) Effect of integrin β3 knockdown on erlotinib resistance in vivo, A549 shCTRL and A549 shβ3 (n=8 per treatment group) were treated with erlotinib (25 mg/kg/day) or vehicle during 16 days. Tumor volumes are expressed as mean±SEM. *P<0.05. (d) Orthotopic FG and FG-β3 tumors (>1000 mm$^3$; n=5 per treatment group) were treated for 30 days with vehicle or erlotinib. Results are expressed as % tumor weight compared to vehicle control. *P<0.05. (e) Effect of erlotinib treatment on HCC827 xenograft tumors (n=8 tumors per treatment group). HCC827 cells were treated with vehicle control or erlotinib (12.5 mg/kg/day) until acquired resistance. (f) Relative mRNA expression of integrin β3 (ITGB3) in HCC827 vehicle-treated tumors (n=5) or erlotinib-treated tumors (n=7) from (e) after acquired resistance. Data are mean±SE; **P<0.001. (g) H&E sections and immunohistochemical analysis of integrin β3 expression in paired human lung cancer biopsies obtained before and after erlotinib resistance. Scale bar, 50 μm. (h) Limiting dilution in vivo determining the frequency of tumor-initiating cells for HCC827 vehicle-treated (vehicle) and erlotinib-treated tumors from (erlotinib resistant non-sorted) (e). The HCC827 erlotinib-treated tumors have been digested and sorted in two groups: the integrin β3− and the integrin β3+ population. (i) and (j) Self-renewal capacity of HCC827 vehicle-treated (vehicle), erlotinib-treated (erlotinib resistant non-sorted), erlotinib-treated integrin β3− population and erlotinib-treated integrin β3+ population, measured by quantifying the number of primary and secondary tumorspheres. n=3; mean±SEM. *P<0.05, **P<0.01.

FIG. 3: Integrin β3/KRAS complex is critical for integrin β3-mediated stemness:

(a) Confocal microscopy images show immunostaining for Integrin β3 (green), KRAS (red) and DNA (TOPRO-3, blue) for FG-β3, PANC-1, A549 and HCC827 after acquired resistance to erlotinib (HCC827 ER) grown in suspension. Arrows indicate clusters where integrin β3 and KRAS colocalize (yellow). Scale bar=10 μm. Data are representative of three independent experiments. (b) Ras activity was determined in PANC-1 cells grown in suspension by using a GST-Rafl-RBD immunoprecipitation assay Immunoblots indicate KRAS activity and association of active KRAS with integrin β3. Data are representative of three independent experiments. (c) Effect of KRAS knockdown on tumorspheres formation in lung (A549 and H441) and pancreatic (FG and PANC-1) cancer cells expressing or lacking integrin β3. n=3 mean±SEM. *P<0.05, **P<0.01. (d) Effect of KRAS knockdown on erlotinib resistance of β3-negative and β3-positive epithelial cancer cell lines. Cells were treated with a dose response of erlotinib. n=3; mean±SEM, *P<0.05, **P<0.01. (e) Self-renewal capacity of FG-β3 cells expressing non-target shRNA control (shCTRL) or KRAS-specific shRNA measured by quantifying the number of primary and secondary tumorspheres. n=3; mean±SEM. *P<0.05, **P<0.01. (f) Confocal microscopy images show immunostaining for integrin β3 (green), KRAS (red) and DNA (TOPRO-3, blue) for PANC-1 cells expressing non-target shRNA control or Galectin 3-specific shRNA grown in suspension. Scale bar=10 μm. Data are representative of three independent experiments. (g) immunoblot analysis of integrin β3 immunoprecipitates from PANC-1 cells expressing non-target shRNA control (CTRL) or Galectin-3-specific shRNA (Gal-3). Data are representative of three independent experiments. (h) Effect of Galectin-3 knockdown on integrin β3-mediated anchorage independent growth and erlotinib resistance. PANC-1 cells expressing a non-target shRNA control or a Galectin-3-specific shRNA (sh Gal-3) were treated with vehicle or erlotinib (0.5 μM). n=3; mean±SEM. (i) Self-renewal capacity of PANC-1 cells expressing non-target shRNA control (shCTRL) or Galectin-3-specific shRNA (sh Gal-3) measured by quantifying the number of primary and secondary tumorspheres. n=3; mean±SEM. *P<0.05, **P<0.01.

FIG. 4. RalB/TBK1 signaling is a key modulator of integrin β3-mediated stemness:

(a) Effect of RalB knockdown on anchorage independence. n=3; mean±SEM, *P<0.05, **P<0.01. (b) Self-renewal capacity of FG-β3 cells expressing non-target shRNA control (sh CTRL) or RalB-specific shRNA (sh RalB) measured by quantifying the number of primary and secondary tumorspheres. n=3; mean±SEM. *P<0.05, **P<0.01. (c) Limiting dilution in vivo determining the frequency of tumor-initiating cells for FG-β3 cells expressing non-target shRNA control or integrin RalB-specific shRNA. (d) Effect of RalB knockdown on erlotinib resistance of β3-positive epithelial cancer cell lines. Cells were treated with 0.5 μM of erlotinib. n=3; mean±SEM, *P<0.05, **P<0.01. (e) Effect of RalB knockdown on erlotinib resistance of β3-positive human pancreatic (FG-β3) orthotopic tumor xenografts. Established tumors expressing non-target shRNA, (sh CTRL) or a shRNA targeting RalB (sh RalB) (>1000 mm$^3$; n=13 per treatment group) were randomized and treated for 10 days with vehicle or erlotinib. Results are expressed as % of tumor weight changes after erlotinib treatment compared to vehicle. *P<0.05. (f) Immunoblot analysis of FG and FG-β3 stably expressing non-target shRNA control or RalB-specific shRNA, grown in 3D and treated with erlotinib (0.5 μM). Data are representative of three independent experiments. (g) Effect of TBK1 knockdown on PANC-1 self-renewal capacity. n=3; mean±SEM. *P<0.05, **P<0.01. (h) Effect of TBK1 knockdown on erlotinib resistance of PANC-1 cells. Cells were treated with 0.5 μM of erlotinib. n=3; mean±SEM. *P<0.05, **P<0.01. (i) Mice bearing subcutaneous β3-positive tumors (PANC-1) were treated with vehicle, erlotinib (25 mg/kg/day), amlexanox (25 mg/kg/day) or the combination of erlotinib and amlexanox. Tumor dimensions are reported as the fold change relative to size of the same tumor on Day 1. Mean±SEM, (A) *P=0.042 using a one way ANOVA test. n=8 mice per group.

FIG. S1—Example 3

(a-b) Limiting dilution tables. (c) Immunoblots showing integrin β3 knockdown or ectopic expression efficiency in cells used in FIG. 1. (d) Viability assay (CellTiter-Glo assay) of FG and FG-β3 cells grown in 3D in media with or without serum. n=3; mean+SEM. *P<0.05. **P<0.01. (e) Immunohistochemical analysis of integrin β3 expression in paired human lung cancer biopsies obtained before and after erlotinib resistance. Scale bar, 50 μm. (f) Limiting dilution table. (g) Immunohistochemistry staining of CD166 and integrin β3 in human lung tumor biopsies after EGFR™ acquired resistance.

FIG. S2—Example 3

(a) Effect of cilengetide treatment on erlotinib resistance in FG-β3 and PANC-1 cells. n=3; mean+SEM. (b) Effect of ectopic expression of β3 wild-type (FG-β3) or the β3 D119A (FG-D119A) ligand binding domain mutant on erlotinib response. n=3; mean±SEM Immunoblot showing transfection efficiency of vector control, integrin β3 wild-type and integrin 3 D119A. (c) Confocal microscopy images of FG-β3 cells grown in 3D and stained for integrin—β3 (green) and RAS family members (red). Scale bar, 10 μm. Data are representative of three independent experiments. (d) Immunoblots showing KRAS knockdown efficiency in cells used in FIG. 3. (e) Representative photographs of crystal violet-stained tumorspheres of FG and A549 cells expressing non-target shRNA control or specific-KRAS. (f) Effect of a second KRAS knockdown (shKRAS 2) on tumorspheres formation in PANC-1 stably expressing non-target shRNA control (3-positive) or specific-integrin-β3 shRNA (3 negative). n=3; mean+SEM. *P<0.05.

FIG. S3—Example 3

(a) Effect of ERK, AKT and RalA knockdown on erlotinib response of β3-negative FG and 3-positive FG-3 cells. (b) Immunoblots showing ERK, AKT and RalA knockdown efficiency in cells used in (a). (c) Immunoblots showing RalB knockdown efficiency in cells used in FIG. 3. (d) Effect of a second RalB knockdown (shRalB 2) on tumorspheres formation in PANC-1 stably expressing non-target shRNA control (β3-positive) or specific-integrin β3 shRNA (β3 negative). n=3; mean+SEM. *P<0.05. (e) Limiting dilution table. (f) Confocal microscopy images of integrin αvβ3 (green), RalB (red) and DNA (TOPRO-3, blue) in tumor biopsies from pancreatic cancer patients. Scale bar, 20 μm. (g) Ral activity was determined in PANC-1 cells grown in suspension by using a GST-RalBP1-RBD immunoprecipitation assay Immunoblots indicate RalA and RalB activities. Data are representative of three independent experiments. (h) Effect of β3 expression and KRAS expression on RalB activity, measured using a GST-RalBP1-RBD immunoprecipitation assay. Data are representative of three independent experiments. (i) Effect of expression of a constitutively active Ral G23V mutant on erlotinib resistance of β3 positive and negative cells. n=3; mean±SEM. *P<0.05.

FIG. S4—Example 3

(a) Immunoblot showing TBK1 knockdown efficiency in PANC-1 cells used in FIG. 4. (b) Effect of theTBK1 inhibitor amlexanox on erlotinib response of PANC-1 cells. Cells were treated with vehicle, erlotinib (0.5 µM), amlexanox alone or in combination. (c) Effect of the NFkB inhibitor borthezomib on β3-positive cells (FG-β3, PANC-1 and A549). Cells were treated with vehicle, erlotinib (0.5 µM), bortezomib (4 nM) alone or in combination. n=3; mean±SEM. *P<0.05, **P<0.01. (d) Mice bearing subcutaneous β3-positive tumors (FG-β3) were treated with vehicle, erlotinib (25 mg/kg/day), bortezomib (0.25 mg/kg), the combination of erlotinib and bortezomib. Tumor dimensions are reported as the fold change relative to size of the same tumor on Day 1. *P=x using a one way ANOVA test. n=8 mice per group. (e) Confocal microscopy images of cleaved caspase 3 (red) and DNA (TOPRO-3, blue) in tumor biopsies from xenografts tumors used in (d) treated with vehicle, erlotinib, bortezomib or bortezomib and erlotinib in combo. Scale bar, 20 µm.

References—Example 3

1. Desgrosellier, J. S. & Cheresh, D. A. Integrins in cancer: biological implications and therapeutic opportunities. *Nat Rev Cancer* 10, 9-22 (2010).
2. Singh, A. & Settleman, J. EMT, cancer stem cells and drug resistance: an emerging axis of evil in the war on cancer. *Oncogene* 29, 4741-4751 (2010).
3. Lo, P. K., et al. CD49f and CD61 identify Her2/neu-induced mammary tumor-initiating cells that are potentially derived from luminal progenitors and maintained by the integrin-TGFbeta signaling. *Oncogene* (2011).
4. Vaillant, F., et al. The mammary progenitor marker CD61/beta3 integrin identifies cancer stem cells in mouse models of mammary tumorigenesis. *Cancer Res* 68, 7711-7717 (2008).
5. Galliher, A. J. & Schiemann, W. P. Beta3 integrin and Src facilitate transforming growth factor-beta mediated induction of epithelial-mesenchymal transition in mammary epithelial cells. *Breast cancer research: BCR* 8, R42 (2006).
6. Mamuya, F. A. & Duncan, M. K. aV integrins and TGF-beta-induced EMT: a circle of regulation. *Journal of cellular and molecular medicine* 16, 445-455 (2012).
7. Desgrosellier, J. S., et al. An integrin alpha(v)beta(3)-c-Src oncogenic unit promotes anchorage-independence and tumor progression. *Nat Med* 15, 1163-1169 (2009).
8. Boudreau, N., et al. Induction of the angiogenic phenotype by Hox D3. *J Cell Biol* 139, 257-264 (1997).
9. Dean, M., Fojo, T. & Bates, S. Tumour stem cells and drug resistance. *Nature Reviews Cancer* 5, 275-284 (2005).
10. Martin, K. H., et al. Integrin Connections Map: To Infinity and Beyond. *Science* 296, 1652-1653 (2002).
11. Newlaczyl, A. U. & Yu, L. G. Galectin-3—a jack-of-all-trades in cancer. *Cancer letters* 313, 123-128 (2011).
12. Shalom-Feuerstein, R., et al. K-ras nanoclustering is subverted by overexpression of the scaffold protein galectin-3. *Cancer research* 68, 6608-6616 (2008).
13. Markowska, A. I., Liu, F. T. & Panjwani, N. Galectin-3 is an important mediator of VEGF- and bFGF-mediated angiogenic response. *J Exp Med* 207, 1981-1993 (2010).
14. Pylayeva-Gupta, Y., Grabocka, E. & Bar-Sagi, D. RAS oncogenes: weaving a tumorigenic web. *Nat Rev Cancer* 11, 761-774 (2011).
15. Delhase, M., et al. TANK-binding kinase 1 (TBK1) controls cell survival through PAI-2/serpinB2 and trans-glutaminase 2. *Proceedings of the National Academy of Sciences of the United States of America* 109, E177-186 (2012).
16. Jinushi, M., et al. ATM-mediated DNA damage signals mediate immune escape through integrin-alphavbeta3-dependent mechanisms. *Cancer Res* 72, 56-65 (2012).
17. Schmeichel, K. L. & Bissell, M. J. Modeling tissue-specific signaling and organ function in three dimensions. *Journal of cell science* 116, 2377-2388 (2003).
18. Singh, A., et al. A gene expression signature associated with "K-Ras addiction" reveals regulators of EMT and tumor cell survival. *Cancer Cell* 15, 489-500 (2009).

A number of embodiments of the invention have been described. Nevertheless, it will be understood that various modifications may be made without departing from the spirit and scope of the invention. Accordingly, other embodiments are within the scope of the following claims.

What is claimed is:

1. A method for: overcoming or diminishing a Growth Factor Inhibitor (GFI) resistance in a cell, or sensitizing, increasing sensitivity to or re-sensitizing a tumor that is resistant to a cancer or anti-tumor Growth Factor Inhibitor (GFI) drug, wherein the Growth Factor Inhibitor is an erlotinib, a linsitinib, a lapatinib or a lenalidomide, comprising administering to the cell or an individual in need thereof at least one compound, composition or formulation comprising an inhibitor of Galectin-3; thereby overcoming or diminishing the Growth Factor Inhibitor (GFI) resistance in the cell, or sensitizing, increasing sensitivity or re-sensitizing the tumor that is resistant to the cancer or anti-tumor Growth Factor Inhibitor (GFI) drug.

2. The method of claim 1, wherein:
    (a) the at least one compound, composition or formulation, or combination of compounds, is formulated as a pharmaceutical composition;
    (b) the method of (a), wherein the compound, composition or formulation or pharmaceutical composition is administered in vitro, ex vivo or in vivo, or is administered to an individual in need thereof; or
    (c) the method of (a) or (b), wherein the at least one compound, composition or formulation is a pharmaceutical composition which is formulated for administration intravenously (IV), parenterally, nasally, topically, orally, or by liposome or targeted or vessel-targeted nanoparticle delivery.

3. The method of claim 1, wherein the growth factor inhibitor or Growth Factor Inhibitor (GFI) drug comprises an erlotinib or a lapatinib.

4. The method of claim 1, wherein the Growth Factor Inhibitor or Growth Factor Inhibitor (GFI) drug decreases, slows or blocks new blood vessel growth, neovascularization or angiogenesis; or, wherein the administering of the Growth Factor Inhibitor treats or ameliorates conditions that are responsive to blocking or slowing cell growth, and/or the development of neovascularization or new blood vessels.

5. The method of claim 1, wherein the at least one compound, composition or formulation, or combination of compounds further comprises at least one growth factor inhibitor or Growth Factor Inhibitor (GFI) drug.

6. A method for: sensitizing, increasing sensitivity to or re-sensitizing a tumor that is resistant to a Receptor Tyrosine Kinase (RTK) inhibitor in an individual in need thereof, wherein the RTK inhibitor is an erlotinib, a lapatinib or a lenalidomide, comprising administering a sufficient amount of at least one compound, composition or formulation to the individual in need thereof, wherein the at least one compound, composition or formulation comprises an inhibitor of Galectin-3.

7. The method of claim 6, wherein the RTK inhibitor is an erlotinib or a lapatinib.

8. The method of claim 1, wherein the inhibitor of Galectin-3 comprises a Galectin-3-specific shRNA (sh Gal-3).

9. The method of claim 6, wherein the inhibitor of Galectin-3 comprises a Galectin-3-specific shRNA (sh Gal-3).

10. The method of claim 6, wherein:
(a) the at least one compound, composition or formulation, or combination of compounds, is formulated as a pharmaceutical composition;
(b) the method of (a), wherein the compound, composition or formulation or pharmaceutical composition is administered ex vivo or in vivo to the individual in need thereof; or
(c) the method of (a) or (b), wherein the at least one compound, composition or formulation is a pharmaceutical composition which is formulated for administration intravenously (IV), parenterally, nasally, topically, orally, or by liposome or targeted or vessel-targeted nanoparticle delivery.

11. The method of claim 6, wherein the method reduces, treats or ameliorates the level of disease in a cancer or a carcinoma.

12. The method of claim 11, wherein the cancer or a carcinoma is a glioblastoma, a neuroma, a neuroblastoma or a colon carcinoma.

13. The method of claim 1, wherein the method reduces, treats or ameliorates a cancer or carcinoma.

14. The method of claim 13, wherein the cancer or carcinoma is a glioblastoma, a neuroma, a neuroblastoma, a colon carcinoma.

* * * * *